US008693523B2

(12) United States Patent
Feher

(10) Patent No.: US 8,693,523 B2
(45) Date of Patent: Apr. 8, 2014

(54) QAM CDMA AND TDMA COMMUNICATION METHODS

(76) Inventor: Kamilo Feher, El Macero, CA (US)

( * ) Notice: Subject to any disclaimer, the term of this patent is extended or adjusted under 35 U.S.C. 154(b) by 8 days.

(21) Appl. No.: 13/602,286

(22) Filed: Sep. 3, 2012

(65) Prior Publication Data

US 2012/0321007 A1 Dec. 20, 2012

Related U.S. Application Data

(63) Continuation of application No. 13/282,461, filed on Oct. 27, 2011, now Pat. No. 8,259,832, which is a continuation of application No. 11/937,467, filed on Nov. 8, 2007, now Pat. No. 8,050,345, which is a continuation of application No. 10/831,724, filed on Apr. 24, 2004, now Pat. No. 7,593,481, which is a continuation of application No. 09/370,362, filed on Aug. 9, 1999, now Pat. No. 6,757,334.

(60) Provisional application No. 60/095,943, filed on Aug. 10, 1998.

(51) Int. Cl.
*H04B 1/69* (2011.01)
*H04Q 11/00* (2006.01)
*H04B 7/208* (2006.01)
*H04B 7/212* (2006.01)

(52) U.S. Cl.
USPC ........... 375/141; 375/144; 375/259; 375/377; 370/344; 370/347

(58) Field of Classification Search
USPC ......... 375/130, 140, 141–144, 146–148, 150, 375/259, 260, 219, 295, 298, 299, 229, 232, 375/233, 261, 267, 316, 340, 347, 371, 274, 375/302, 305, 377, 343; 370/335, 337, 342, 370/344, 345, 347, 441, 442
See application file for complete search history.

(56) References Cited

U.S. PATENT DOCUMENTS 3,702,476 A 11/1972 Nathanson et al.
3,944,926 A 3/1976 Feher
(Continued)

FOREIGN PATENT DOCUMENTS

AU 2005335219 1/2010
CN 0512333 1/2008
(Continued)

OTHER PUBLICATIONS

Isabelle Siaud et al., "Interleaving based Resource Allocation Algorithm for Multi Gigabit Wireless OFDM system," IEEE conferences, Nov. 30, 2011-to-Dec. 1, 2011, pp. 1-5.*

(Continued)

*Primary Examiner* — Tesfaldet Bocure

(57) ABSTRACT

Filtering and modulating a first rate data signal into a Quadrature Amplitude Modulated (QAM) Code Division Multiple Access (CDMA) and a second rate data signal into a Time Division Multiple Access (TDMA) modulated signal and selecting between the transmission of the CDMA and TDMA modulated signals. A method for nonlinearly and linearly amplifying TDMA and CDMA signals. A diversity receiver and demodulator method for receiving and demodulating transmitted modulated signals. Processing, transmit baseband filtering and modulating signals for providing cross-correlated in-phase and quadrature-phase Gaussian filtered Gaussian Minimum Shift Keying (GMSK) and other cross-correlated modulated signals and spread spectrum Quadrature Phase Shift Keying (QPSK) modulated signals. Transmit processing and filtering for providing time division multiplexed (TDM) Gaussian filtered baseband signal and Orthogonal Frequency Division Multiplexed (OFDM) in-phase and quadrature-phase baseband modulated signal to a cellular network and to separate wireless network.

20 Claims, 45 Drawing Sheets

(56) References Cited

U.S. PATENT DOCUMENTS

| | | |
|---|---|---|
| 4,030,033 A | 6/1977 | Bibl et al. |
| 4,229,821 A | 10/1980 | De Jager et al. |
| 4,339,724 A | 7/1982 | Feher |
| 4,350,879 A | 9/1982 | Feher |
| 4,531,221 A | 7/1985 | Chung et al. |
| 4,567,602 A | 1/1986 | Kato et al. |
| 4,584,880 A | 4/1986 | Matzuk |
| 4,644,565 A | 2/1987 | Seo et al. |
| 4,720,839 A | 1/1988 | Feher et al. |
| 4,742,532 A | 5/1988 | Walker |
| 4,745,628 A | 5/1988 | McDavid et al. |
| 4,852,090 A | 7/1989 | Borth |
| 4,945,549 A | 7/1990 | Simon et al. |
| 4,962,510 A | 10/1990 | McDavid et al. |
| 5,084,903 A | 1/1992 | McNamara et al. |
| 5,103,459 A | 4/1992 | Gilhousen et al. |
| 5,107,260 A | 4/1992 | Meissner |
| 5,157,686 A | 10/1992 | Omura et al. |
| 5,185,765 A | 2/1993 | Walker |
| 5,282,222 A | 1/1994 | Fattouche et al. |
| 5,299,228 A | 3/1994 | Hall |
| 5,313,173 A | 5/1994 | Lampe |
| 5,345,439 A | 9/1994 | Marston |
| 5,359,521 A | 10/1994 | Kyrtsos et al. |
| 5,430,416 A | 7/1995 | Black et al. |
| 5,479,448 A | 12/1995 | Seshadri |
| 5,488,631 A | 1/1996 | Gold et al. |
| 5,491,457 A | 2/1996 | Feher |
| 5,497,777 A | 3/1996 | Abdel-Malek et al. |
| 5,535,432 A | 7/1996 | Dent |
| 5,539,730 A | 7/1996 | Dent |
| 5,550,881 A | 8/1996 | Sridhar et al. |
| 5,564,076 A | 10/1996 | Auvray |
| 5,572,516 A | 11/1996 | Miya et al. |
| 5,596,333 A | 1/1997 | Bruckert |
| 5,608,722 A | 3/1997 | Miller |
| 5,663,757 A | 9/1997 | Morales |
| 5,668,880 A | 9/1997 | Alajajian |
| 5,722,068 A | 2/1998 | Bartle et al. |
| 5,745,480 A | 4/1998 | Behtash et al. |
| 5,757,858 A | 5/1998 | Black et al. |
| 5,778,024 A | 7/1998 | McDonough |
| 5,784,402 A | 7/1998 | Feher |
| 5,794,159 A | 8/1998 | Portin |
| 5,815,525 A | 9/1998 | Smith et al. |
| 5,818,827 A | 10/1998 | Usui et al. |
| 5,842,140 A | 11/1998 | Dent et al. |
| 5,850,392 A | 12/1998 | Wang et al. |
| 5,903,592 A | 5/1999 | Itaya |
| 5,909,435 A | 6/1999 | Apelewicz |
| 5,909,460 A | 6/1999 | Dent |
| 5,915,207 A | 6/1999 | Dao et al. |
| 5,930,303 A | 7/1999 | Walker |
| 5,933,421 A | 8/1999 | Alamouti et al. |
| 5,943,361 A | 8/1999 | Gilhousen et al. |
| 5,982,819 A | 11/1999 | Womack et al. |
| 5,999,519 A | 12/1999 | Basile et al. |
| 6,006,105 A | 12/1999 | Rostoker et al. |
| 6,008,703 A | 12/1999 | Perrott et al. |
| 6,014,551 A | 1/2000 | Pesola et al. |
| 6,035,212 A | 3/2000 | Rostoker et al. |
| 6,037,991 A | 3/2000 | Thro et al. |
| 6,067,018 A | 5/2000 | Skelton et al. |
| 6,075,973 A | 6/2000 | Greeff et al. |
| 6,078,576 A | 6/2000 | Schilling et al. |
| 6,088,585 A | 7/2000 | Schmitt et al. |
| 6,101,174 A | 8/2000 | Langston |
| 6,101,224 A | 8/2000 | Lindoff et al. |
| 6,107,959 A | 8/2000 | Levanon |
| 6,128,330 A | 10/2000 | Schilling |
| 6,167,099 A | 12/2000 | Rader et al. |
| 6,177,861 B1 | 1/2001 | MacLellan et al. |
| 6,192,070 B1 | 2/2001 | Poon et al. |
| 6,195,563 B1 | 2/2001 | Samuels |
| 6,198,777 B1 | 3/2001 | Feher |
| 6,208,875 B1 | 3/2001 | Damgaard et al. |
| 6,216,012 B1 | 4/2001 | Jensen |
| 6,229,479 B1 | 5/2001 | Kozlov et al. |
| 6,240,133 B1 | 5/2001 | Sommer et al. |
| 6,249,252 B1 | 6/2001 | Dupray |
| 6,256,508 B1 | 7/2001 | Nakagawa et al. |
| 6,269,246 B1 | 7/2001 | Rao et al. |
| 6,282,184 B1 | 8/2001 | Lehman et al. |
| 6,298,244 B1 | 10/2001 | Boesch et al. |
| 6,321,090 B1 | 11/2001 | Soliman |
| 6,332,083 B1 | 12/2001 | Shi et al. |
| 6,389,055 B1 | 5/2002 | August et al. |
| 6,393,294 B1 | 5/2002 | Perez-Breva et al. |
| 6,418,324 B1 | 7/2002 | Doviak et al. |
| 6,424,867 B1 | 7/2002 | Snell et al. |
| 6,430,695 B1 | 8/2002 | Bray et al. |
| 6,445,749 B2 | 9/2002 | Feher |
| 6,448,022 B1 | 9/2002 | Braunstein et al. |
| 6,466,163 B2 | 10/2002 | Naruse et al. |
| 6,470,055 B1 | 10/2002 | Feher |
| 6,522,895 B1 | 2/2003 | Montalvo |
| 6,535,320 B1 | 3/2003 | Burns |
| 6,535,561 B2 | 3/2003 | Boesch et al. |
| 6,539,253 B2 | 3/2003 | Thompson et al. |
| 6,546,044 B1 | 4/2003 | Dent et al. |
| 6,574,211 B2 | 6/2003 | Padovani et al. |
| 6,577,229 B1 | 6/2003 | Bonneau et al. |
| 6,591,084 B1 | 7/2003 | Chuprun et al. |
| 6,665,348 B1 | 12/2003 | Feher |
| 6,711,440 B2 | 3/2004 | Deal et al. |
| 6,745,126 B1 | 6/2004 | Pavlak et al. |
| 6,748,021 B1 | 6/2004 | Daly |
| 6,748,022 B1 | 6/2004 | Walker |
| 6,757,334 B1 | 6/2004 | Feher |
| 6,763,226 B1 | 7/2004 | McZeal, Jr. |
| 6,772,063 B2 | 8/2004 | Ihara et al. |
| 6,775,254 B1 | 8/2004 | Willenegger et al. |
| 6,775,371 B2 | 8/2004 | Elsey et al. |
| 6,788,946 B2 | 9/2004 | Winchell et al. |
| 6,807,564 B1 | 10/2004 | Zellner et al. |
| 6,823,181 B1 | 11/2004 | Kohno et al. |
| 6,834,073 B1 | 12/2004 | Miller et al. |
| 6,842,617 B2 | 1/2005 | Williams et al. |
| 6,865,395 B2 | 3/2005 | Riley |
| 6,876,310 B2 | 4/2005 | Dunstan |
| 6,876,859 B2 | 4/2005 | Anderson et al. |
| 6,879,584 B2 | 4/2005 | Thro et al. |
| 6,879,842 B2 | 4/2005 | King et al. |
| 6,882,313 B1 | 4/2005 | Fan et al. |
| 6,889,135 B2 | 5/2005 | Curatolo et al. |
| 6,897,952 B1 | 5/2005 | Hagler |
| 6,901,112 B2 | 5/2005 | McCorkle |
| 6,906,996 B2 | 6/2005 | Ballantyne |
| 6,928,101 B2 | 8/2005 | Feher |
| 6,961,441 B1 | 11/2005 | Hershey et al. |
| 6,963,659 B2 | 11/2005 | Tumey et al. |
| 6,968,014 B1 | 11/2005 | Bobier |
| 6,999,759 B2 | 2/2006 | Harris et al. |
| 7,004,910 B2 | 2/2006 | Lindsey |
| 7,006,073 B2 | 2/2006 | Lieu |
| 7,035,344 B2 | 4/2006 | Feher |
| 7,043,268 B2 | 5/2006 | Yukie et al. |
| 7,057,512 B2 | 6/2006 | Stilp |
| 7,068,738 B2 | 6/2006 | Lee et al. |
| 7,076,211 B2 | 7/2006 | Donner et al. |
| 7,079,584 B2 | 7/2006 | Feher |
| 7,103,085 B2 | 9/2006 | Dabak et al. |
| 7,110,433 B2 | 9/2006 | Feher |
| 7,133,456 B2 | 11/2006 | Feher |
| 7,133,471 B2 | 11/2006 | Feher |
| 7,162,236 B2 | 1/2007 | Dorenbosch et al. |
| 7,203,262 B2 | 4/2007 | Moy et al. |
| 7,215,984 B2 | 5/2007 | Diab et al. |
| 7,228,136 B2 | 6/2007 | Myllymaki |
| 7,236,883 B2 | 6/2007 | Garin et al. |
| 7,245,668 B2 | 7/2007 | Feher |
| 7,260,366 B2 | 8/2007 | Lee et al. |
| 7,260,369 B2 | 8/2007 | Feher |
| 7,263,133 B1 | 8/2007 | Miao |

(56) References Cited

U.S. PATENT DOCUMENTS

| | | |
|---|---|---|
| 7,280,607 B2 | 10/2007 | McCorkle et al. |
| 7,280,810 B2 | 10/2007 | Feher |
| 7,286,592 B2 | 10/2007 | Pietila et al. |
| 7,319,878 B2 | 1/2008 | Sheynblat et al. |
| 7,321,783 B2 | 1/2008 | Kim |
| 7,356,343 B2 | 4/2008 | Feher |
| 7,359,449 B2 | 4/2008 | Feher |
| 7,376,180 B2 | 5/2008 | Feher |
| 7,415,066 B2 | 8/2008 | Feher |
| 7,418,028 B2 | 8/2008 | Feher |
| 7,421,004 B2 | 9/2008 | Feher |
| 7,423,958 B2 | 9/2008 | Schrader et al. |
| 7,426,248 B2 | 9/2008 | Feher |
| 7,440,488 B2 | 10/2008 | Feher |
| 7,440,516 B2 | 10/2008 | Kim et al. |
| 7,450,628 B2 | 11/2008 | Feher |
| 7,457,385 B2 | 11/2008 | Feher |
| 7,466,975 B2 | 12/2008 | Feher |
| 7,483,492 B2 | 1/2009 | Feher |
| 7,545,883 B2 | 6/2009 | Feher |
| 7,548,787 B2 | 6/2009 | Feher |
| 7,551,685 B2 | 6/2009 | Yang et al. |
| 7,555,054 B2 | 6/2009 | Feher |
| 7,558,313 B2 | 7/2009 | Feher |
| 7,558,574 B2 | 7/2009 | Feher |
| 7,561,881 B2 | 7/2009 | Feher |
| 7,593,481 B2 | 9/2009 | Feher |
| 7,593,733 B2 | 9/2009 | Feher |
| 7,603,125 B2 | 10/2009 | Feher |
| 7,627,320 B2 | 12/2009 | Feher |
| 7,630,717 B2 | 12/2009 | Feher |
| 7,693,229 B2 | 4/2010 | Feher |
| 7,711,368 B2 | 5/2010 | Feher |
| 7,720,488 B2 | 5/2010 | Feher |
| 7,725,114 B2 | 5/2010 | Feher |
| 7,738,608 B2 | 6/2010 | Feher |
| 7,769,386 B2 | 8/2010 | Feher |
| 7,783,291 B2 | 8/2010 | Feher |
| 7,787,882 B2 | 8/2010 | Feher |
| 7,805,143 B2 | 9/2010 | Feher |
| 7,809,374 B2 | 10/2010 | Feher |
| 7,877,110 B2 | 1/2011 | Feher |
| 7,885,650 B2 | 2/2011 | Feher |
| 7,894,810 B2 | 2/2011 | Feher |
| 7,899,491 B2 | 3/2011 | Feher |
| 7,904,041 B2 | 3/2011 | Feher |
| 7,917,103 B2 | 3/2011 | Feher |
| 7,937,093 B2 | 5/2011 | Feher |
| 7,937,094 B2 | 5/2011 | Feher |
| 7,949,405 B2 | 5/2011 | Feher |
| 7,961,815 B2 | 6/2011 | Feher |
| 7,978,774 B2 | 7/2011 | Feher |
| 7,983,678 B2 | 7/2011 | Feher |
| 8,050,345 B1 | 11/2011 | Feher |
| 8,055,269 B2 | 11/2011 | Feher |
| 8,085,705 B2 | 12/2011 | Feher |
| 8,098,753 B2 | 1/2012 | Feher |
| 8,112,110 B2 | 2/2012 | Feher |
| 8,150,453 B2 | 4/2012 | Feher |
| 8,185,069 B1 | 5/2012 | Feher |
| 8,189,703 B2 | 5/2012 | Feher |
| 8,190,143 B1 | 5/2012 | Feher |
| 8,190,193 B2 | 5/2012 | Feher |
| 8,200,243 B1 | 6/2012 | Feher |
| 2001/0000456 A1 | 4/2001 | McGowan |
| 2001/0016013 A1 | 8/2001 | Feher |
| 2001/0020912 A1 | 9/2001 | Naruse et al. |
| 2002/0001337 A1 | 1/2002 | Chauncey et al. |
| 2002/0032875 A1 | 3/2002 | Kashani |
| 2002/0063622 A1 | 5/2002 | Armstrong et al. |
| 2002/0085641 A1 | 7/2002 | Baum |
| 2002/0086684 A1 | 7/2002 | Pande et al. |
| 2002/0188575 A1 | 12/2002 | Freeny, Jr. |
| 2002/0193108 A1 | 12/2002 | Robinett |
| 2003/0003874 A1 | 1/2003 | Nitta et al. |
| 2003/0025599 A1 | 2/2003 | Monroe |
| 2003/0048834 A1 | 3/2003 | Feher |
| 2003/0063683 A1 | 4/2003 | Macfarlane Shearer et al. |
| 2003/0069043 A1 | 4/2003 | Chhaochharia et al. |
| 2003/0097049 A1 | 5/2003 | Diab et al. |
| 2003/0120742 A1 | 6/2003 | Ohgami et al. |
| 2003/0129964 A1 | 7/2003 | Kohinata et al. |
| 2003/0130009 A1 | 7/2003 | Kung |
| 2003/0134664 A1 | 7/2003 | Zancewicz |
| 2003/0147471 A1 | 8/2003 | Simon et al. |
| 2003/0179833 A1 | 9/2003 | Porco et al. |
| 2004/0013166 A1 | 1/2004 | Goodings |
| 2004/0017858 A1 | 1/2004 | Rozenblit et al. |
| 2004/0081248 A1 | 4/2004 | Parolari |
| 2004/0174429 A1 | 9/2004 | Chu |
| 2004/0176049 A1 | 9/2004 | Nagode et al. |
| 2004/0196923 A1 | 10/2004 | Feher |
| 2004/0203377 A1 | 10/2004 | Eaton et al. |
| 2004/0203715 A1 | 10/2004 | Camp, Jr. |
| 2004/0204202 A1 | 10/2004 | Shimamura et al. |
| 2004/0208243 A1 | 10/2004 | Feher |
| 2004/0249925 A1 | 12/2004 | Jeon et al. |
| 2004/0253955 A1 | 12/2004 | Love et al. |
| 2004/0264583 A1 | 12/2004 | Ahmed |
| 2005/0018790 A1 | 1/2005 | Liu |
| 2005/0068918 A1 | 3/2005 | Mantravadi et al. |
| 2005/0090266 A1 | 4/2005 | Sheynblat |
| 2005/0093584 A1 | 5/2005 | Meacham |
| 2005/0094589 A1 | 5/2005 | Camp, Jr. |
| 2005/0097595 A1 | 5/2005 | Lipsanen et al. |
| 2005/0175116 A1 | 8/2005 | Feher |
| 2005/0181810 A1 | 8/2005 | Camp, Jr. |
| 2005/0185699 A1 | 8/2005 | Feher |
| 2005/0185700 A1 | 8/2005 | Pietila et al. |
| 2005/0202809 A1 | 9/2005 | Lappetelainen et al. |
| 2005/0226340 A1 | 10/2005 | Ahmed |
| 2005/0232135 A1 | 10/2005 | Mukai et al. |
| 2005/0250531 A1 | 11/2005 | Takebe et al. |
| 2005/0255826 A1 | 11/2005 | Wittenburg et al. |
| 2005/0275549 A1 | 12/2005 | Barclay et al. |
| 2005/0282588 A1 | 12/2005 | Linjama et al. |
| 2006/0050625 A1 | 3/2006 | Krasner |
| 2006/0057987 A1 | 3/2006 | Nail et al. |
| 2006/0072646 A1 | 4/2006 | Feher |
| 2006/0072647 A1 | 4/2006 | Feher |
| 2006/0072684 A1 | 4/2006 | Feher |
| 2006/0075108 A1 | 4/2006 | Sylvain |
| 2006/0083320 A1 | 4/2006 | Feher |
| 2006/0087432 A1 | 4/2006 | Corbett |
| 2006/0088121 A1 | 4/2006 | Feher |
| 2006/0135183 A1 | 6/2006 | Zavada et al. |
| 2006/0146913 A1 | 7/2006 | Feher |
| 2006/0259942 A1 | 11/2006 | Toyama et al. |
| 2006/0270421 A1 | 11/2006 | Philips et al. |
| 2006/0274838 A1 | 12/2006 | Feher |
| 2006/0293078 A1 | 12/2006 | Qi et al. |
| 2007/0030116 A1 | 2/2007 | Feher |
| 2007/0032220 A1 | 2/2007 | Feher |
| 2007/0032246 A1 | 2/2007 | Feher |
| 2007/0032250 A1 | 2/2007 | Feher |
| 2007/0032266 A1 | 2/2007 | Feher |
| 2007/0032832 A1 | 2/2007 | Feher |
| 2007/0036203 A1 | 2/2007 | Feher |
| 2007/0053471 A1 | 3/2007 | Feher |
| 2007/0053472 A1 | 3/2007 | Feher |
| 2007/0171852 A1 | 7/2007 | George et al. |
| 2007/0171874 A1 | 7/2007 | Tanaka |
| 2007/0202890 A1 | 8/2007 | Feher |
| 2007/0265018 A1 | 11/2007 | Feher |
| 2008/0031126 A1 | 2/2008 | Feher |
| 2008/0031310 A1 | 2/2008 | Feher |
| 2008/0034409 A1 | 2/2008 | O'Rourke et al. |
| 2008/0043868 A1 | 2/2008 | Feher |
| 2008/0056399 A1 | 3/2008 | Feher |
| 2008/0057886 A1 | 3/2008 | Feher |
| 2008/0062856 A1 | 3/2008 | Feher |
| 2008/0120673 A1 | 5/2008 | Dong et al. |
| 2008/0161043 A1 | 7/2008 | Feher |
| 2008/0181151 A1 | 7/2008 | Feher |

(56) References Cited

U.S. PATENT DOCUMENTS

| | | |
|---|---|---|
| 2008/0188240 A1 | 8/2008 | Feher |
| 2008/0205535 A1 | 8/2008 | Feher |
| 2008/0212656 A1 | 9/2008 | Feher |
| 2008/0214164 A1 | 9/2008 | Feher |
| 2008/0219362 A1 | 9/2008 | Feher |
| 2008/0219385 A1 | 9/2008 | Feher |
| 2008/0240070 A1 | 10/2008 | Feher |
| 2008/0253275 A1 | 10/2008 | Feher |
| 2008/0253353 A1 | 10/2008 | Feher |
| 2008/0281585 A1 | 11/2008 | Feher |
| 2009/0061852 A1 | 3/2009 | Feher |
| 2009/0066667 A1 | 3/2009 | Feher |
| 2009/0076803 A1 | 3/2009 | Feher |
| 2009/0092114 A1 | 4/2009 | Feher |
| 2009/0098852 A1 | 4/2009 | Feher |
| 2009/0181640 A1 | 7/2009 | Jones |
| 2009/0240308 A1 | 9/2009 | Feher |
| 2009/0247187 A1 | 10/2009 | Feher |
| 2009/0270113 A1 | 10/2009 | Feher |
| 2009/0310591 A1 | 12/2009 | Feher |
| 2010/0007711 A1 | 1/2010 | Bell |
| 2010/0029284 A1 | 2/2010 | Feher |
| 2010/0064025 A1 | 3/2010 | Nelimarkka et al. |
| 2010/0067595 A1 | 3/2010 | Feher |
| 2010/0124920 A1 | 5/2010 | Feher |
| 2010/0208852 A1 | 8/2010 | Feher |
| 2011/0277000 A1 | 11/2011 | Feher |

FOREIGN PATENT DOCUMENTS

| | | |
|---|---|---|
| DE | 212005000081 | 3/2008 |
| EP | 0915586 A1 * | 12/1999 |
| JP | 5020493 | 1/2005 |
| JP | 5086581 | 3/2005 |
| JP | 8523857 | 1/2008 |
| KE | K 344 | 9/2009 |
| KR | 7002382 | 1/2008 |
| MX | MX/a/2008/001123 | 1/2008 |
| NZ | 565452 | 1/2008 |
| RU | 2008107948 | 10/2005 |
| SG | 200800527-4 | 10/2005 |
| WO | WO 95/23485 | 8/1995 |
| WO | PCT/IB97/00068 | 8/1997 |
| WO | WO 99/09721 | 2/1999 |
| WO | PCT/US99/17995 | 8/1999 |
| WO | PCT/US99/19909 | 8/1999 |
| WO | PCT/US05/35931 | 10/2005 |
| WO | 6000486 | 1/2006 |
| ZA | 2008/00922 | 12/2008 |

OTHER PUBLICATIONS

US pat Publication No. not known U.S. Appl. No. 09/370,360 Feher, K. (SPECT), filed Aug. 9, 1999.
US pat Publication No. not known U.S. Appl. No. 09/370,361 Feher, K. (SYST), filed Aug. 9, 1999.
US pat Publication No. not known U.S. Appl. No. 09/370,362 Feher, K. (BRA), filed Aug. 9, 1999.
US pat Publication No. not known U.S. Appl. No. 09/385,693 Feher, K. (FEHK), filed Aug. 10, 1999.
US pat Publication No. not known U.S. Appl. No. 60/095,943 Feher, K., filed Aug. 10, 1999.
US pat Publication No. not known U.S. Appl. No. 60/098,612 Feher, K., filed Aug. 31, 1998.
US pat Publication No. not known U.S. Appl. No. 60/615,678 Feher, K., filed Oct. 5, 2004.
US pat Publication No. not known U.S. Appl. No. 90/007,687 Feher, K. reexamination of application of US Pat. 6,470,055, filed Aug. 22, 2005.
US pat Publication No. not known Feher, K. U.S. Appl. No. 60/831,512, filed Jul. 18, 2006.
US pat Publication No. not known U.S. Appl. No. 11/927,686 Feher, K.(POLAR), filed Oct. 30 2007.
US pat Publication No. not known U.S. Appl. No. 11/930,159 Feher, K.(DETECT), filed Oct. 31, 2007
US pat Publication No. not known U.S. Appl. No. 11/937,467 Feher, K.(QAMGM), filed Nov. 8, 2007.
US pat Publication No. not known U.S. Appl. No. 12/753,802 Feher, K.(ACMIMO), filed Apr. 2, 2010.
U.S. Appl. No. 12/960,534, filed Dec. 5, 2010, Feher, K. (3GWIFI).
U.S. Appl. No. 13/020,513, filed Feb. 3, 2011, Feher, K. (ACMIMO).
U.S. Appl. No. 13/040,188, filed Mar. 3, 2011, Feher, K. (CELTV).
U.S. Appl. No. 13/097,878, filed Apr. 29, 2011, Feher, K. (WEBMOB).
U.S. Appl. No. 13/098,834, filed May 2, 2011, Feher, K. (MOBITV).
U.S. Appl. No. 13/179,545, filed Jul. 10, 2011, Feher, K. (TVMOBINT).
U.S. Appl. No. 13/282,461, filed Oct. 27, 2011, Feher, K. (QAMGMSKM).
U.S. Appl. No. 13/287,124, filed Nov. 1, 2011, Feher, K. WIRD43G.
U.S. Appl. No. 13/350,775, filed Jan. 15, 2012, Feher, K. INFRARM.
U.S. Appl. No. 13/351,197, filed Jan. 16, 2012, Feher, K. SATCEL.
U.S. Appl. No. 13/360,666, filed Jan. 28, 2012, Feher, K. TVINTERN.
U.S. Appl. No. 13/473,282, filed May 16, 2012, Feher, K. UMTS.
U.S. Appl. No. 13/475,965, filed May 19, 2012, Feher, K. SATAISHTR.
U.S. Appl. No. 13/492,273, filed Jun. 8, 2012, Feher, K. DIGTV-SHIP.
U.S. Appl. No. 13/552,629, filed Jul. 18, 2012, Feher, K. SHIPCELSAT.
U.S. Appl. No. 13/602,286, filed Sep. 3, 2012, QAMCDTDMA Feher, K.
3GPP TS 25.213 V6.0.0 (Dec. 2003) $3^{rd}$ Generation Partnership Project ; Technical Specification Group Radio Access Network Spreading and Modulation (FDD) (Release 6) 29 pages.
3GPP TS 05.04 V8.4.0 (Nov. 2001) Technical Specification Group GSM/EDGE Radio Access Network; Digital cellular telecommunications system (Phase 2+); Modulation (Release1999); 3GPP:$3^{rd}$ Generation Partnership Project; (10 pages).
Brown, C., Feher, K: "A reconfigurable modem for increased network capacity and video, voice, and data transmission over GSM PCS", IEEE Transactions on Circuits and Systems for Video Technology, pp. 215-224; vol. 6 , No. 2, Apr. 1996 (10pages).
Brown, C.W.:"New Modulation and Digital Synchronization Techniques for Higher Capacity Mobile and Personal Communications Systems" Ph.D. Thesis University of California, Davis, Nov. 1996 pp: i-vii;138-190; 269-272; 288-289;291.
Brown, C., Feher, K. : "A Flexible Modem Structure for Increased Network Capacity and Multimedia Transmission in GSM PCS", Proceedings of the Fifteenths Annual Joint Conference of the IEEE Computer and Communication Societies (INFOCOM '96), 1996 (8 pages).
Furuscar, A. et al .: "EDGE: Enhanced Data Rates for GSM and TDMA /136 Evolution" IEEE Personal Communications , Jun. 1999 , pp. 56-66.
Qualcomm : "MSM 6275 Chipset Solution", Qualcomm CDMA Technologies, San Diego, CA, 2004 (8 pages). Copyright 2004 Qualcomm.
Qualcomm : "MSM 6300 Chipset Solution", Qualcomm CDMA Technologies, San Diego, CA, 2004 (8 pages). Copyright 2004 Qualcomm.
Baisa , N. "Designing wireless interfaces for patient monitoring equipment", RF Design Magazine Apr. 2005, www.rfdesign.com (5 pages).
Hickling, R.M.: "New technology facilitates true software—defined radio" RF Design Magazine Apr. 2005, www.rfdesign.com (5 pages).
Feher, K.: "Wireless Digital Communications: Modulation & Spread Spectrum Applications", Prentice Hall, Upper Saddle River, NJ 07458, Copyright 1995, Book ISBN No. 0-13-098617-8 (pages: front page; copyright page; pp. 164-177; 461-471; and 475-483).
Holma, H., Toskala, A.: "WCDMA for UMTS Radio Access for Third Generation Mobile Communications", Second Edition, John Wiley & Sons Ltd. Chichester, West Sussex, England , Copyright 2002 , ISBN 0-470-84467-1 (pages: front page;copyright page; pp. xv-xvi; 1-4; 90-95; 199-201; and 235-236).

(56) References Cited

OTHER PUBLICATIONS

Tuttlebee, W. :"Software Defined Radio: Baseband Technology for 3G Handsets and Basestations", John Wiley & Sons, Ltd., Chichester, West Sussex, England, Copyright 2004 , ISBN 0-470-86770-1 (pages: front page; copyright page; pp. 1-3; 8-15; 34-39; and 274-279).

Dobkin,D.M. and Wandinger, T.: "A Radio Oriented Introduction to Radio Frequency Identification"—RFID Tutorial , High Frequency Electronics, Jun. 2005 , Copyright 2005 Summit Technical Media (6 pages).

Dale Setlak : "Fingerprint sensors in Wireless handsets" a presentation at the EOEM Design Expo Jun. 22, 2005, Wireless OEM Design Expo Online Conference & Exhibition , http://www.reedbusinessinteractive.com/eoem/index.asp (38 pages).

Kato, S. and Feher, K.: "XPSK: A new cross-correlated phase shift keying modulation technique", IEEE Trans. Commun., vol. COM-31, No. 5, May 1983, (pp. 701-707).

Perrott et al.,: "A 27-mW CMOS Fractional-N Synthesizer Using Digital Compensation for 2.5-Mb/s GFSK Modulation", IEEE Journal of Solid-State Circuits, Vo.32, No. 12, Dec. 1997, (pp. 2048-2060 ).

Jian et al.,: "An Efficient IF Architecture for Dual-Mode GSM/W-CDMA Receiver of a Software Radio," . . . 1999 International Workshop on Mobile Multimedia Communications, IEEE, Nov. 15-17, 1999 San Diego ,CA(pp. 21-24).

Mangold et al.,: Software-definable Implementation of a Dual Mode TD-CDMA/DCS 1800 Transceiver Communication Summit, vol. 1, Jun. 1998, ( 5 pages).

Morrison, I. S. "ACE-8PSK: Band-Limited 8PSK With an Almost Constant Envelope", Tenth International Conference on Digital Satellite Communications, May 15-19, 1995, Brighton, UK. (pp. 325-331).

Hyunchol Shin: "GSM RF Transmitter Design", Kewangwoon University, Seoul, Korea. Presented at PERC, ICU Aug. 19, 2004 (40 slides).

Grieco, D.M. & Schilling, D.L.: "The Capacity of Broadband CDMA Overlaying a GSM Cellular System", IEEE Vehicular Technology Conference, Jun. 8-10, 1994, Stockholm, Sweden , 1994 IEEE (pp. 31-35).

Malkemes et al.,: "An Interoperable PACS and DCS1900 Subsciber Unit Radio Architecture", Sixth IEEE International Symposium, PIMRC'95: Personal Indoor and Mobile Radio Communication, Sep. 27-29, 1995, Toronto, Ont. Canada, 1995 IEEE (pp. 1149-1154).

Bitkom: "RFID White Paper Technology, Systems, and Applications", Bitkom German Association for Information Technology, German Version published Aug. 2005, and English Version published Dec. 2005. The English Version published Dec. 2005 has been used in Applicant's search.

Nokia: Nokia 5140i phone; Nokia 5140i NFC Shell User Guide Issue 1.0, May 4, 2006; Nokia 6131 NFC User Guide in English"Issue 1, Feb. 6, 2007; Nokia Field Force Solution is an easy-to-use, flexible management tool especially designed to help enterprise improve their mobile and field-based business operations" Copyright 2007.

Quorum articles and publications downloaded from www.quorumsystems.com on Jun. 24, 2007, including: Why Convergence? The Sereno Platform. Sereno QS1000, QS 2000 and QS 3000, Copyright 2006 Quorum.

Kellerer, W. et al. "A communication gateway for infrastructure-independent 4G wireless access", this paper appears in: Communications Magazine, IEEE Publication Date: Mar. 2002 vol. 40, Issue: 3 pp. 126-131.

Spiegel, S.J. and Kovacs, I.G. "An efficient integration of GPS and WCDMA radio front-ends", IEEE Transactions on Microwave Theory and Techniques, vol. 52, Issue 4, Apr. 2004 pp. 1125-1131.

Walker, H.R. : "Understanding Ultra Narrowband Modulation" from Microwaves and RF Dec. 1, 2003 downloaded from: http://www.highbeam.com/doc/1P3-523237701.html.

\* cited by examiner

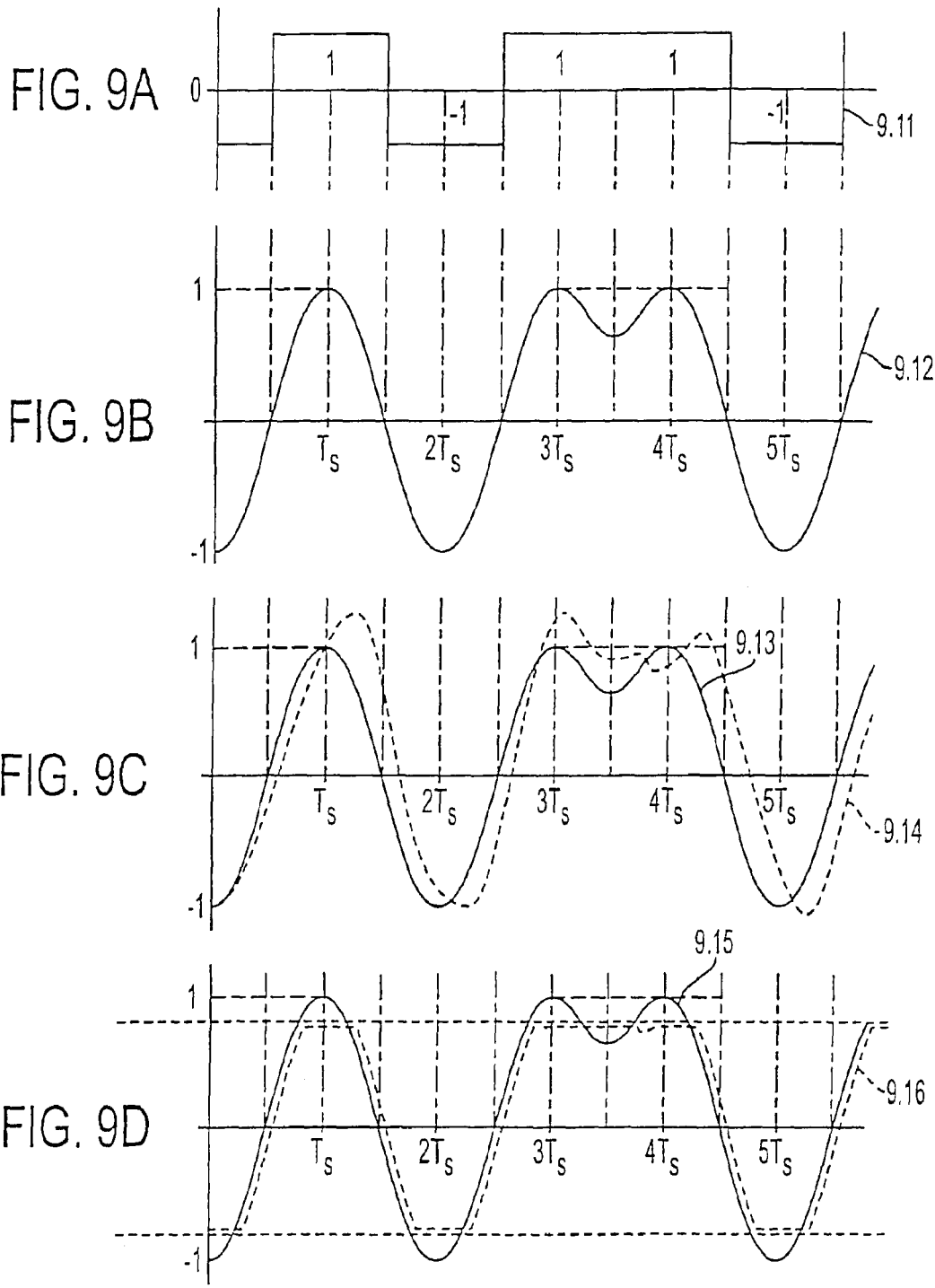

FQPSK MEAS. MIN. FILT. A=0.7

FGMSK (BTb=0.3)

FQPSK COMPUTER. GENER.
A=0.7, NO POST TCS FILTERING

FQPSK-B MEAS.

FQPSK-B. VECTOR CONSTELLATION

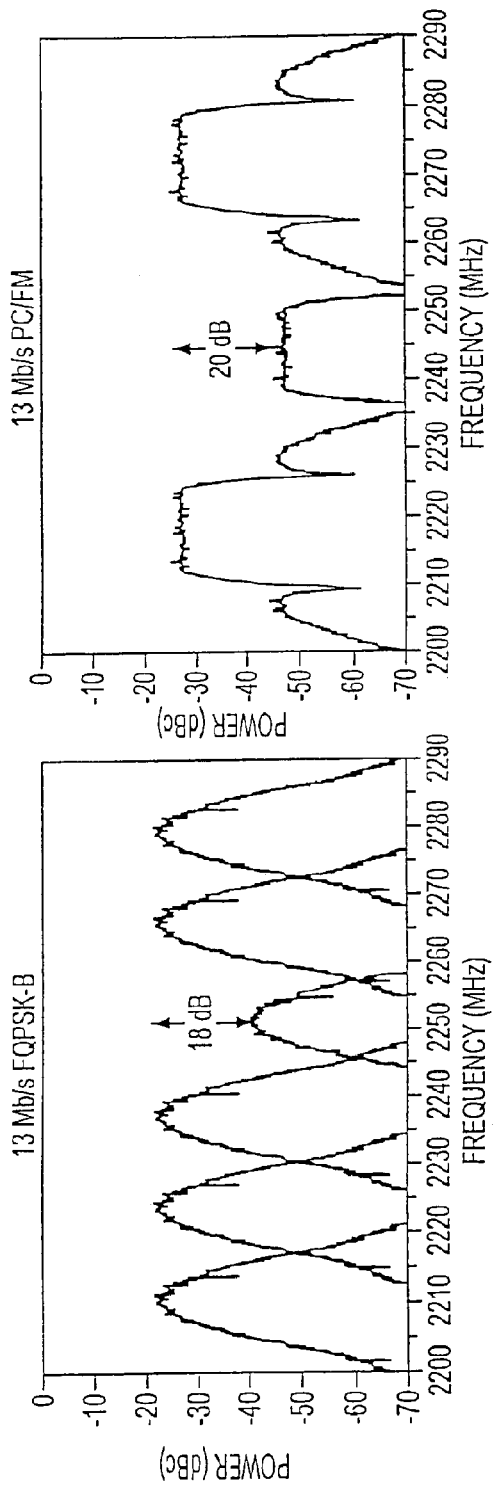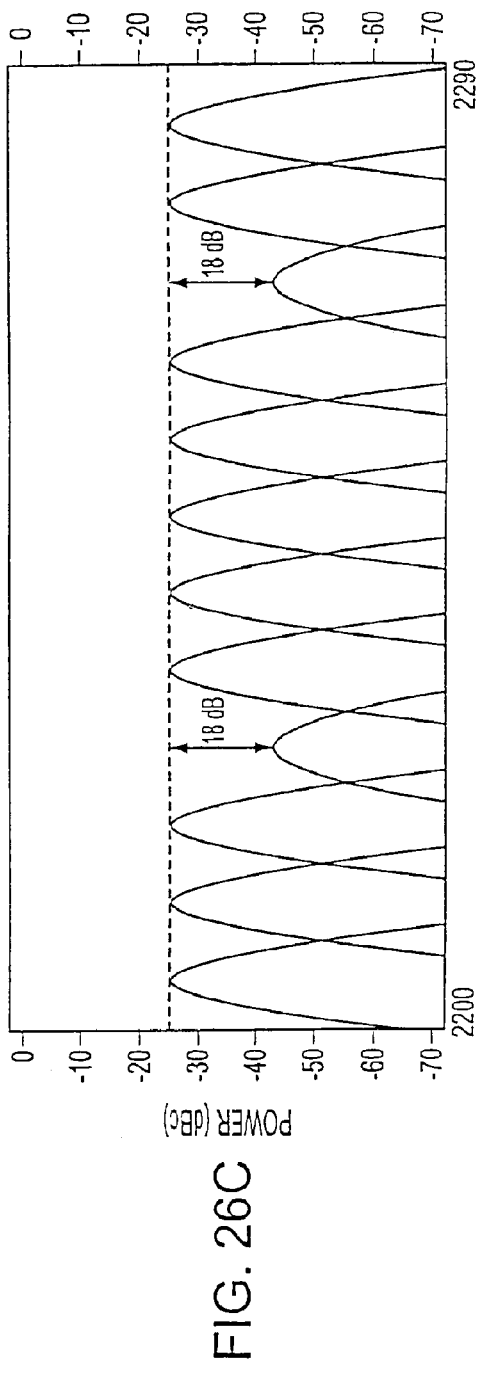
FIG. 26A
FIG. 26B
FIG. 26C

QAM CDMA AND TDMA COMMUNICATION METHODS

RELATED APPLICATIONS

This application is a Continuation Application of U.S. patent application Ser. No. 13/282,461, filed on Oct. 27, 2011 and of U.S. patent application Ser. No. 11/937,467 and now U.S. Pat. No. 8,050,345 and is a Continuation Application of U.S. patent application Ser. No. 10/831,724, filed on Apr. 24, 2004, now U.S. Pat. No. 7,593,481 which is a continuation Application of U.S. patent application Ser. No. 09/370,362, filed on Aug. 9, 1999, now U.S. Pat. No. 6,757,334 and claims the benefit of the aforementioned applications. Related patent applications, issued patents and other publications and references are also incorporated herein as listed in the Attached Supplemental Information Disclosure (SID) and attached to the SID.

This application claims the benefit under 35 U.S.C. 119(e) of U.S. Provisional Patent Application Ser. No. 60/095,943 entitled "FQPSK TRANSCEIVERS" filed 10 Aug. 1998 [PP3]; and incorporated herein by reference.

Other related U.S. patent applications are co-pending U.S. Utility patent application Ser. No. 09/111,723 [PP1] filed 8 Jul. 1998 and entitled "FMOD TRANSCEIVERS INCLUDING CONTINUOUS AND BURST OPERATED TDMA, FDMA, SPREAD SPECTRUM CDMA, WCDMA AND CSMA"; U.S. Provisional Patent Application Ser. No. 60/098,612 [PP2] entitled "FK MODULATION AND TRANSCEIVERS INCLUDING CLOCK SHAPING PROCESSORS" filed 31 Aug. 1998; each of which is hereby incorporated by reference.

In this continuation application, Applicant corrected certain typographical errors which were noticed by Applicant in the parent patent applications.

FIELD OF THE INVENTION

This invention relates generally to Bit Rate Agile (BRA) signal processors; more particularly to cross-correlated signal processors for increasing RF spectral and power efficiency of modulated transmitted signals including but not limited to digital binary, digital multilevel, and/or analog modulated signals operated in linearized and in power-efficient Non-Linearly Amplified (NLA) systems; and most particularly to BRA and RF Agile Cascaded Time Constrained Signal (TCS) response and Long Response (LR) filtered and Mis-Matched (MM) filtered (ACM) quadrature phase, frequency and amplitude modulated Transmitter, Receiver, and Transceiver systems having these characteristics and methods and procedures provided thereby.

BACKGROUND OF THE INVENTION

The most important objectives of wireless communications, broadcasting, telemetry, infrared and in general "radio" systems as well as "wired" systems include: power and bandwidth or spectrum efficiency combined with robust Bit Error Rate (BER) performance in a noisy and/or strong interference environment. These system objectives are specified in numerous systems including wireless communications and cellular systems, satellite systems, mobile and telemetry systems, broadcasting systems, cable, fiber optics and practically all communication transmission systems. A partial list of publications, references, and patents are provided separately below. The cited publications, references [1-23] and patents [P1-P8], and the references within the aforementioned publications contain definitions and descriptions of many terms used in this new patent disclosure and for this reason these conventional terms and definitions will be described only briefly, and highlighted on a case by case basis.

Robust or high performance Bit Error Rate (BER) specifications and/or objectives are frequently expressed in terms of the required BER as a function of Energy per Bit (Eb) divided by Noise Density or simply noise (No), that is, by the BER=f (Eb/No) expression. Low cost, reduced size, and compatibility and/or interoperability with other conventional or previously standardized systems, also known as "legacy systems," are highly desired. Several standardization organizations have adopted modulation techniques such as conventional Binary Phase Shift Keying (BPSK), Quadrature Phase Shift Keying (QPSK), Offset Quadrature Phase Shift Keying (OQPSK) also designated as Staggered Quadrature Phase Shift Keying (SQPSK), and pi/4-QPSK (or $\pi/4$-QPSK) techniques including differential encoding variations of the same. See publications [1-23] and referenced patents [P1-P8] for examples and further description. For spectrally or spectrum efficient signaling (such as band-limited signaling), these conventional methods exhibit a large envelope fluctuation of the modulated signal, and thus have a large increase in peak radiated power relative to the average radiated power. For these reasons such systems are not suitable for BRA, robust BER performance NLA operated RF power efficient systems.

Within the present state of the technology, for numerous BRA Transceiver applications, it is not practical to introduce band-pass filtering after the NLA power efficient Radio Frequency (RF) final amplifier stage. Here we are using the term "Radio Frequency" (RF) in its broadest sense, implying that we are dealing with a modulated signal. The RF could be, for example, as high as the frequency of infrared or fiber optic transmitters; it could be in the GHz range, for example, between 1 GHz and 300 GHz or more, or it could be in the MHz range, for example, between about 1 MHz and 999 MHz, or just in the kHz range. The term RF could even apply to Quadrature Modulated (abbreviated "QM" or "QMOD") Base-Band (BB) signals or to Intermediate Frequency (IF) signals.

In conventional BPSK, QPSK, OQPSK or SQPSK, and differentially-encoded phase-shift keying systems variants of these systems, such as DBPSK and DQPSK, as well as in pi/4-DQPSK and trellis coded QPSK and DQPSK, large envelope fluctuations require linearized (LIN) or highly linear transmitters including frequency up-converters and RF power amplifiers and may require expensive linear receivers having linear Automatic Gain Control (AGC) circuits. A transmitter NLA reduces the time domain envelope fluctuation of conventional QPSK type of band-limited signals and this reduction of the envelope fluctuation, being a signal distortion, is the cause of spectral restoration or spectral regrowth and the cause of unacceptably high levels of out-of-band spectral energy transmission, also known as out-of-band interference. Additionally, for conventional BPSK, QPSK, and also Quadrature Amplitude Modulation number (QAM) signals, undesired in-phase channel (I) to quadrature channel (Q) crosstalk is generated. This crosstalk degrades the BER=f $(E_b/N_0)$ performance of the modulated radio transmitter.

Experimental work, computer simulation, and theory documented in many recent publications indicates that for band-limited and standardized BPSK, QPSK, OQPSK or SQPSK or pi/4-QPSK, and QAM system specifications, very linear amplifiers are required to avoid the pitfalls of spectral restoration and of BER degradation. Linearized or linear amplifiers are less RF power efficient (during the power "on" state, power efficiency being defined as the transmit RF power divided by DC power), are considerably more expensive and/or having less transmit RF power capability, are larger in size, and are not as readily available as NLA amplifiers. The advantages of NLA over LIN amplifiers are even more dramatic at higher RF frequencies, such as frequencies above about 1 GHz for applications requiring low dc voltage, for example applications or systems operating on size "AA" batteries having only 1.5 Volt dc and for high RF modulated power requirements, for example transmit RF power in the 0.5 Watt to 100 Watt range.

Published references [P1 to P8] and [1 to 23] include additional background information. These references include descriptions of binary-state and multiple-state Transmitter/Receiver (Transceiver) or for short ("TR") systems that are suitable for NLA. In the aforementioned references Processors, Modems, Transmitters, Receivers and Transceivers, suitable for NLA, have been described, defined and designated as first generation of Feher patented Quadrature Shift Keying (FQPSK). For example, in reference [22] published on May 15, 1999 the authors Drs. M. K. Simon and T. Y. Yan of JPL/NASA-Caltech present a detailed study of Unfiltered Feher-Patented Quadrature Phase Shift Keying (FQPSK). In references [1-22] and patents #[P1-P8] numerous first generation FQPSK technology based terms, and terms other than the FQPSK abbreviation/acronym have been used. In addition to FQPSK Transceivers, these first generation of systems have been also described and/or defined as: Feher's Minimum Shift Keying (FMSK), Feher's Frequency Shift Keying (FFSK), Feher's Gaussian Minimum Shift Keying (FGMSK), Feher's Quadrature Amplitude Modulation (FQAM) and/or Feher's (F) Modulation/Amplification (FMOD). Additionally terms such as Superposed Quadrature Amplitude Modulation (SQAM), Intersymbol Interference and Jitter Free (IJF) and/or IJF-OQPSK have been also described in Feher et al.'s prior patents and publications, each of which is incorporated by reference.

In the cited patents and other references, among the aforementioned abbreviations, acronyms, designation, terms and descriptions the "FQPSK" abbreviation/term has been most frequently used to describe in most generic terms one or more of these afore described Feher or Feher et al. first generation of Non-Linearly Amplified (NLA) inventions and technologies. The $1^{st}$ generation of FQPSK systems have significantly increased spectral efficiency and enhanced end-to-end performance as compared to other NLA systems. RF power advantages, robust BER performance, and NLA narrow spectrum without the pitfalls of conventional BPSK and DBPSK, QPSK and OQPSK have been attained with these $1^{st}$ generation FQPSK systems and methods. The generic $1^{st}$ generation terms such as FQPSK, as well as other previously mentioned terms/acronyms are retained and used in this description to describe the new BRA, Code Selectable (CS), Modem Format Selectable (MFS) and modulation-demodulation Mis-Matched (MM) filtered architectures and embodiments of "$2^{nd}$ generation" FQPSK Transceivers.

While these earlier issued patents and publications describe material of a background nature, they do not disclose the original new enhanced performance bit rate agile and modulation agile/selectable technologies disclosed in this new invention.

PARTIAL LIST OF RELEVANT LITERATURE

Several references, including U.S. patents, International or Foreign Patents, publications, conferences proceedings, and other references are identified herein to assist the reader in understanding the context in which the invention is made, some of the distinctions of the inventive structures and methods over that which was known prior to the invention, and advantages over the invention. No representation is made as to whether the contents of the cited references represent prior-art as several of the cited references have a date after the effective filing date (priority date) of this patent application. This list is intended to be illustrative rather than exhaustive.

United States Patents

[P1] U.S. Pat. No. 5,784,402 Issued July 1998 to Feher
[P2] U.S. Pat. No. 5,491,457 Issued February 1996 to Feher
[P3] U.S. Pat. No. 4,720,839 Issued January 1988 to Feher et al.
[P4] U.S. Pat. No. 4,644,565 Issued February 1987 to Seo/Feher
[P5] U.S. Pat. No. 4,567,602 Issued January 1986 to Kato/Feher
[P6] U.S. Pat. No. 4,350,379 Issued September 1982 to Feher
[P7] U.S. Pat. No. 4,339,724 Issued July 1982 to Feher
[P8] U.S. Pat. No. 3,954,926 Issued March 1976 to Feher Foreign Patent Documents

[PF1] Canadian Patent No. 1130871 August 1982
[PF2] Canadian Patent No. 1211517 September 1986
[PF3] Canadian Patent No. 1265851 February 1990

Other Publications

1. Feher, K.: *Wireless Digital Communications: Modulation Spread Spectrum*. Prentice Hall, 1995.
2. Feher, K.: *Digital Communications: Satellite/Earth Station Engineering*. Prentice Hall, 1983. Available from Crestone Engineering—Noble Publishing, 2245 Dillard Street, Tucker, Ga. 30084.
3. Feher, K.: *Advanced Digital Communications: Systems and Signal Processing*. Prentice Hall, 1987. Available from Crestone Engineering—Noble Publishing, 2245 Dillard Street, Tucker, Ga. 30084.
4. Feher, K.: *Digital Communications: Microwave Applications*. Prentice Hall 1981. Since 1997 available from Crestone Engineering—Noble Publishing, 2245 Dillard Street, Tucker, Ga. 30084.
5. Feher, K. and Engineers of Hewlett-Packard: *Telecommunications Measurements, Analysis, and Instrumentation*: Prentice Hall 1987. Since 1997 reprints have been available from Crestone Engineering—Noble Publishing, 2245 Dillard Street, Tucker, Ga. 30084.
6. Feher, K., Emmenegger, H.: "FQPSK Use for Electronic News Gathering (ENG), Telemetry and Broadcasting," *Proc. of the National Association of Broadcasters* NAB'99 Broadcast Engineering Conference, Las Vegas, Apr. 19-22, 1999.
7. Feher, K.: "FQPSK Doubles Spectral Efficiency of Operational Systems: Advances, Applications, Laboratory and Initial Air-to-Ground Flight Tests" (Date of Submission: Aug. 14, 1998). *Proc. of the International Telemetry Conference*, ITC-98 ITC/USA 98, San Diego, Calif., Oct. 26-29, 1998.
8. W. Gao, S. H. Wang, K. Feher: "Blind Equalization for FQPSK and FQAM Systems in Multipath Frequency Selective Fading Channels," *Proc. Internat. Telemetry Conf.* ITC/USA'99, Oct. 25-28, 1999, Las Vegas, Nev.

9. Terziev, G., Feher, K.: "Adaptive Fast Blind Feher Equalizers (FE) for FQPSK," *Proc. Of the International Telemetry Conference* ITC/USA'99, Oct. 25-28, 1999, Las Vegas, Nev.
10. Feher, K.: "FQPSK Transceivers Double the Spectral Efficiency of Wireless and Telemetry Systems"*Applied Microwave & Wireless Journal*, June 1998.
11. Seo, J-S. and K. Feher: "Bandwidth Compressive 16-State SQAM Modems through Saturated Amplifiers," *IEEE Radio Commun., ICC '86*, Toronto, June 1986.
12. Kato, S. and K. Feher: "XPSK: A new cross-correlated PSK," *IEEE Trans. Com.*, May 1983.
13. Law, E. L., U.S. Navy: "Robust Bandwidth Efficient Modulation" *European Telemetry Conference*, ETC-98, Germany, May 1998.
14. Feher, K.: "FQPSK Doubles the Spectral Efficiency. of Operational Telemetry Systems," *European Telemetry Conference, ETC*-98, May 1998, Germany.
15. Do, G. and K. Feher: "FQPSK-GMSK: Wireless System Tests an ACI Environment," *Proc. of Wireless Symposium*, Santa Clara, Calif., Feb. 9-13, 1998.
16. Law, E. and K. Feher: "FQPSK versus PCM/FM for Aeronautical Telemetry Applications: Spectral Occupancy and Bit Error Probability Comparisons" *Proc. of ITC*-97, Las Vegas, October 1997.
17. Feher, K "FQPSK Doubles Spectral Efficiency of Telemetry: Advances and Initial Air to Ground Flight Tests," ITC/USA 98, *Proc. of the Internat. Telemetry Conference*, San Diego, October 1998.
18. Law, E. and K. Feher: "FQPSK versus PCM/FM for Aeronautical Telemetry Applications; Spectral Occupancy and Bit Error Probability Comparisons," *Proc. of the Internat. Telemetry Conf.*, Las Vegas, Nev., Oct. 27-30, 1997.
19. Martin, W. L., T-Y. Yan, L. V. Lam: "Efficient Modulation Study at NASA/JPL," *Proc. of the Tracking, Telemetry & Command Systems Conference*, European Space Agency (ESA), June 1998.
20. Law, E. L., ITC-98 Session Chair: "RCC Alternate Standards and IRIG106 update," Briefings by DoD during ITC/USA 98 *Internat. Telemetry Conference*, San Diego, October 1998.
21. K. Feher: "FQPSK Doubles Spectral Efficiency of Operational Systems: Advances, Applications, Laboratory and Initial Air to Ground Flight Tests", File: ITC.98. Final Paper. Rev. 5. Aug. 14, 1998 (Date of Submission) for publication in the *Proc. of the International Telemetry Conference*, ITC-98; San Diego, Oct. 26-29, 1998
22. Simon, M. K, Yan, T. Y. "Performance Evaluation and Interpretation of Unfiltered Feher-Patented Quadrature Phase-Shift Keying (FQPSK)," California Institute of Technology, JPL-NASA publication, *TMD Progress Report* 42-137, Pasadena, Calif., May 15, 1999.
23. Winters, J. H.: "Adaptive Antenna Arrays for Wireless Systems," *Tutorial Notes presented/distributed at the* 1999 *IEEE Vehicular Technology Conference*, Houston, Tex., May 16, 1999.

SUMMARY OF THE INVENTION

This invention includes disclosure of new and/original spectral efficient and RF power efficient-high performance technologies, new architectures, embodiments and new Bit Rate Agile (BRA) implementation of $2^{nd}$ generation FQPSK Transceivers. These inventive structures, methods, and technologies are suitable for a large class of implementations and applications. Numerous embodiments of the inventive structures and methods are enabled. These include cost effective solutions for BRA, Modulation and Demodulation (Modem) Format Selectable (MFS) and Coding Selectable (CS) processors, modulators/demodulators, Transceivers, having agile/tunable RF frequency embodiments and are suitable for power efficient NLA systems.

The terms abbreviations and descriptions used in the $1^{st}$ generation of Feher et. al inventions, highlighted in the "Background of the Invention" section, as well as other previously identified terms/acronyms and abbreviation and in particular FQPSK and related terms, used in the cited references, are retained and/or slightly modified and are used relative to this disclosure of the new invention to describe second generation "$2^{nd}$ generation" BRA architectures and embodiments of FQPSK, FGMSK and FQAM Transceivers. This disclosure contains embodiments for further significant spectral savings and performance enhancements, and new functions and architectures, which were not, included in the referenced prior art patents, inventions and publications.

BRA or "Bit Rate Agile" abbreviation and term describes technologies, implementations, embodiments suitable for design, use and applications in which the information rate, source rate, or the often used alternative terms "bit rate", "symbol rate", or "data rate" may be selectable or programmable by the user or by one or more control signal(s). Bit Rate Agile (BRA) systems may be programmable by software or have predetermined or "selectable," i.e., "agile" bit rate applications. The term "bit rate agility" refers to variable and/or flexible selectable bit rates (again bit rate, symbol rate, data rate, information rate, source rate, or equivalent); the bit rates could be selected on a continuous fashion in small increments and/or in steps. These systems are designated as BRA (or Bit Rate Agile) systems. BRA, MFS, and CS systems requirements are increasing at a rapid rate.

Changeable (or variable, or selectable) amounts of cross-correlation between Time Constrained Signal (TCS) response processors and/or combined TCS and Long Response (LR) processor and/or post processor filters of in-phase (I) and quadrature (Q) phase signals of BRA Transceivers, MFS and CS baseband signal processing implementations and architectures for tunable RF frequency embodiments having enhanced spectral efficiency and end-to-end performance are disclosed. These new BRA, MFS and CS classes of FQPSK signal processors, modems and transceivers, with Adaptive Antenna Arrays (AAA) and RF power efficient amplifiers and entire Transceivers, operated in fully saturated or NLA mode, with intentionally Mis-Matched (MM) modulation and demodulation filters, transmit BRA and receive BRA filters/processors, disclosed herein, attain high performance advantages and significant spectral savings.

A changeable amount of cross-correlation between the BRA and MFS Time Constrained Signal (TCS) response processor and/or combined TCS and Long Response (LR) processor and/or post processor filters of the transmitter with selectable MM between the BRA transmitter and BRA receiver and CS processors, including single and separate in-phase (I) and quadrature (Q) signal storage/readout generators and single and/or separate I and Q channel D/A architectures and a bank of switchable filters for cross-correlated BRA, MFS and CS formats are also disclosed.

These new classes of $2^{nd}$ generation of FQPSK signal processors, modems and transceivers, with Adaptive Antenna Arrays (AAA) and RF power efficient amplifiers and entire Transceivers, operated in BRA, MFS and CS fully saturated NLA mode, or with LIN mode with intentionally Miss-Matched (MM) transmit BRA and receive BRA filters/processors, disclosed herein, have robust performance and significant spectral saving advantages.

In addition to digital embodiments, BRA analog cross-correlation implementations and combined digital-analog active and passive processors, for $2^{nd}$ generation FQPSK Transceivers are also disclosed. Subsets, within the generic $2^{nd}$ generation of the FQPSK family of processors, modems and transceivers are also designated as $2^{nd}$ generation BRA Feher's Minimum Shift Keying (FMSK), Feher's Gaussian Minimum Shift Keying (FGMSK), Feher's Frequency Shift Keying (FFSK) and Feher's Quadrature Amplitude Modulation (FQAM).

Switched BRA, selectable Cross-Correlation (CC or Xcor) transmit and receive bandwidth Mis-Matched (MM) low-pass, band-pass and adaptive filter means and controller circuits and algorithms for preamble contained and differentially encoded and/or Forward Error Correction (FEC) with Redundant and Pseudo-Error (PE) based Non Redundant Detection (NED) implementations for FQPSK are also described.

The term "Mis-Matched" (MM) designates an intentional and substantial mis-match (MM) between the bandwidth and/or frequency or phase response of modulator filters and demodulator filters and/or mis-match (MM) between one or more implemented FQPSK filter(s) and the theoretical optimal performance minimum bandwidth Nyquist filters.

The term "Agile Cascaded Mis-Matched" (ACM) designates the BRA and RF agile ("flexible" or "tunable" RF frequency) cascaded TCS response and LR processor/filter(s) which are mis-matched within their respective application and/or use within this invention.

For NLA and for LIN amplifiers, selectable FQPSK filtering strategies in the transmitter and separately in the receiver lead to further spectral efficiency enhancements. Fast synchronization systems and robust efficient adaptive equalizers/adaptive switched systems are also disclosed.

The inventive structure and method includes transmit elements, receive elements, and transmit and receive elements, and may be applied to a variety of communication applications, including, but not limited to, wireless communications and cellular systems, satellite systems, mobile and telemetry systems, broadcasting systems, cable system, fiber optic systems, and more generally to nearly all communication transmission and/or receiving systems.

In one embodiment of the invention, a bit rate agile communication system is provided and includes a splitter receiving an input signal and splitting the input signal into a plurality of baseband signal streams, and a baseband signal processing network receiving the plurality of baseband signal streams and generating cross-correlated cascaded processed and filtered bit rate agile (BRA) in-phase and quadrature-phase baseband signals. In another embodiment, a quadrature modulator receiving and quadrature modulating the cross-correlated filtered in-phase and quadrature-phase baseband signals to generate a quadrature modulated output signal is also provided. In another embodiment, the baseband signal processing network includes a cross-correlator and at least one bit rate agile cascaded mis-matched (ACM) modulator filter.

In yet another embodiment, the invention provides a bit rate agile communication system including a baseband signal processing network receiving parallel baseband signal streams and generating combined Time Constrained Signal (TCS) response and Long Response (LR) filtered in-phase and quadrature-phase baseband signals. In a variation of this embodiment, the inventive structure also includes a quadrature modulator receiving and quadrature modulating the Time Constrained Signal (TCS) response and Long Response (LR) filtered in-phase and quadrature-phase baseband signals to generate a quadrature modulated bit rate agile output signal.

In still another aspect, the invention provides a method for generating bit rate agile signals in a communication system. The method includes the steps of processing a plurality of signal streams to generate cross-correlated signals having changeable amounts of filtering for bit rate agile in-phase and quadrature-phase baseband signals. The inventive method may also include the step of receiving an input signal and converting the input signal into the plurality of signal streams. It may also optionally include the further step of modulating the cross-correlated filtered in-phase and quadrature-phase baseband signals to generate a quadrature modulated bit rate agile output signal.

In yet another aspect, the invention provides a method for generating bit rate agile signals in a signal transmission system, where the method includes the steps of receiving a plurality of signal streams, processing the plurality of signal streams to generate cascaded Time Constrained Signal (TCS) response and Long Response (LR) filtered in-phase and quadrature-phase baseband signals; and modulating the Time Constrained Signal (TCS) response and Long Response (LR) filtered in-phase and quadrature-phase baseband signals to generate a quadrature modulated bit rate agile output signal.

BRIEF DESCRIPTION OF THE DRAWINGS

FIG. 9 illustrates a Non Return to Zero (NRZ) signal pattern, a TCS response pattern, a signal pattern of a TCS filtered by a conventional Low-Pass-Filter (LPF) resulting in cascaded TCS response and Long Response (LR) pulse patterns with some overshoots. In the non-Xcor case as well as in the Cross-Correlated case a Peak Limiter (PL) or gradual Soft Limiter or Xcor Soft Limiter reduces the amplitude peaks. The LR filter extends the TCS response to multiple pulses and may introduce additional spectral saving, however could introduce additional ISI and increased peak variations.

FIG. 26 shows the Power Spectral Density (PSD) of NLA illustrative data links operated at 13 Mb/s rate per link, in the US Government authorized band between 2200 MHz to 2290 MHz. With telemetry standardized filtered PCM/FM 3 links can be used simultaneously, with FQPSK-B the number of links is doubled to 6, while with NLA 16-state FQAM, also designated as a $2^{nd}$ generation multi-state FQPSK or FQPSK.2.4, the number of 13 Mb/s links is quadrupled to 12 links (over that of standardized PCM/FM).

DETAILED DESCRIPTION OF EMBODIMENTS OF THE INVENTION

Figure 1A:
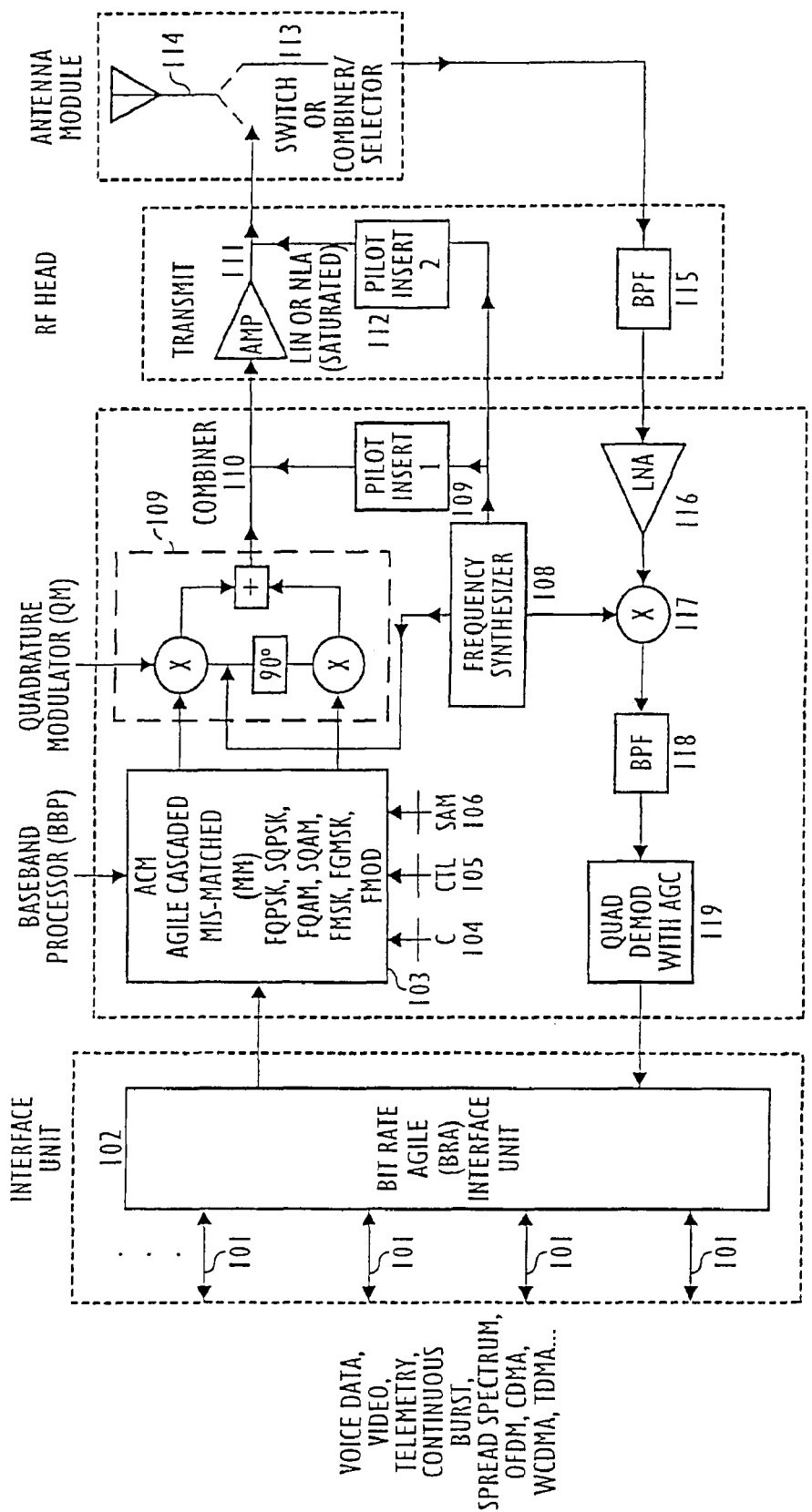
FIG. 1a is a diagram depicting an Agile Cascaded Mis-Matched (ACM) enhanced spectral efficiency, high performance Transmitter/Receiver (Transceiver) block diagram for a generic class of modulated systems.

Introductory Description of Embodiments of the Invention

This invention relates in part to Bit Rate Agile (BRA) signal processors and particularly to cross-correlated (abbreviated "CC" or "Xcor") and to Agile Cascaded Mis-Matched (ACM) signal processors for increasing the RF spectral efficiency and RF power efficiency of modulated transmitted signals including digital binary, and digital multilevel signals, and of analog modulated signals operated in linearized (LIN) and in power efficient Non-Linearly Amplified (NLA) systems. Cross-correlated quadrature phase, frequency, and amplitude modulated Transmitter and Receiver (Transceiver) systems are described. The use of section headings is for convenience only and is not intended to delimit the discussion of particular aspects of the invention as aspects, features, embodiments, advantages, and applications are described through the specification and drawings. Acronyms are used extensively throughout the description to avoid excessively long descriptive phrases. In some instances the same acronym is used for a system component or structure as well as an adjective or other qualifier for the function or operation performed by that structure. The meaning will be clear from the context of the description.

The disclosed BRA systems, designated as belonging to the class of Feher's Quadrature Phase Shift Keying (FQPSK) systems, and also by other acronyms and abbreviations, described herein, include BRA Time Constrained Signal (TCS) response processors and cascaded TCS and BRA Long Response (LR) processors and/or post-processor filters of in-phase (I) and of quadrature (Q) phase signals of BRA transmitters and receivers (or Transceivers when transmitter and receiver are combined). Modulation and demodulation (Modem) Format Selectable (MFS) and Coding Selectable (CS) baseband signal processing implementations and architectures for tunable RF frequency embodiments having Pseudo-Error (PE) based Non-Redundant Error Detection (NRED) implementation structures are also disclosed. BRA demodulation filters Mis-Matched (MM) to that of the modulator filters, filters MM to that of theoretical optimal minimum bandwidth Nyquist filters. PE controlled adaptive equalizers and diversity systems having enhanced spectral efficiency and end-to-end performance are also described and included within the scope of this invention.

In general terms the present invention discloses and provides structure and method for cost effective solutions for Bit Rate Agile (BRA), modulation and demodulation (Modem) Format Selectable (MFS) and Coding Selectable (CS) processors, modulators/demodulators (modems), transmitters and receivers (Transceivers) with agile cascaded mis-matched (ACM) architectures having agile/tunable RF frequency embodiments and which are suitable for power efficient systems. This disclosure contains numerous structural and methodological embodiments and implementation architectures which lead to: (i) significant RF spectral savings, (ii) performance enhancements, and (iii) new features, functions and architectures; none of which were suggested or disclosed in the cited issued patents, inventions and references. Several of the references have been described as $1^{st}$ generation of Feher's Quadrature Phase Shift Keying (FQPSK), Feher's Quadrature Amplitude Modulation # (FQAM), Feher's Gaussian Minimum Shift Keying (FGMSK), and Feher's Minimum Shift Keying (FMSK) Transceivers.

The new implementation architectures, embodiments and new BRA technologies described in this disclosure are designated as subsets of second generation of FQPSK systems, suitable for BRA operation.

Overview of Exemplary Embodiments Described

A detailed disclosure of implementation architectures and embodiments of this invention is contained in the following sections. In many instances the text is related to the description of the respective figures and to the implementation of ACM transceivers. A changeable amount of cross-correlation between the BRA, CS, MFS and TCS response processor and/or combined or cascaded TCS and LR filters and/or post processor filters of the transmitter with selectable MM between the BRA transmitter and BRA receiver and CS processors, including single and separate in-phase (I) and quadrature (Q) signal storage/readout generators and single and/or separate I channel and Q channel D/A architectures for cross-correlated BRA, MFS and CS formats are also described. In agile cascaded mis-matched (ACM) designs for NLA and for Linearized (LIN) amplifiers selectable FQPSK filtering strategies, in the transmitter and separately in the receiver lead to further improvements in spectral efficiency.

Within an interface unit (IU) 107 in FIG. 1a a generalized block diagram of an embodiment of this inventive Transceiver 100 is shown and includes a BRA 102, MFS, CS, MM filtered and RF frequency agile enhanced spectral efficiency, high performance Transceiver block diagram. In this embodiment one or more input signals 150-1, 150-2, . . . , 150-N are received on single or multiple lead(s) 101-1, 101-2, . . . , 101-N and provided to a transmit section 152 of Interface Unit (IU) 102. The term lead or leads generally refers to a coupling or connection between the elements, and may for example refer to a wire, integrated circuit trace, printed circuit trace, or other signal link, connection, or coupling structure or means as are known in the art. Note that the IU provides an Interface port for transmission, designated as 102 and in the Receive section, also designated as 102, it contains the required IU receive processors and provides an output interface port. The input and output leads may contain and communicate analog or digitized voice, music, data, video, telemetry or other signals, or combinations thereof. In the FIG. 1a embodiment, signals 150 on input leads 101 may also represent Spread Spectrum, CDMA, WCDMA, CSMA, TDMA, FDMA or continuous single channel "Clear Mode", or other signals such as FDM and orthogonally frequency division multiplexed Orthogonally Frequency Division Multiplexed (OFDM) signals and IU port configurations.

The BRA 102 unit, shown in FIG. 1a provides signals 153 to a Base-Band Processor (BBP) unit 103. This unit 103, receives in addition to the output signals from the IU 102, signals on lead 104 a Clock (C), on lead 105 one or more Control (CTL) signals and on lead 106 one or more Sampling (SAM) signals. The combination of the aforementioned C, CTL and SAM signals is also designated with a common further abbreviation as "C".

BBP unit 103 provides a new class of BRA Cross-Correlated (CC) signals, including ACM filtered signals. The BBP provides signals to the Quadrature Modulator (QM) unit 109. Numerous embodiments of QM 109 have been described in the prior art and/or in the listed references. The QM implementation in baseband, IF and RF frequency ranges is well known by means of analog, digital and combined analog or digital techniques in hardware, firmware and in software and does not require further description. The Frequency Synthesizer, Unit 108, provides one or more unmodulated "Carrier Wave" signal(s) to the QM. The quadrature-modulated signals are provided to the Transmit Amplifier (AMP). The amplifier may be operated in a fully saturated mode, designated as Non-Linear Amplifier (NLA) or C-class amplifier or it may be operated in a Linearized (LIN or Lin) mode. Between the QM-109 and the Transmit AMP 111 part of the "RF Head" an optional combiner 110 is shown. Combiners 110 and/or post-AMP combiner 111 are optional units for Pilot Insert (PI) 1 and 2 designated as units 109 and 112, respectively. The RF head's transmit AMP is connected to Switch (SW) and/or Combiner/Splitter device 113 and this 113 unit provides the signal for transmission to and from antenna 114. Instead of the aforementioned antenna a separate port could be used for signal transmission or reception of "wired" systems. The Pilot Insert (PI) optional units may provide in band/or out of band pilot tones for transmission. These tones could be used for fast and robust performance receiver demodulators and synchronizers. In the transmit and receive sections Switch 113 or Switch or Combiner or Diplexer is connected to the receive Band Pass Filter (BPF) 115. Instead of Switch 113 a Combiner/Splitter could be used. The received signal after the BPF is connected to a Low Noise Amplifier (LNA) unit 116. The optional down-converter unit 117 receives its inputs from the Frequency Synthesizer and from the LNA and provides it to band-pass filter (BPF) 118 for further processing. The entire down-conversion stage of the receiver, including the receive section of the Frequency Synthesizer, mixers 117 and 118 are deleted for the so-called Direct Down-Conversion type of receivers.

The quadrature demodulator (Quad Demod) may contain components such as Automatic Gain Control (AGC), Frequency Tracking, Synchronization and Post Demodulation, Signal Conditioning including Symbol Timing Recovery (STR) circuits. The demodulated signal provided by demodulator unit 119 is fed to the receive section of the IU 102. The receiver section of the IU 102 contains on lead 101 the output signal and output port.

Figure 1B:
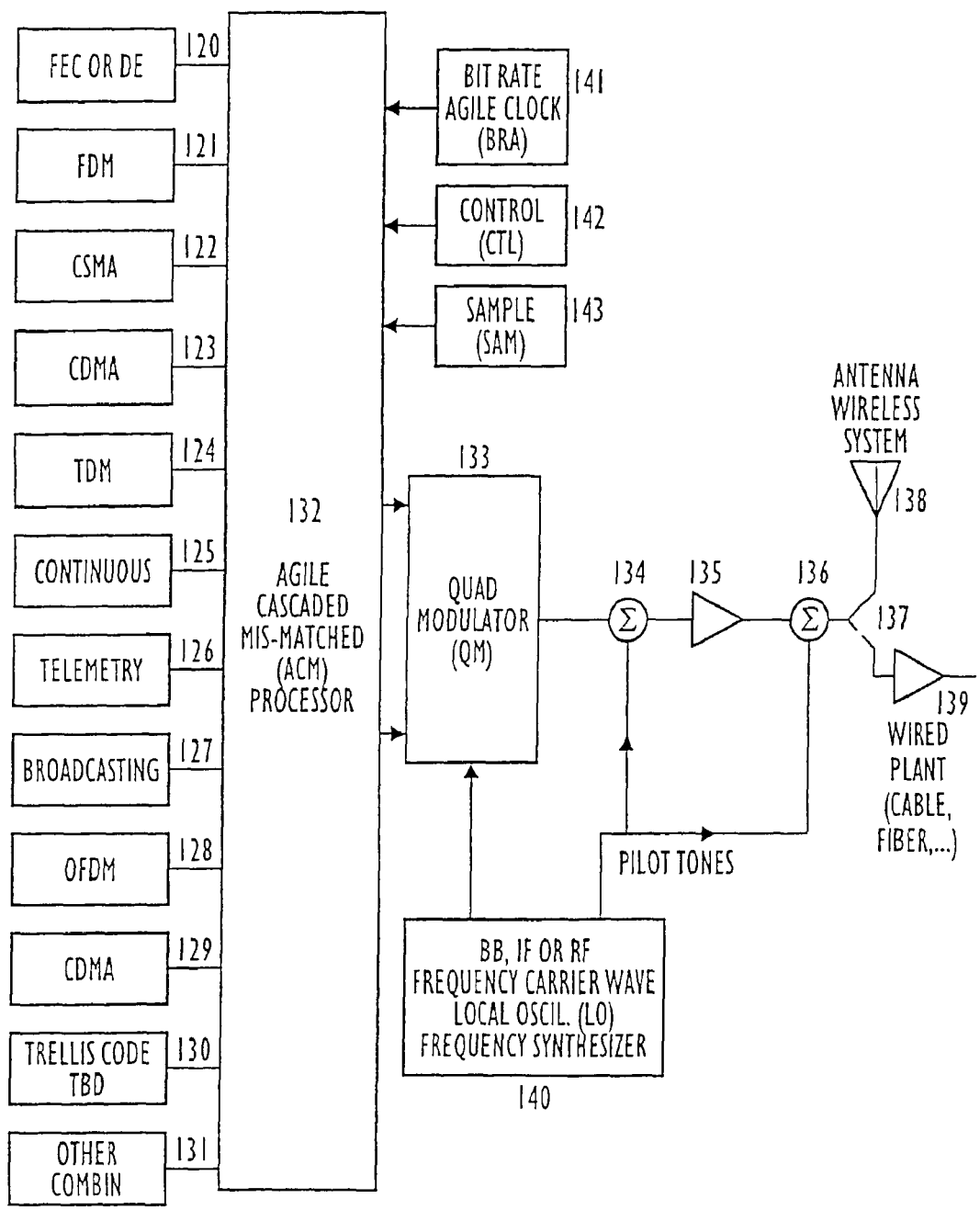
FIG. 1b illustrates a somewhat generic Transmitter (Tx) block-implementation diagram of the invention for bit rate agile, selectable modulation formats, for hardware, firmware and/or software implementations including optional single and multi-tone inserts at one or more locations.

In FIG. 1b, an alternate, somewhat generic Transmitter (Tx) block-implementation diagram of this invention for Bit Rate Agile (BRA), Modulation Format Selectable (MFS) hardware, firmware and/or software implementations, including optional single and multi-tone inserts at one or more locations and optional ACM embodiments, is depicted. Several optional interface units prior to the processor unit 132 are illustrated in this figure. These units may perform the transmit interface functions and the corresponding receive interface functions. Illustrative examples for the transmit interface functions are described. Unit 120 illustrates a Forward Error Correction (FEC) and/or a Differential Encoder (DE). Unit 121 is an interface for Frequency Division Multiplexing (FDM); for Collision Sense Multiple Access (CSMA) 122 would be used. For Code Division Multiplexes (CDMA) and its variations such as W-CDMA and B-CDMA and $3^{rd}$ generation CDMA 123 would be used. For time division multiplexed (TDM) 124, while for Continuous single or multiple digital or analog signals or Analog to Digital (A/D) converted signals unit 125 is used. For Telemetry interface 126, while for Broadcast Signal interface 127 is used. Unit 128 is suitable for Orthogonal Frequency Division Multiplexing (OFDM). For additional CDMA processing or interface 129 could be used. Trellis Coded Modulation (TCM) baseband processing of the trellis encoder and corresponding optimal demodulation/decoding could be performed in 130. Unit 131 is reserved for "other" emerging applications. Unit 132 is the processor, including the BBP for a generic class of signal generators disclosed in this invention. The baseband "in-phase" (I) and quadrature phase (Q) baseband signals generated by 132 are provided to QM 133. The QM unit receives an input also from the Carrier Wave (CW) generator also designated as Local Oscillator (LO) which could be part of the Frequency Synthesizer (FS) 140. The quadrature modulated output signal in one of the optional embodiments is combined with one or more Pilot Tones in combiners 134 and/or 136. Signal Amplifier (AMP) 135 provides the amplified signal to the Transmit and Receive Antenna 138 through switch or combiner/splitter 137. For wired applications such as telephony, coaxial cable, fiber and other physical wired connections interface unit/amplifier 139 is used. Bit Rate Agile Clocks (BRAC) are generated and/or processed in 141.

The Control (CTL) signals are obtained from unit 142 while one or multiple rate or sub bit rate Sampling Signals (SAM) are generated and/or processed by 143.

Figure 2:
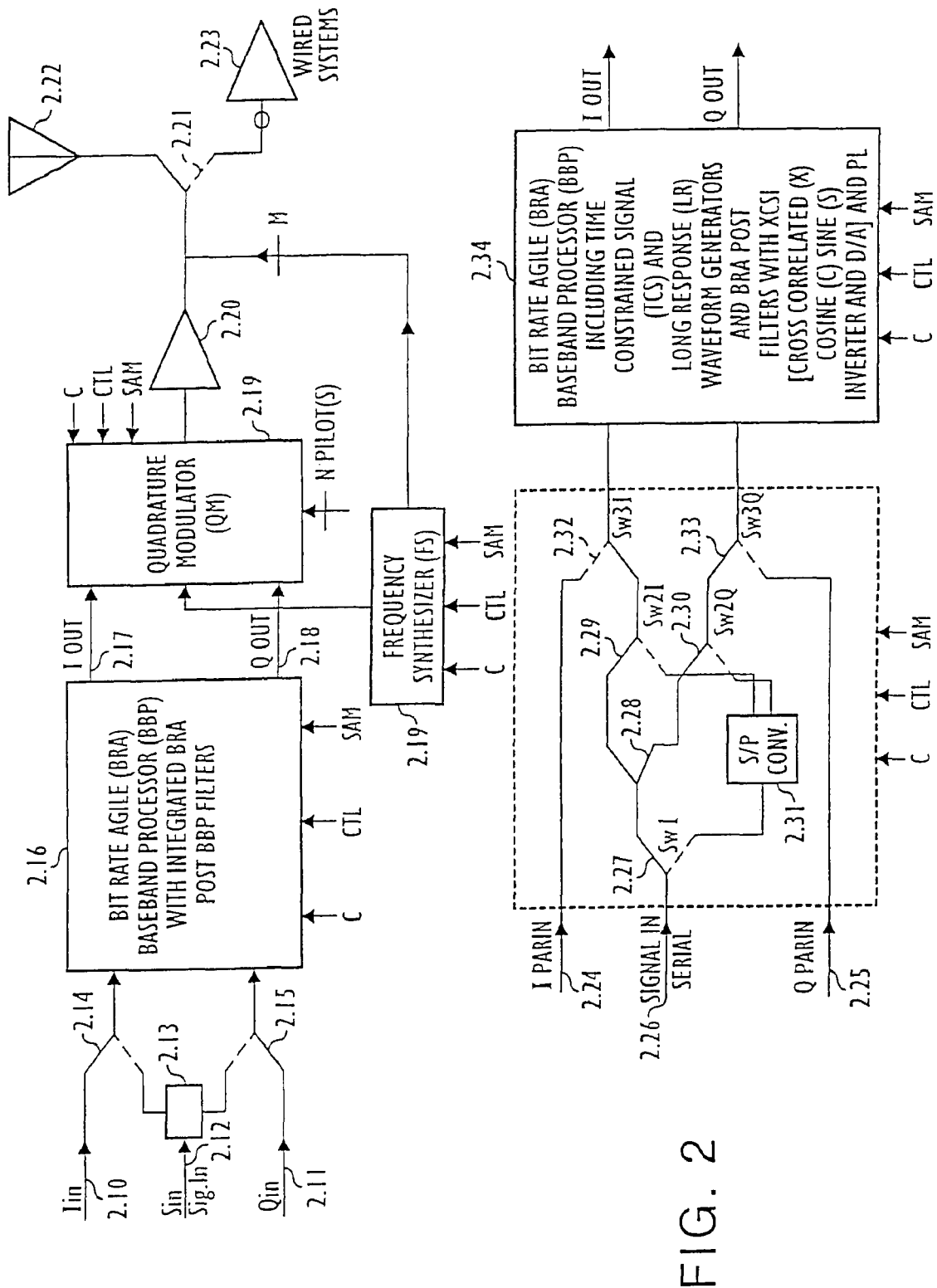
FIG. 2 depicts a Bit Rate Agile (BRA) integrated Base-Band Processor (BBP) with BRA post filters and BRA quadrature modulators. Signal splitting and serial/parallel BRA converters and TCS response processors in cascade with LR filter processors, which are MM enhancements and alternatives to referenced patents [P1 and P2] are also included.

In FIG. 2 an embodiment of a BRA integrated Base-Band Processor (BBP) with BRA post filters and BRA Cross-Correlated (CC) signals and ACM filters for quadrature modulation is illustrated. New BRA, MFS, CS and RF frequency agile implementation architectures of this invention are described in conjunction with FIG. 2. On signal leads 2.10 and 2.11 the in-phase input (Iin) and the quadrature phase input ($Q_{in}$) signals are provided to switch units 2.14 and 2.15. On lead 2.12 a serial input signal (Sin) is illustrated. This signal is connected to a Serial-to-Parallel (S/P) converter and/or Splitter unit, combined or individually also designated as "splitter" 2.13. Switching and/or combining units 2.14 and 2.15 provide in-phase (I) and quadrature phase (Q) baseband signals to the BRA processor 2.16. This BRA processor also receives a set of Clock, Control, and Sampling Signals C, CTL and SAM, commonly also referred to as set of C signals or merely "C" signal or "C" for clock. The $I_{out}$ and $Q_{out}$ signals are on leads 2.17 and 2.18 and provide inputs to the QM. The QM 2.19 provides drive signal (S) to amplifier 2.20 which in turn provides amplified signals to switch or combiner/splitter unit 2.21. Antenna 2.22 and/or interface port/amplifier 2.23 provide the signal to the transmission medium. Unit 2.19 Frequency Synthesizer (FS) provides the Carrier Wave Signals to one of the inputs of the QM and may provide one or more pilot tones to the QM and/or the output of 2.20 for combining the pilot tone(s) with the quadrature modulated signal.

In an alternative implementation of the baseband processor, in the lower part of FIG. 2, on leads 2.24 and 2.25 parallel input signals ($I_{parin}$) and ($Q_{parin}$) are provided, while on lead 2.26 a serial input signal is provided. Units 2.27, 2.29, 2.30, 2.32, and 2.33 are switching devices for the serial signal input and for the I and Q signals. Unit 2.28 represents a signal splitter. Signals and units 2.10 to 2.33 constitute some of signal processing components of this new architecture. These components have related structures to the description contained in Feher's prior art U.S. Pat. No. 5,491,457, Ref. [P2]. However, significant structural and implementation differences exist between the structures described in [P2] and the entire structure and embodiment of FIG. 2.

The architecture and embodiment of the Bit Rate Agile embodiment of the FIG. 2 processor includes BRA Baseband Processor (BBP) 2.34 with cascaded BRA Time Constrained Signal (TCS) response and Long Response (LR) signal generators. BRA post filters with Cross-Correlated (X) Cosine (C) and Sine (S) single or multiple processors and inverters (XCSI) are also part of the new structure. These structures, devices and architecture, including the new ACM filtering features available with these new elements are part of this invention.

Description of an Exemplary Embodiment of a FQPSK Bit Rate
Agile Transceiver

In this part of the detailed description of the invention the focus is on Quadrature Modulated (QM) four (4) state FQPSK systems. These four state systems have in general, in the sampling instants, in the I and Q baseband channels 2 signaling states (for short "states"). In the baseband I channel and in the baseband Q channel there are 2 signal states. The architectures and embodiments of nine (9) state FQPSK systems are essentially the same as that of 4 state FQPSK Transceivers. An exception is that the baseband I and Q Cross-Correlated and BRA signal processors provide 3 level (state) baseband I and Q signals and results in 3×3=9 state modulated FQPSK systems. Most implementations and embodiments and alternatives apply to multi-state (more than 4 state) Quadrature Modulated systems, described in later sections, such 9, 16 or 64 or 256 state QM systems having 3, 4, 7, 8 and 16 states in their respective baseband channels.

Figure 3:
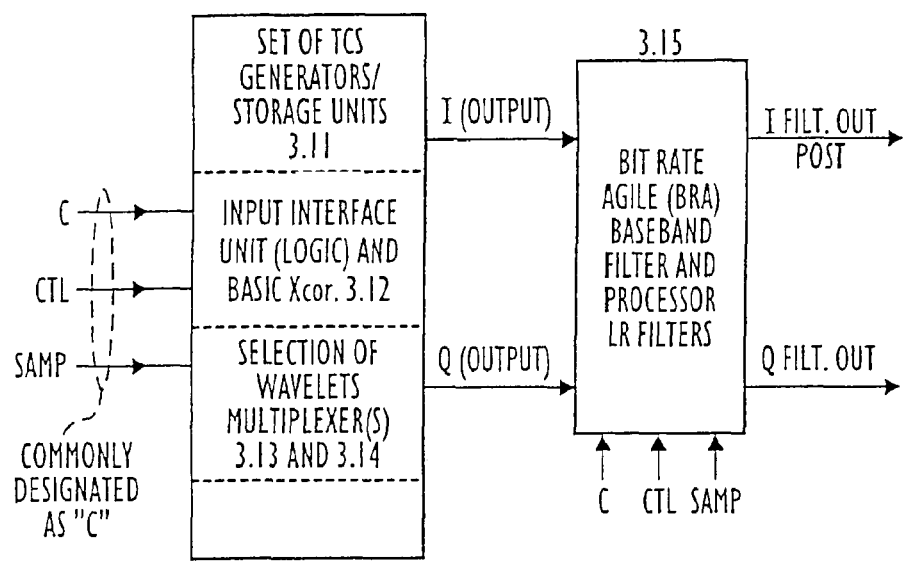
FIG. 3 shows TCS response and cascaded LR filter baseband processor and filter preceded by a cross-correlator, and multiplexers for I and Q signal generation.

FIG. 3 shows BRA baseband filters and processors preceded by a "basic cross-correlator (Xcor)" component of this FIG. 3. The basic Xcor component, including the wavelet storage units and multiplexers may be related to implementations described in the prior art Kato/Feher U.S. Pat. No. 4,567,602 patent [P5]. In some of the implementations of the present BRA invention, for use in BRA post filtered/processed system applications, these basic Xcor elements are used with integrated and/or post Xcor BRA filtered/processed ACM units. In some other embodiments different basic signaling elements including cascaded Time Constrained Signal (TCS) response and Long Response (LR) waveform generators and BRA post filters are used. In alternate embodiments of this invention the basic Xcor is connected to Cross-Correlated (X) Cosine (C) and Sine (S) single Inverters (XCSI). In some other alternate implementations the basic Xcor unit is not used. The combined embodiment and structure of the set of TCS and BCM signal generators, collectively designated as unit 3.11, combined with Multiplexers 3.13 and 3.14 and cascaded with the BRA cascaded TCS response and LR filters and baseband post filters 3.15 is different from that of the aforementioned prior art [P5].

Figure 4:
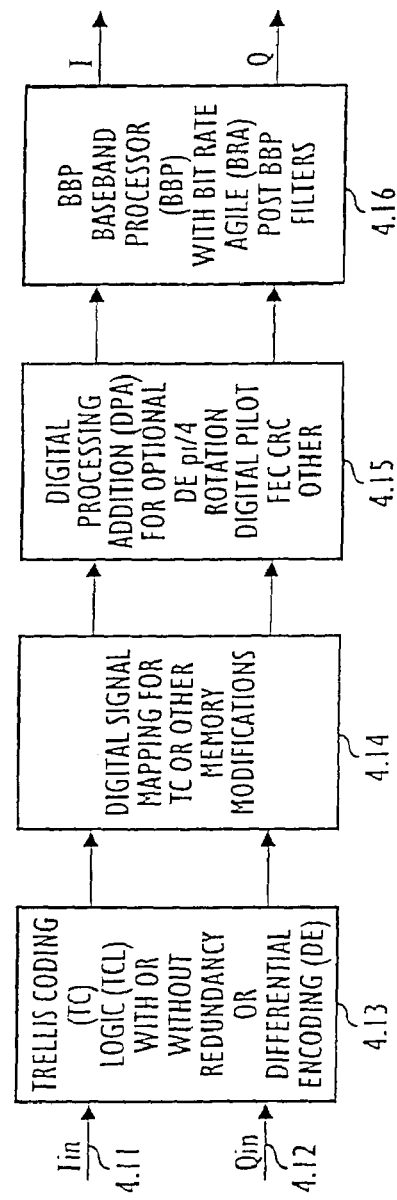
FIG. 4 illustrates coded baseband processing of FQPSK, FQAM, FGMSK and FMSK signals including non-redundant trellis coding of the baseband processed filtered I and Q signals.

FIG. 4 shows a trellis coded processor implementation architecture. Variations of this structure include one or more elements illustrated in FIG. 4. The shown structure is suitable for encoded signal generation including Differentially Encoded (DE) and/or Non-Redundant Trellis Coding (TC) of the Baseband Processed filtered I and Q signals. Alternately other Forward Error Correcting (FEC) devices are contained in unit 4.13. The architecture of this FIG. 4 is suitable for several $2^{nd}$ generation FQPSK embodiments. Elements of this structure generate enhanced spectral efficiency LIN and NLA constant envelope and non-constant envelope systems. BRA digital and analog implementations of ACM selectable parameter cross-correlators and several sets of transmit and selectable receive filters are included. Synchronous single data stream and asynchronous multiple data stream input processing has been also implemented with the shown structure of FIG. 4. Transmitters with and without preambles and trellis or other encoders and/or analog and digital pilot insertion as well as multi-amplitude cross-correlated signals including 3 level 7 level and multi-level partial response signals are also generated with the "mix and match" flexible and interoperable elements and structures.

On leads 4.11 and 4.12 the in-phase and quadrature phase input signals Iin and Qin are illustrated. Units 4.13 and 4.14 contain Digital Signal Processors (DSP) or FPGA logic elements, or other readily available processors. These processors perform functions such as Trellis Coding (TC) with or without redundancy, Differential Encoding (DE), Digital Signal Mapping for TC or other logic and/or memory modifications of the baseband signals. The Digital Processing Addition (DPA) unit 4.15 is provided for additional optional DE, Digital Pilot Insertion, and addition of Forward Error Correction (FEC) bits and/or symbols, including CRC and/or pi/4 rotation of the QM signal. Element 4.16 is a Bit Rate Agile (BRA) Base-Band Processor (BBP) which includes post-BBP ACM filters and/or post-Cross-Correlation (CC) filters and processors in the I and Q channels or a shared filter for the I and Q channels. The aforementioned functions and implementations could be used in the described sequence, or in a permutation or combination or variation of the aforementioned sequence. The entire processor of FIG. 4 could be implemented in one or more integrated steps without specific separation of the aforementioned functionality and/or implementation architectures.

One of the implementation alternatives of the Differential Encoded (DE) algorithm, used in some of the embodiments of this invention is described in the following paragraphs. In FIG. 4 the optional DE is part of unit 4.13 and is used for FQPSK and in particular for a specific FQPSK embodiment, designated as FQPSK-B, Revision A1 as well as FGMSK, FMSK and FQAM Transceivers. A somewhat more detailed implementation block diagram of entire Differential Encoder (DE)-Differential Decoder (DD) and corresponding Serial to Parallel (S/P) and Parallel to Serial (P/S) converters is shown in FIG. 18.

Figure 18A:
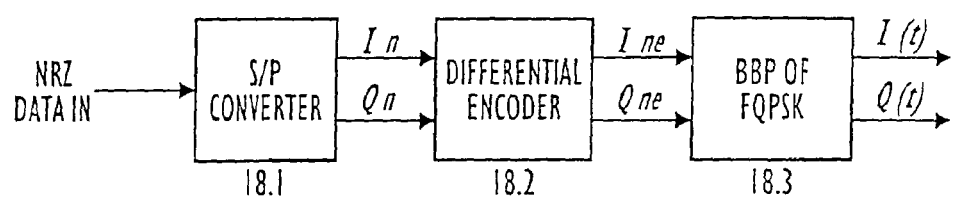
FIG. 18 shows Differential Encoding (DE) and Differential Decoding (DD) for FQPSK and FGMSK.
Figure 18B:
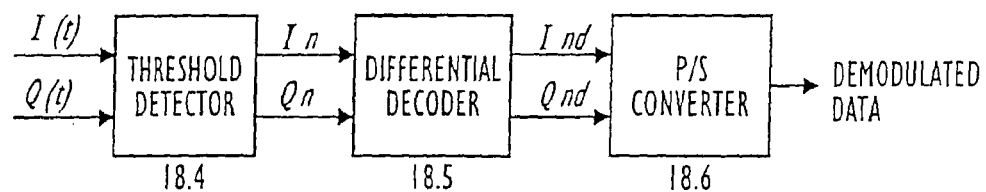

A Serial-to-Parallel (S/P) processor, such as processor 18.1 of FIG. 18, is inserted prior to the DE 4.13 of FIG. 4 or prior to the DE unit 18.2 of FIG. 18. The Differential Encoder 4.13 Differentially Encodes (DE) the I and Q data streams. The baseband I and Q signals are differentially encoded as follows:

$$I = D_{even\_}Q^{bar}$$

$$Q = D_{odd\_}I$$

In an alternative implementation of the aforementioned DE the inversion "bar" is on I in the second equation instead of the Q of the first equation (that is I-bar rather than Q-bar).

$$I = D_{even\_}Q$$

$$Q = D_{odd\_}I^{bar}$$

In one of the FQPSK embodiments, designated as FQPSK-B, one of the implementations has the I and Q data symbols offset by one bit time (Tb), corresponding to a ½ symbol time (Ts), i.e. Tb=Ts/2. $D_{even}$ and $D_{odd}$ are the even and odd input data bits. In alternate embodiments, the aforementioned offset is not used. In the case of Direct Sequence Spread Spectrum systems such as certain CDMA systems, instead of the offset by 1 bit time the offset could correspond to 1 chip time or to a presetable time.

Figure 5A:
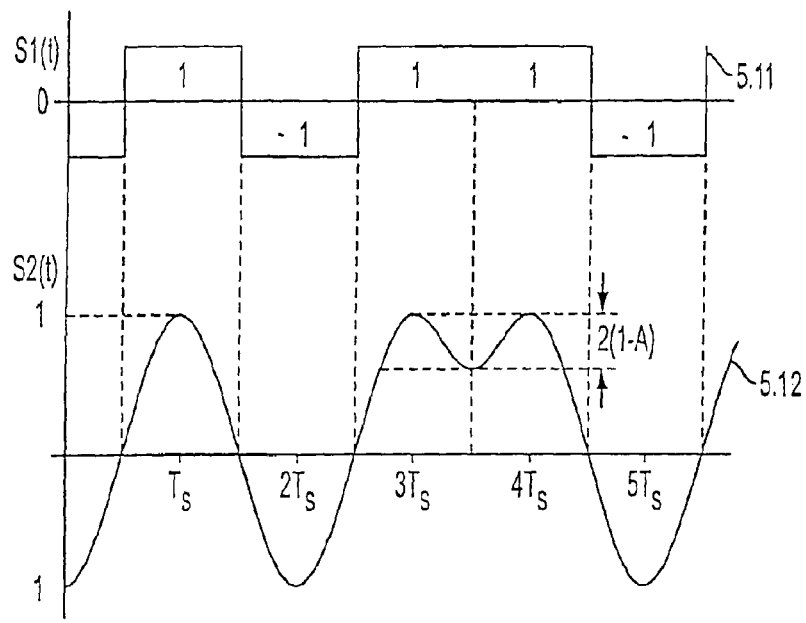
FIG. 5 Time Constrained Signal (TCS) patterns, based on referenced patents [P4; P5; P7] are illustrated.
Figure 5B:
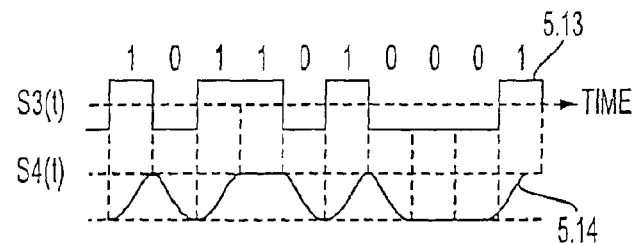
Figure 5C:
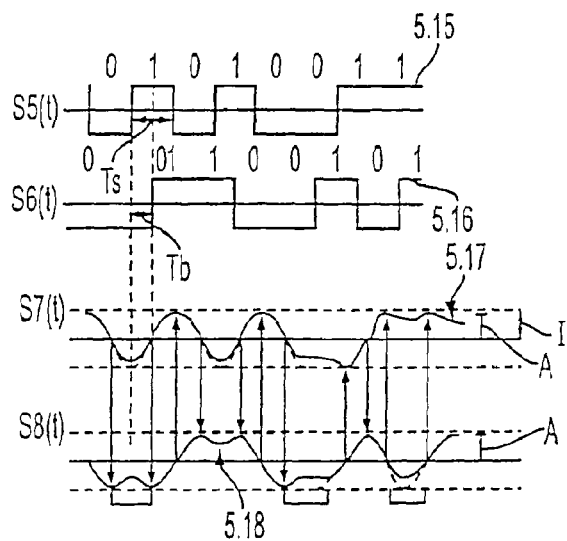

In FIG. 5 several Time Constrained Signal (TCS) response patterns are illustrated. TCS and/or TCS response patterns are illustrated, described and defined with the aid of the synonymous terms "Signaling Elements (SE)", "Signal Components" or "Wavelets." The terms TCS, TCS processor and/or TCS response shall mean that the pulse response or alternatively the impulse response of TCS processors is constrained to the length of the memory of TCS processors. This TCS response may have an impact on the cascaded response of a TCS processor with that of subsequent filters. TCS response cross-correlated and also TCS response signal patterns without cross-correlation are illustrated in FIG. 5. These are used in some of the implementations of this invention as signaling elements or wavelets connected in cascade to Long Response (LR) filters. The term "Long Response filter" or "LR filter" means that the measurable pulse response and/or impulse response of an LR filter or processor is longer than the pulse response of the TCS response processor. In several implementations the LR filter is implemented by conventional filter synthesis and design. Conventional filter designs include the design and implementation of active and passive Bessel, Butterworth, Chebycheff, Gaussian, analog and digital filters and of hybrid analog/digital filters. In alternate LR filter designs Infinite Impulse Response (IIA) and also Finite Impulse Response (FIR) architectures are implemented.

The pulse response of TCS response processors is limited to the memory of the TCS processor. In several embodiments the memory of the TCS processor and/or TCS cross-correlator has been between ½ and 3 symbol duration Ts intervals. The pulse response of LR filters is related to the type of the selected filter, the roll-off and the 3-dB bandwidth (B) and bit rate duration (Tb). For example an $8^{th}$ order Chebycheff filter, having a BTb=0.5 could have a practical, measurable pulse response of more than 10 bit duration. A $4^{th}$ order Butterworth filter having a BTb=1 could have a practical pulse response of more than 4 bit duration, depending on the accuracy/inaccuracy of pulse response and resulting Intersymbol Interference (ISI) definitions and requirements.

The basic TCS signaling elements or "Wavelets" shown in FIG. 5 precede the LR filters of the ACM embodiments. In alternate architectures the sequence of TCS and of the LR filters/processors is interchanged and also used in parallel architectures for combined TCS and LR signal generation. The TCS signal elements or for short "Signals" or "wavelets" in FIG. 5 are described as follows: signal pattern 5.11 represents pattern S1(t) of a Non-Return-to-Zero (NRZ) signal pattern. The NRZ signal pattern contains TCS signaling elements where the duration of each NRZ signaling element is constrained to one Time Symbol (Ts) duration. Signal pattern 5.12, also designated as S2(t), represents an other one Time Symbol TCS response wavelet pattern. This TCS response signal could be generated by the "Superposed Quadrature Modulated Baseband Signal Processor" (SQAM) Seo/Feher's U.S. Pat. No. 4,644,565, Ref. [P4]. Another TCS pattern, designated as pure Intersymbol-Interference and Jitter Free (IJF) signal pattern, or pure IJF wavelet and pattern, based on Feher's U.S. Pat. No. 4,339,724 [P7] is signal 5.14 also designated as S4(t). It is a TCS pure IJF signal pattern corresponding to the alternate NRZ pattern example shown as signal 5.13 and designated as S3(t). Signals 5.15 and 5.16 designated as S5(t) and as S6(t) are in-phase (I) and quadrature phase (Q) half a Time Symbol (Ts) time delayed NRZ baseband signals. In this designation half a symbol duration corresponds to one Time Bit (Tb) duration that is Ts=Tb/2. Signal patterns 5.17 and 5.18 corresponding to S7(t) and as S8(t) are additional illustrative examples of TCS signals. These TCS signals represent in-phase (I) and Quadrature-phase (Q) baseband Cross-Correlated (CC) or (Xcor) signal patterns which could be generated by use of the Kato/Feher U.S. Pat. No. 4,567,602, Ref. [P5]. These S7(t) and S8(t) cross-correlated TCS response signal patterns represent IJF encoded output signals having amplitudes modified from the peak amplitudes of IJF signals.

Figure 6A:
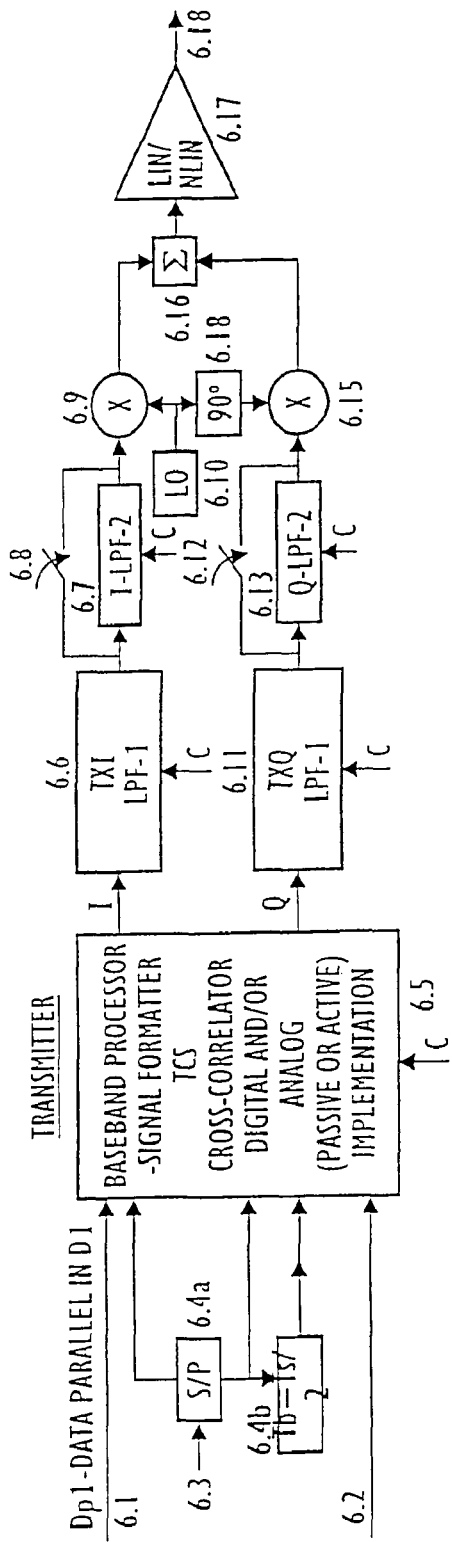
FIG. 6 shows an Agile Cascaded Mis-Matched (ACM) implementation block diagram embodiment of this invention with cascaded, switched transmit (Tx) and receive (Rx) Low-Pass-Filters (LPF) for BRA applications in conjunction with Cross-Correlated and other non-cross-correlated cascaded Time Constrained Signal (TCS) response processors and Long Response (LR) filters having substantially Mis-Matched (MM) modulation and demodulation filters.
Figure 6B:
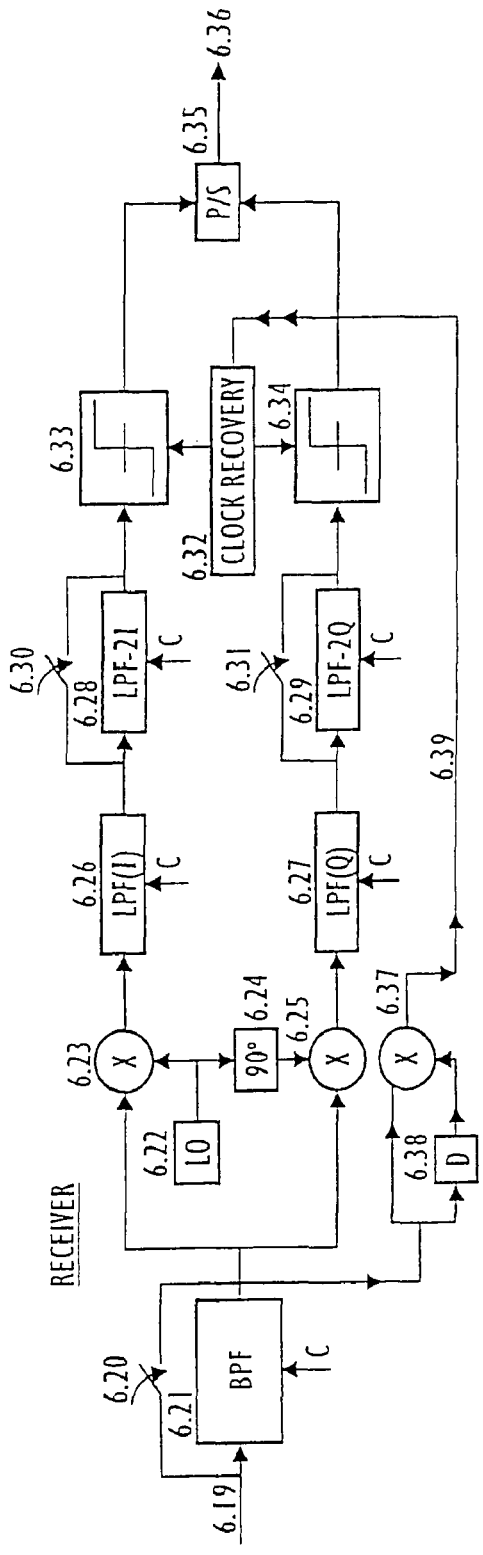

In FIG. 6 an implementation diagram with cascaded switched transmit (Tx) and receive (Rx) Low-Pass-Filters (LPF) in conjunction with cross-correlated and other non cross-correlated TCS response and cascaded LR processors is shown. These LR processors could be implemented as separate I and Q LPFs or as an individual time-shared LPF. The Transmit Baseband Signal Processor (BBP) including the I and Q LPFs could be implemented by digital techniques and followed by D/A converters or by means of analog implementations or a mixture of digital and analog components. External Clock and External Data Signals are used to drive the S/P and the entire baseband processor (BBP). The BBP may include a Differential Encoder (DE). The I and Q LPFs may be implemented as single filters (instead of cascaded filters). Modulation and Demodulation filters have been implemented and tested with intentionally Mis-Matched (MM) filter parameters. Some of the best performance implementations use Agile Cascaded Mis-Matched (ACM) architectures. LR filters have been synthesized and implemented as phase equalized and also as non-equalized phase response transmit and receive Bessel, Gaussian, Butterworth and Chebycheff filters. Bessel, Gaussian and Butterworth and Chebycheff filters as well as other classical filters are within the previously described and defined class of Long Response (LR) filters. These filters have a relatively long practical impulse and/or pulse response. The measurable practical pulse response of the aforementioned filters having an approximately BTs=0.5 design parameter extend to many bit durations. Here B refers to the 3 dB cut-off frequency of the filter and Ts to the unit symbol duration. From classical communications and Nyquist transmission theory it is well known that the theoretical optimal performance minimum signal bandwidth is defined for BTs=0.5. The LPFs in the I and Q channels, or the shared single set of LPFs, implementations include Infinite Impulse Response (IIR) and Finite Impulse Response (FIR) filters.

In FIG. 6 on lead 6.3 a serial data stream is present. This signal is provided to 6.4a and the optional 6.4b units for Serial-to-Parallel (S/P) conversion and a 1 bit duration (Tb) offset in one of the implementations. In other implementations there is no offset delay 6.4b in the embodiment. Some other alternate embodiments use a selectable offset delay 6.4b which is larger or equal to zero and smaller than the duration of approximately 200 bits. As stated the Offset logic is used in certain embodiments, while in other architectures it is not present. The input signal or input signals are provided on leads 6.1 and 6.2 instead of lead 6.3 in some of the alternative implementations of this invention. Unit 6.5 is a Base-Band Processor. Unit 6.5 may be clocked, controlled and sampled by signals such as C, CTL, and SAMP such as illustrated previously in FIG. 1 to FIG. 3. In this figure, FIG. 6, all of these clocking, control and sampling signals which could represent multiple rates and multiple leads are collectively or individually abbreviated simply as "C" and illustrated with an arrow near the letter "C." Unit 6.5 in some of the embodiments performs the Time Constrained Signal (TCS) processing, waveform assembly and generation functions of multiple symbol TCS cross correlation and signal processing operations. The I and Q outputs of unit 6.5 are provided as inputs to the transmit set of LPFs designated as TX1 LPF-1 unit 6.6 and TXQ LPF-1 unit 6.11. This set of first LPFs could be cascaded with a second set of I and Q channel LPFs units 6.7 and 6.13. Switch units 6.8 and 6.12 illustrate that the second set of LPFs could be bypassed and/or deleted in some of the embodiments.

The LR filter units, embodied by the first and second sets of I and Q are implemented as LPFs or alternately as of other types of filters such as Band-Pass Filters (BPF) or High Pass Filters (HPF) or other filter/processor LR filter combinations. As stated previously, for several embodiments all of the aforementioned processors are BRA and ACM, while for other implementations bit rate agility and/or ACM may not be required. Units 6.9, 6.10, 6.14, 6.15 and 6.16 comprise a quadrature modulator in which the I and Q modulators are 90-degree phase shifted and in which a Local Oscillator (LO) is used as a Carrier Wave (CW) generator. Unit 6.17 is an amplifier that could be operated in a LIN or in a NLA mode. The output of amplifier 6.17 is provided on lead 6.18 to the transmission medium.

In FIG. 6 at the receiving end, on lead 6.19, is the received modulated signal. Unit 6.21 is a BPF that is present in some embodiments while in others it is not required. Alternatively the receive BPF could be "switched-in" or "switched-out" by switch 6.20. In some implementations Surface Acoustic Wave (SAW) BBF were used to implement 6.21. Units 6.22, 6.23, 6.24 and 6.25 embody a Quadrature Demodulator (QD) with a corresponding Local Oscillator (LO). The aforementioned LO represents for some embodiments an entire Carrier Recovery (CR) subsystem while for other embodiments it is a free running LO. The set of LPFs 6.26 and 6.27 are the embodiment of post-demodulation filters, while the second set of LPFs 6.28 and 6.29 may be used to further enhance the spectral efficiency advantages or other performance advantages of designed ACM systems. The second set of LPFs could be connected or disconnected by switches 6.30 and 6.31 or entirely deleted. Unit 6.32 is the Clock Recovery (CR) and/or Symbol Timing Recovery (STR) system. For fast clock and/or STR, this unit is connected in some of the embodiments in parallel to the Carrier Recovery (CR) subsystem. In one of the embodiments of fast Clock Recovery (CR) systems, the parallel configuration embodied by units 6.37 and 6.38 is used for discrete signal clock generation. The discrete signal spike, in the frequency domain, provides on lead 6.39 the clock recovery unit 6.32 with a discrete spectral line signal which is exactly at the symbol rate or at the bit rate. In this architecture unit 6.37 is a multiplier or any other nonlinear device which has at its input the received modulated signal and the same received modulated signal multiplied by a delayed replica of itself. The aforementioned delayed replica is generated by unit 6.38, a delay element. The receiver structure, shown in FIG. 6, is one of the many possible alternative receiver and demodulator structures. It is inter-operable compatible and suitable for BRA and MFS and CS reception, demodulation and/or decoding of the transmitted signals embodied by means of the BRA and/or MFS and/or CS and/or ACM implementation of the FIG. 6 transmitter embodiments.

Contrary to the teachings and wisdom of well established bandwidth efficient communication theory, of matched filter-optimal demodulation theory and optimal data reception theories, in several embodiments of the current invention, substantially Mis-Matched (MM) modulator and the demodulator filters have been implemented. Fundamental and pioneering discoveries, regarding the cascaded pulse response of TCS response and of LR filter cross-correlated BRA implementations of modulator I and Q filters and that of the implementations of "matched" and/or intentionally "Mis-Matched" (MM) demodulator filters are disclosed in this part of the invention. In classical communication theory the demodulation LPFs, and in fact the entire cascaded receiver and demodulation filter responses are matched to the characteristics of the modulator and entire cascaded modulator and RF transmitter filters. Minimum bandwidth-maximal spectral efficiency, optimal performance requires that the Nyquist minimum bandwidth theorems be satisfied for ISI free and matched signal transmission/reception. The intentionally and substantially Mis-Matched (MM) transmit and receive filter designs, used in implementations of this invention lead to simpler implementations than implied by communication matched filter theory and by Nyquist minimum bandwidth theories and to substantially improved performance for RF power efficient NLA transceivers. From communications theory, numerous books, referenced publications as well as from patents it is well known that for "optimum" performance the cascaded filters of the modulator should be matched by the cascaded receive demodulator filters. For example, in a conventional bandlimited QPSK system, if Nyquist filters are implemented as "raised cosine filters", then the best "optimal" performance is attained if the cascaded transmit and receive filters have a raised cosine transfer function and the filtering is equally split, i.e. "matched" between the transmitter and receiver. For pulse transmission, such as filtered NRZ data an aperture equalizer, having an wTs/sin(wTs) frequency response is used in theoretical optimal transmitters, prior to the implementation of the transmit matched filter. Specifically, based on Nyquist transmission and filter theories, combined with matched filter receiver theories the 3 dB cut-off frequency of an optimal minimum bandwidth transmit filter, used as a baseband I or Q channel filter, in a QPSK system equals ½ of the symbol rate or alternatively ¼ of the bit rate. The 3 dB bandwidths of the modulator and demodulator filters of the "theoretical optimal" bandlimited QPSK system are matched. The 3 dB bandwidth of the theoretical optimal system it is the same for the modulator filter and for the demodulator filter. If these filters are implemented by pre-modulation LPFs and post-demodulation LPFs then the aforementioned theoretical bandwidth corresponds to BTs=0.5. This value corresponds to BTb=0.25, where B is the 3 dB bandwidth of the respective filters, Ts is the unit symbol duration and Tb is the unit bit duration.

Contrary to the teachings of the aforementioned optimal performance matched filter modulation demodulation theory, we disclose the implementation of demodulator architectures and embodiments with "Mis-Matched" (MM) filtering, and specifically for agile (bit rate) cascaded mis-matched (ACM) implementations. The term Mis-Match (MM) refers to intentional and substantial MM between the cascaded 3 dB bandwidth of the I and Q demodulator filters and/or to the MM with respect to the Nyquist theory stipulated bandwidth. with that of the cascaded response of the modulator I and Q filters. Alternate embodiments include MM pre-modulation baseband LPF and post-demodulation baseband LPF designs as well as post modulation BPF transmitter implementations and receiver pre-demodulation BPF implementations. A combination of the aforementioned baseband and BPF designs has been also implemented. The term "substantial" MM in a BRA architectures and embodiments such as shown in the alternate implementation diagrams in FIG. 6 or FIG. 7 or FIG. 10 to FIG. 15 and/or FIG. 25 or FIG. 30 implies typically more than about 30% mis-match between the respective 3 dB cut-off frequencies of the transmit and receive filters, but this value is exemplary and is not a limiting amount of mis-match.

One of the best known BRA implementations of FQPSK systems is designated as the "FQPSK-B" family of transceivers. In this section, several best embodiments of FQPSK-B Transceivers, operated in NLA systems are described. The implementation of the FQPSK-B embodiment, described in this section has BRA, CS and MFS architecture with substantially MM modulation and demodulation filters. The modulator TCS response processors cascaded with the LR filters and the demodulation filters are Mis-matched (MM). In this FQPSK-B implementation a cross-correlation factor of A=0.7 has been implemented between the I and Q baseband TCS response processors which are cascaded with the LR filters. The TCS wavelets and assembly of the TCS wavelets has been described in the Kato/Feher patent Ref. [P5]. A resulting I and Q cross-correlated data pattern of this implementation, at the TCS processor output and prior to the BRA LR filters is shown in FIG. 5 as TCS data patterns S7(*t*) and S8(*t*) having a cross-correlation parameter A=0.7. The I and Q baseband signal patterns are generated with several structures and elements, described as parts of this invention. The aforementioned TCS signal patterns are available at the outputs of the following elements: in FIG. 6 at the output leads of TCS 6.5, in FIG. 7 at the output leads of D/A Units 7.8 and 7.11. In FIG. 8 at the output leads of units 8.7 and 8.8. In FIG. 10*b* at the output leads of the D/A converter units 10*b*.17 and 10*b*.18, and in FIG. 15 at the output leads of D/A converter (designated as DAC's) units 15.7 and 15.14.

The aforementioned BRA, MFS, CS and intentional Mismatched (MM) implementations and embodiments of four state FQPSK Transceivers, operated over NLA systems are applicable to Multi-State NLA systems, described in later sections.

Figure 7:
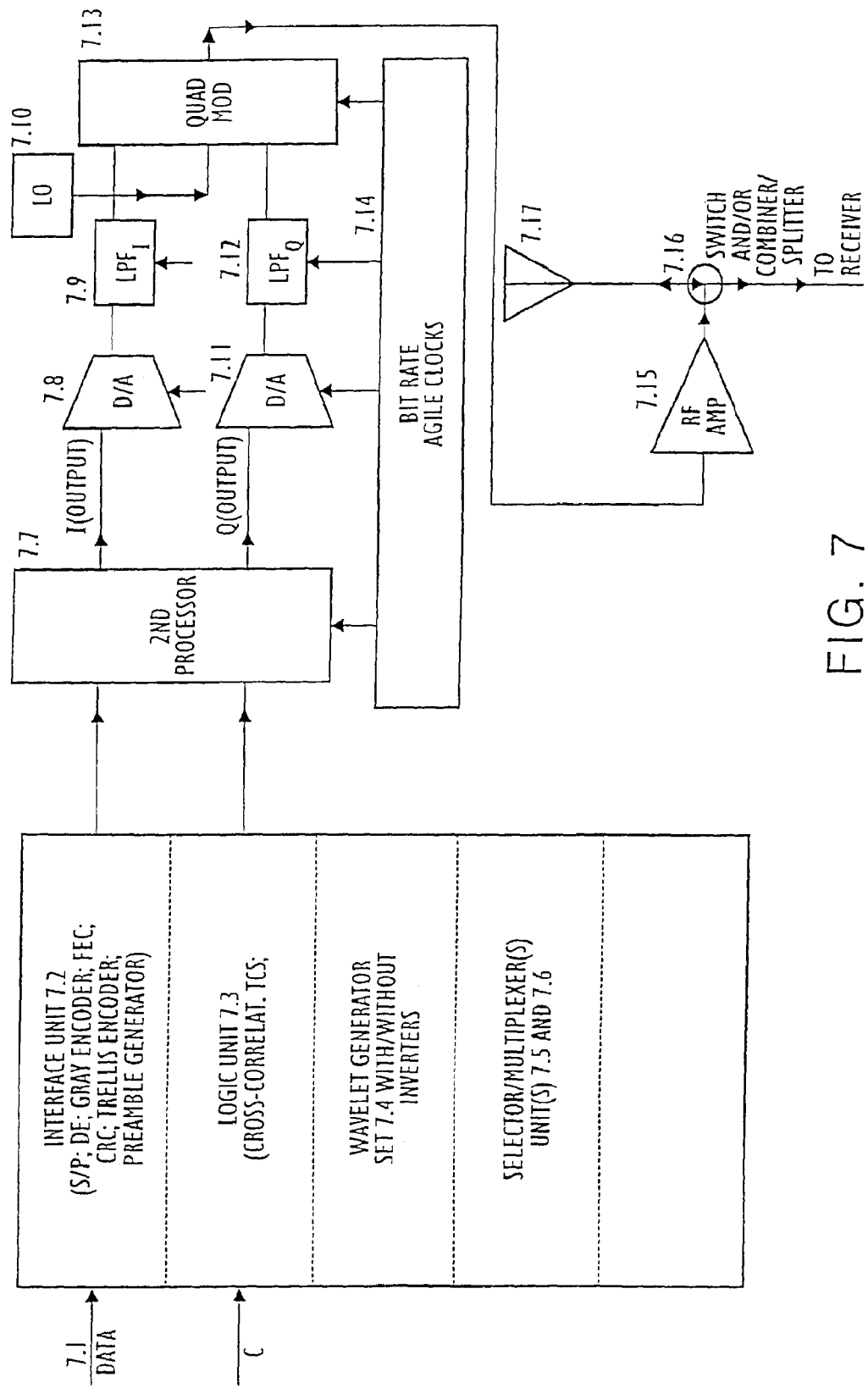
FIG. 7 is an alternate embodiment-block diagram of the current invention, including Cross-Correlator in cascade with a $2^{nd}$ processor and with Digital to Analog (D/A) converters followed by spectral and pulse shaping bit rate agile LR filters, implemented by Low-Pass-Filters (LPF) in the I and Q channels of this Quadrature modulator.
Figure 8:
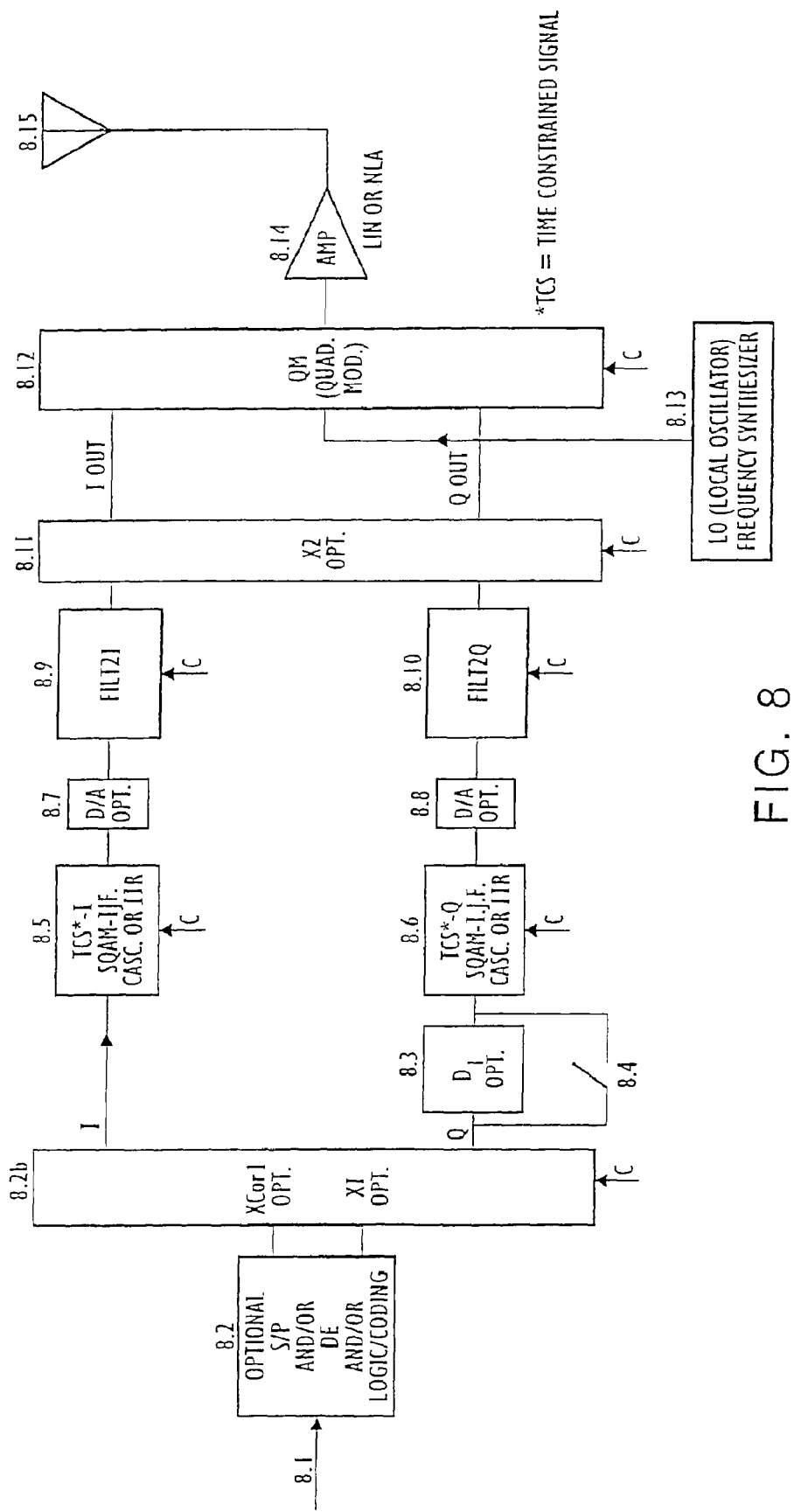
FIG. 8 shows the implementation of an alternate Quadrature Modulator (QM) Transceiver having one or more Intersymbol-Interference and Jitter Free (IJF), Superposed Quadrature Amplitude Modulation (SQAM) or TCS response cascaded with LR response filter embodiments in the I and Q transmit Baseband Processor (BBP).

In FIG. 7 one of the alternate implementations of Bit Rate Agile (BRA) transmitters is shown. The illustrated embodiment of the current invention uses a variation and alternative implementations of the "Basic Cross-Correlator" (XCor) and post cross-correlation processors, as disclosed in prior patents of Feher et al., with several original embodiments described in conjunction with FIG. 7. In cascade with the basic Xcor which implements TCS response processed cross-correlated or TCS not-cross-correlated signals is a second set of LR filtered processors. In cascade with the $2^{nd}$ processor and with Digital to Analog (D/A) converters are pulse shaping bit rate agile LR filters, implemented as Low-Pass-Filters (LPF) or other type of filters in the I and Q channels. As stated previously, BPFs, HPFs or other types of processors/filters could replace the LPFs. On lead 7.1 is the input signal to unit 7.2, which implements S/P, DE and Gray encoding and/or other logic functions. Logic 7.3 is a cross correlator that is used to cross correlate I and Q signals. The duration of the cross correlation processor and implementation of the basic Xcor is selectable in the current invention. It is selectable in a wide range, from zero, i.e. no cross-correlation to a fraction of a bit interval, and is adjustable and/or selectable up to many bits and/or symbols. In some of the alternate implementations of FIG. 7 the entire cross-correlation Unit 7.3 designated as "Logic" is not used, that is, it is deleted from FIG. 7, in the generation and assembly of the TCS response signals, provided by the signal generator set 7.4. In logic/cross-correlator 7.3 six symbol shift registers are shown for the I and Q channels. As stated in alternative embodiments the cross correlation is deleted. The basic signaling elements, also referred to as wavelets, designated F1, F2, . . . , F16 are generated and/or stored by a set of signal generators or storage devices designated as 7.4. The aforementioned storage units or wavelet generators are implemented in one of the alternate embodiments with ROM and/or RAM chip sets and/or are part of a firmware and/or software program. In certain embodiments a fairly large number of wavelets are generated, i.e., a set of S0, S1, S2, . . . , S63 or even more wavelets are generated, while in other embodiments only 2 or 4 signaling elements (wavelets) are used. In alternate implementations instead of generating and/or storing separate and distinct signals or "wavelets", a very small number of wavelets is stored and their inversions in terms of amplitude inversion and time inversions are used. In the embodiments of the current invention the elements are suitable for BRA and ACM operation. Units 7.5 and 7.6 are designated as two multiplexes and are embodied in some implementations as a single integrated multiplexer unit or more than one unit. In one of the embodiments all digital processors, including units 7.2 to 7.16 are implemented as a single function and unit. Unit 7.7 is a second processor and provides for optional additional cross correlation and amplitude limiting, also designated as signal clipping or Peak Limiter (PL). PL are implemented by clipping devices and/or other commercially available prior art nonlinear devices. Other conventional devices described previously in these specifications as well as in the prior art literature embody units 7.8 to 7.13. Amplifier 7.15 provides the RF modulated signal to the antenna 7.17 through a switch and/or combiner or splitter 7.16.

In FIG. 8 a Quadrature Modulated (QM) Transceiver embodiment of this invention is shown. On lead 8.1 the input signal is provided to the optional S/P and/or DE and/or Logic/

Coding processor 8.2*a*. Unit 8.2*b* is an optional (Opt.) Xcor, designated in FIG. 8 as Xcor 1. Unit 8.2*b* provides I and Q signals through the optional offset delay, D1 unit 8.3 or optional bypass switch 8.4 for further processing to units 8.5 and 8.6. Units 8.5 and 8.6 implement one or more I and Q processing operations of Intersymbol Interference (ISI) and Jitter Free (IJF) signals such as cross-correlated amplitude-adjusted IJF signals or other TCS cross-correlated and/or non-cross-correlated signals including binary and multilevel SQAM signaling elements in cascade with LR filter subsystems such as IIA and/or FIR processors which are operated in a BRA mode. Units 8.7 and 8.8 are D/A optional single shared D/A, or multiple D/A converters that provide signals to the second set of filters 8.9 and 8.10. Analog, digital or hybrid hardware, software or firmware in unit 8.11 implements an optional cross correlator. The I and Q output signals of 8.11 are provided as baseband drive signals of the QM 8.12. Local Oscillator (LO) 8.13 provides the RF unmodulated CW to the QM. The QM provides to Amplifier 8.14 a signal for amplification to antenna 8.15 or to the transmission medium. One of the embodiments has a very simple/efficient implementation of the TCS response cross correlated transmit (Tx) processor with only 4 samples/symbol and only three (3) wavelets.

In FIG. 9 Peak Limited (PL) and other TCS response signal patterns of this invention as well as that generated by the prior art Superposed Quadrature Modulated Baseband Signal Processor ("SQAM") Seo/Feher's U.S. Pat. No. 4,644,565, Ref [P4] are illustrated. Signal pattern designated as 9.11 is a conventional prior art NRZ signal, while TCS pattern 9.12, if it is not cross-correlated with an other signal or not cascaded with a LR processor, represents a processed prior art SQAM generated baseband signal wavelet pattern. If the TCS pattern 9.12 signal is connected to BRA one or more filters, including LR filters and/or ACM Processor's and it is part of I and Q cross-correlated signal generators and BRA processors, then it is a new implementation of this invention, having a substantially enhanced bandwidth efficient signal. Signal pattern 9.12 is reproduced as signal pattern 9.13. The dotted line of signal pattern 9.14 illustrates the TCS processor and cascaded Long Response (LR) filtered output sample signal pattern. The 9.14 LR filtered signal pattern is more spectrally efficient than the 9.12 TCS response signal, however it may contain more Intersymbol-Interference (ISI), more Data Transition Jitter (for short "Jitter") and higher signal peaks than the TCS signal pattern. A PL or "Clipped" signal pattern 9.16 of this invention is illustrated with dotted lines adjacent to signal pattern 9.15. Signal clipping and/or smooth gradual or soft PL or abrupt peak limiting of TCS, and/or of TCS response processors cascaded with LR filters and/or cross-correlated signals reduces the overall signal excursion of the peak to peak amplitude variation of the I and Q signals. It also reduces the envelope fluctuation of the I and Q modulated signal. Applications include I and Q analog and digital signals, including Orthogonal Frequency Division Multiplexed (OFDM), clear mode non-spread spectrum as well as spread spectrum signals, such as CDMA and also TDM or TDMA, CSMA and FDMA architectures.

Figure 10A:
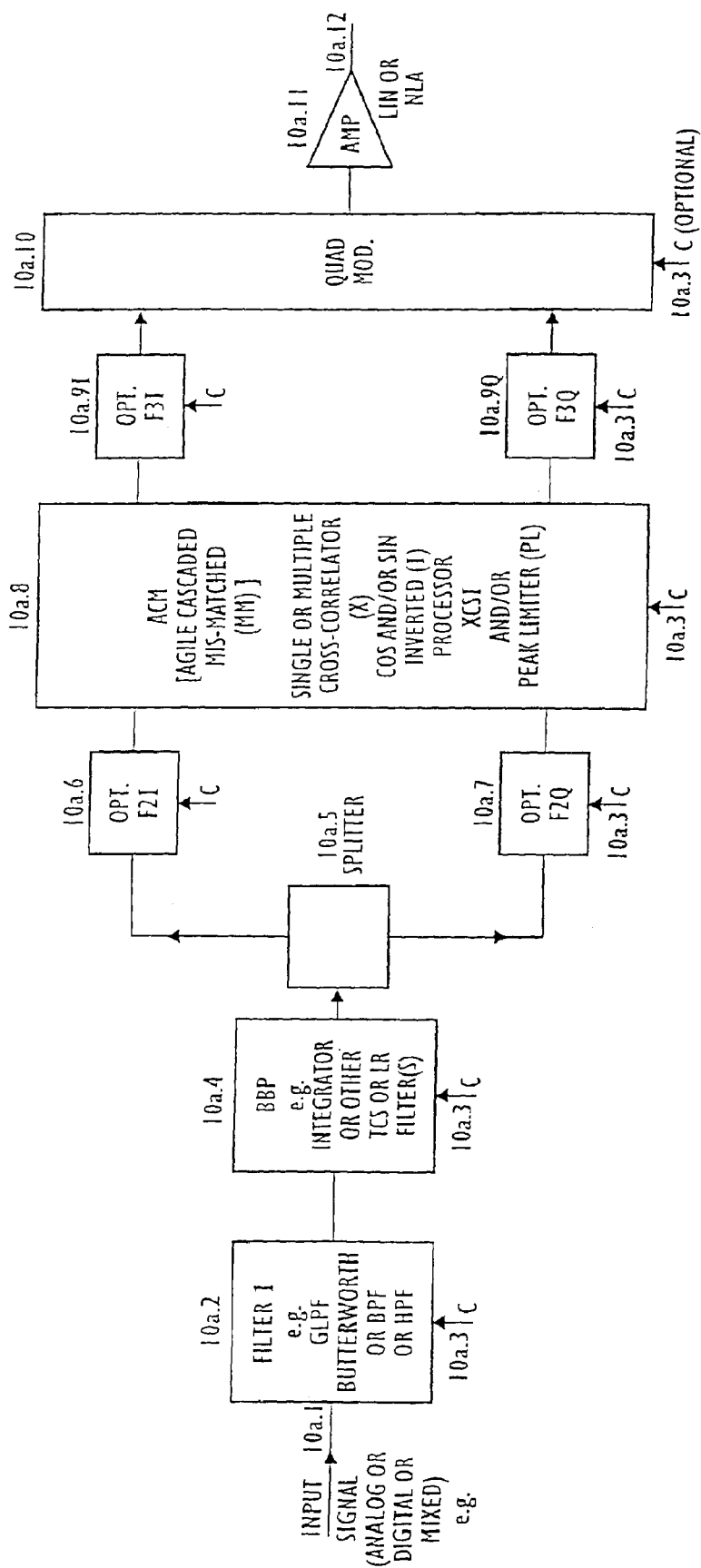
FIG. 10a shows a Cross-Correlated (Xcor) embodiment with Gaussian LPF and Integrator as well as sin and cos look-up tables. The TCS outputs of the I and Q baseband signals are further spectrally shaped and limited by sets of I and Q channel filters. A single or multiple cross-correlator (X), cos and/or sin inverter (XCSI) is used in this Agile Cascaded Mis-Matched (MM) (ACM) implementation.
Figure 10B:
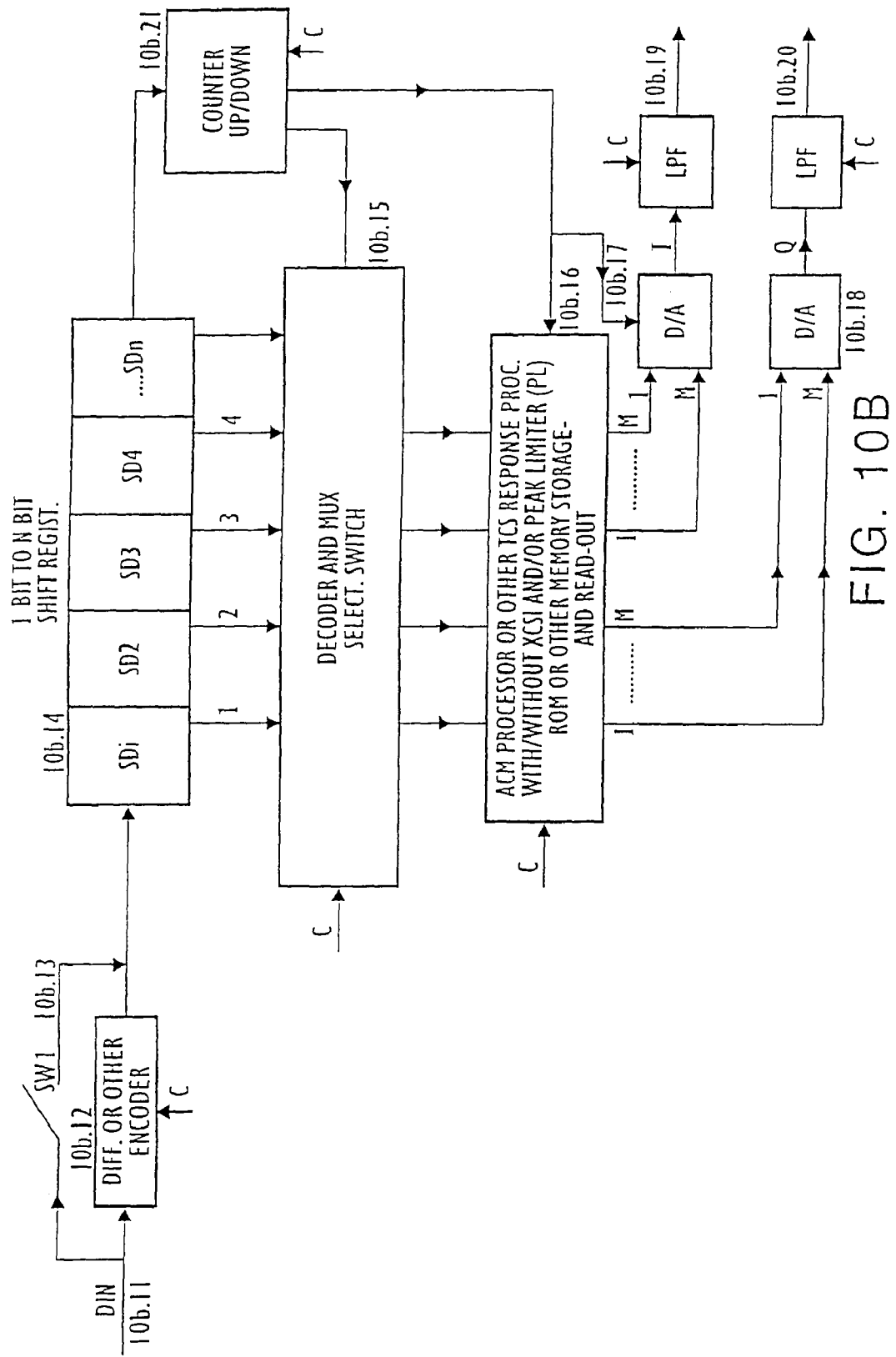
FIG. 10b shows the implementation architecture of an alternative XCSI with PL single or multiple XCSI and/or Peak Limiter (PL) processor.

A Cross-Correlated (Xcor) embodiment of this invention for a BRA architecture, and also suitable for ACM operation, is shown in FIG. 10*a*. It is suitable for several classes of FQPSK, FMOD, FGMSK, FMSK, FGFSK and FQAM implementations. The implementation includes Gaussian LPF and Integrator and/or other filter processor as well as sin and cos look-up and/or other "look up tables". BRA implementations and implementation of TCS and LR filtered/processed Cross-Correlated (CC) baseband I and Q signals and the corresponding Quadrature Modulator (QM) and RF amplifier (Amp) are included in the embodiment of FIG. 10*a*. The aforementioned term "look up tables" refers to TCS response wavelet storage and/or wavelet generation units. In alternate embodiments the sin and cos wavelet generators and/or wavelet storage and readout units are replaced with other wavelets than the aforementioned sin and cos function generated wavelets. On lead 10*a*.1 an input analog, digital or mixed signal is provided to Unit 10*a*.2 also designated as Filter 1. This filter as well as other components of the transmitter are Clocked/Controlled and/or Sampled by one or more 10*a*.3 signals, designated for short by the letter C. Filter 1, 10*a*.2 is a Gaussian shaped, Butterworth, Bessel or other filter or combination of filters and processors and it is configured in LPF, BPF or HPF mode. Unit 10*a*.4 is a second signal processor. It embodies an Integrator or some TCS signal shaping units and/or LR filter ACM implementation. Splitter 10*a*.5 splits the signal into I and Q signals and it may implement the splitter and/or Serial to Parallel (S/P) converter and variations of elements 2.10 to 2.15 and/or 2.24 to 2.33 of FIG. 2. The I and Q signals provided by the 10*a*.5 splitter output are further spectrally shaped and limited by the set of I and Q channel LPF's, designated as Filt 2I and Filt 2Q. These optional (Opt.) F2I and F2Q Bit Rate Agile Filter (BRA) elements 10*a*.6 and 10*a*.7 in FIG. 10*a* are TCS and/or Long Response (LR) filters, where the term "Long Response" refers to the typically longer pulse and/or impulse response of the LR filters than that of the TCS filters. This cascaded TCS and conventional filter approach is applicable for bit rate agile spectrum enhanced GMSK signal generations, also designated as FGMSK containing elements related to U.S. Pat. No. 5,789,402 (for short '402); however, with the new single or multiple ACM Cross-Correlated (X) Single or Multiple Cos (C) and Sin (S) and/or Inverter (I) (for short "XCSI" and/or Peak Limiter (PL) processor components of this new invention.

The second optional (Opt.) filter set is 10*a*.6 and 10*a*.7. This set provides for processing of the I and Q signals provided by 10*a*.5. The XCSI unit 10*a*.8 cross-correlates the aforementioned I and Q signals with a C driven clock/sample/control and provides for selectable amount of cross-correlation between the I and Q channels, including for a cross-correlation reduced to zero, i.e. no cross-correlation between the TCS and LR processed signals. In some of alternate embodiments of this invention there is no cross-correlation apparatus used. In units 10*a*.9I and 10*a*.9Q optional additional filtering processing is implemented by optional units F3I and F3Q. These units provide optional ACM filtered/processed BRA cross-correlated or not-cross-correlated I and Q signals to the Quadrature Modulator unit 10*a*.10 which in turn provides the signal of amplification to Amplifier (Amp) 10*a*.11 and to output port 10*a*.12 for signal transmission or broadcasting. The output port is represented by connector 10*a*.12.

Figure 11A:
FIG. 11a illustrates NRZ signal and shaped Feher Return-to-zero (FRZ) signal patterns and an embodiment having TCS response and cascade LR filters in which the LR filter is implemented with digital IIR and/or FIR filters.

In FIG. 11*a*.1*a* conventional Non-Return to Zero (NRZ) signal pattern is illustrated in 11*a*.1. In 11*a*.2 a modified Return to Zero (RZ) pattern designated as Feher Return to Zero (FRZ) data pattern is shown. Both of the NRZ and FRZ signals are Time Constrained Signals (TCS). The FRZ signal 11*a*.2 has an adjustable amount of Delay (D) for the forced transition instance from the logic state 1 to logic state 0. The FRZ signal is used in some of the TCS embodiments, 11*a*.3 while in other TCS architectures FRZ is not in use. One of the advantages of FRZ signals is that they may contain discrete spectral lines and have a more robust performance in RF time dispersive or frequency selective faded systems if used in conjunction with modulators/demodulators, including but not limited to quadrature modems. The FRZ signal contains, in some embodiments, non-symmetrical or asymmetrical rise and fall times and even pulse shapes. The TCS unit 11a.3 has as its inputs one or more signals as well as the "C" signals where C designates optional clocks, and/or sampling including over- and/or under-sampling signals and/or other control signals. The TCS processor in one of the embodiments generates Non-Cross-Correlated (NCC) signals while in another embodiment Cross-Correlated (CC) signals are generated in unit 11a.3. In the case of digital processing such as FPGA and/or ROM and/or RAM, digital implementations D/A converter(s) 11a.4 are provided. In one of the embodiments a single D/A is implemented. The single D/A is providing time shared or time multiplexed signals as I and Q inputs for Quadrature Modulation (QM). Prior to QM an optional analog processor and/or filter with possible BRA clocked operation, 11a.5, is implemented. The QM 11a.6 provides BRA quadrature modulated signals to optional amplifier or cascaded amplifiers 11a.7 which could operate in a linear mode or partly linearized mode or in a fully saturated NLA power efficient mode. The aforementioned amplifier provides the signal to the Antenna 11a.8 or alternatively to the output port 11a.9 for signal transmission.

Figure 11B:
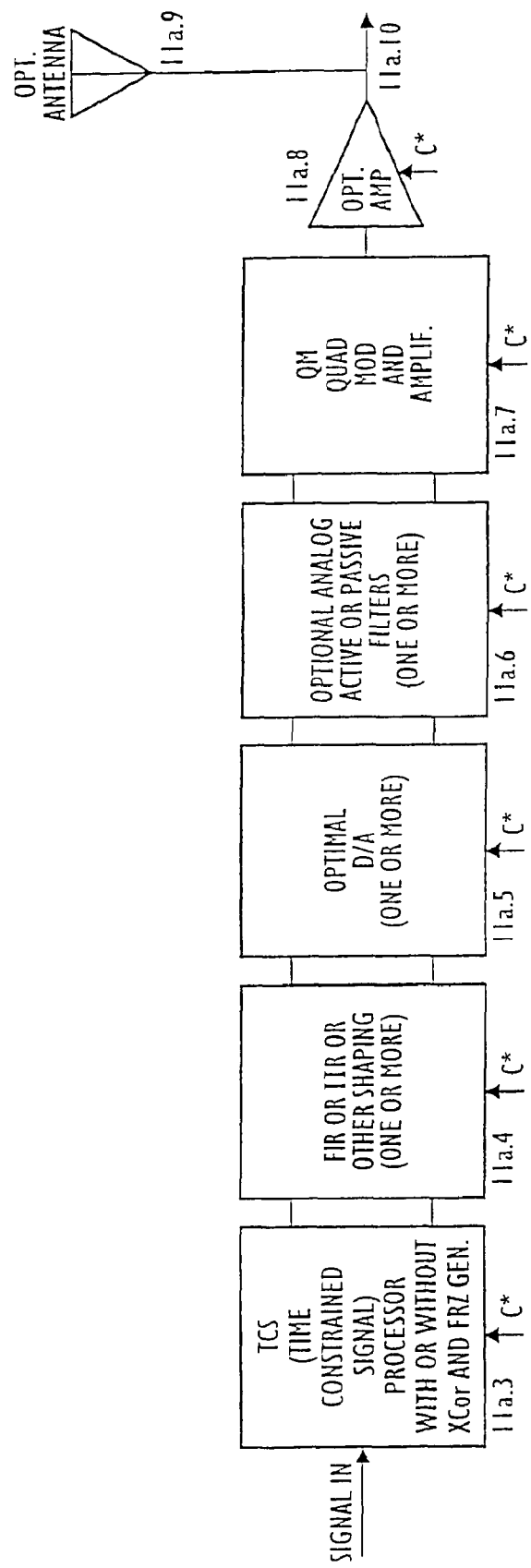
FIG. 11b shows a pre-processor based architecture of a BRA system with single or multiple Signal Element (SE) storage and/or inverter and of single or multiple D/A based architecture having selectable 1 to N filter channel banks.
Figure 11C:
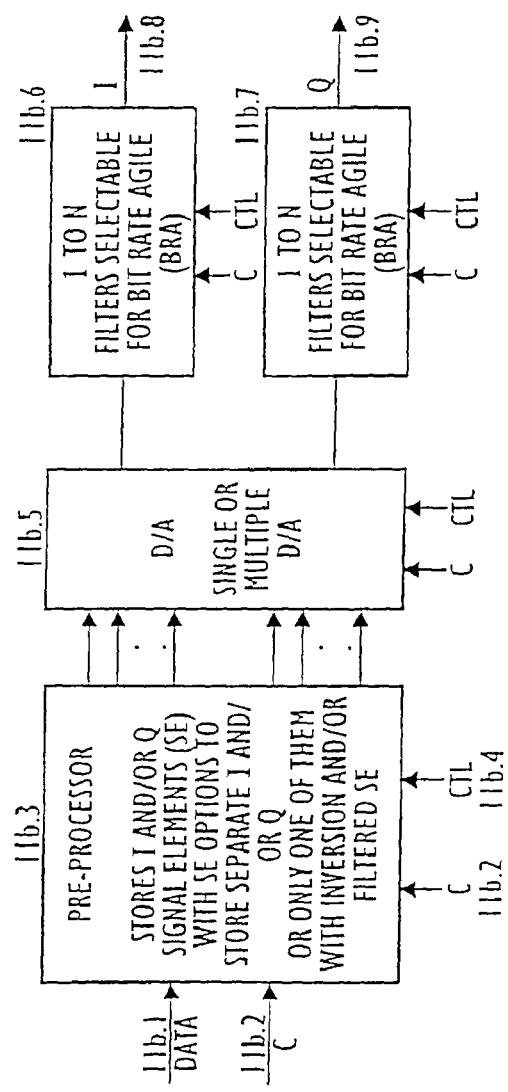
FIG. 11c shows an implementation of a Bit Rate Agile (BRA) pre-processor with single or multiple wavelets Signal Element (SE) storage and/or inverter and of filtered SE and ACM processors.

An alternate embodiment is shown in FIG. 11b. The implementation of a Bit Rate Agile (BRA) pre-processor with single or multiple wavelets (also designated as) Signal Element (SE) storage and/or inverter and of filtered SE and ACM processors is illustrated. On leads 11b.1 and 11b.2 respectively the Data Inputs (DI) and Clock (C) inputs are shown. Here the terms "Data Inputs" are synonymous with one or more digital or analog or hybrid combined digital/analog signals having 2 or more signaling states. The term "Clock" or for short "C" is synonymous with one or more clock signals, sampling and control signals as mentioned elsewhere in this disclosure. Pre-processor 11b.3 stores I and Q Signal Elements (SE) for BRA operation optionally controlled and/or clocked/sampled by the 11b.2 and 11b.4 signals/clocks. The pre-processor unit 11b.3 stores in one of the embodiments a large number of separate and distinct Signal Elements (SE), also designated as "wavelets", and provides the selected SE in appropriate order to the 11b.5 single or multiple D/A converter(s). The D/A converter (S) provides to unit(s) 11b.6 and/or 11b.7 I and Q signals for further BRA operation. Selectable filters designated as 1 to N and/or a bank of filters are used in one of the ACM embodiments of 11b.6 and 11b.7 and provide the I and Q signals to ports 11b.8 and 11b.9.

Figure 12A:
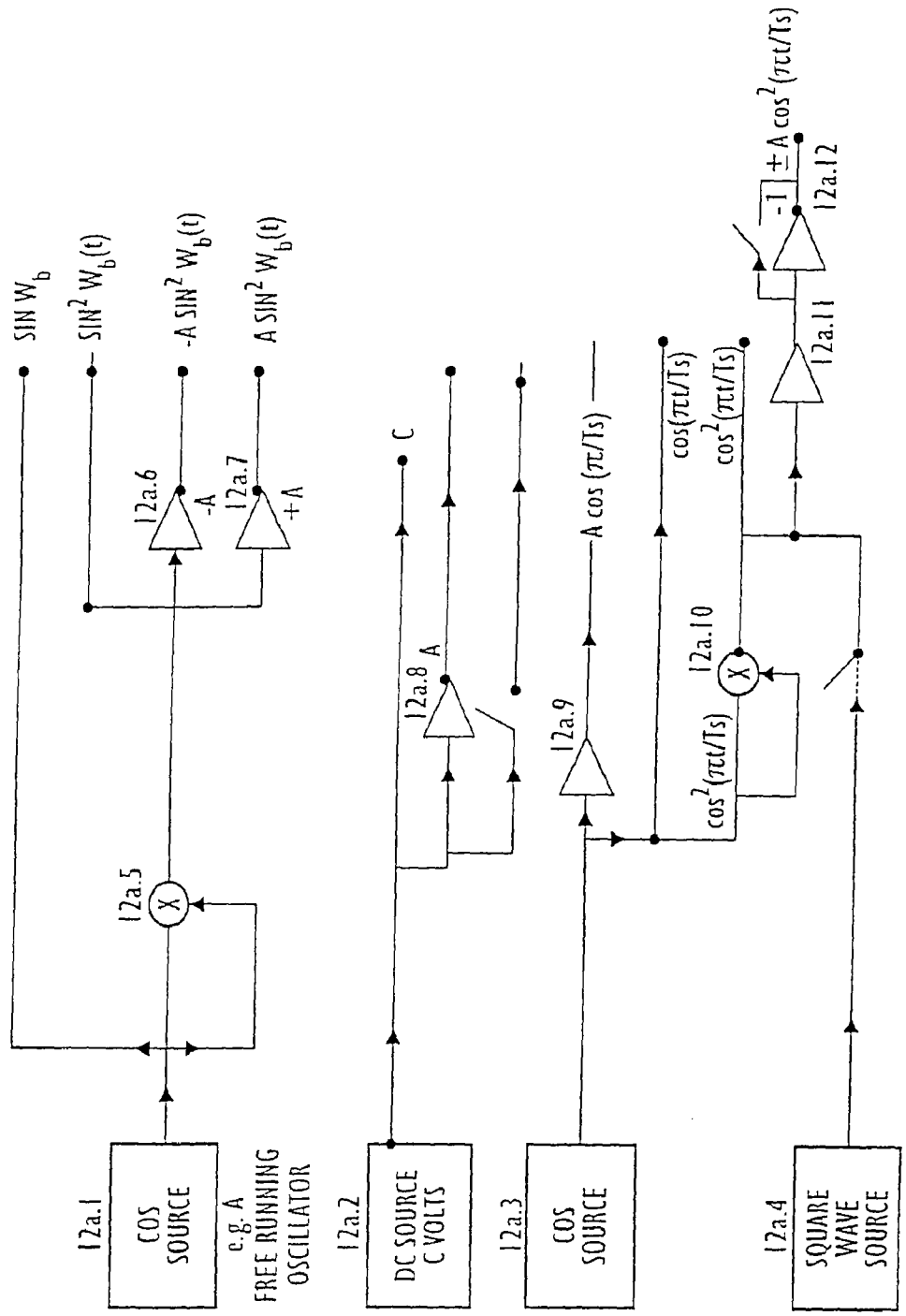
FIG. 12a analog implementation components for cross-correlated and/or TCS-filtered data patterns and signals for bit rate agile and for high bit rate applications are shown.
Figure 12B:
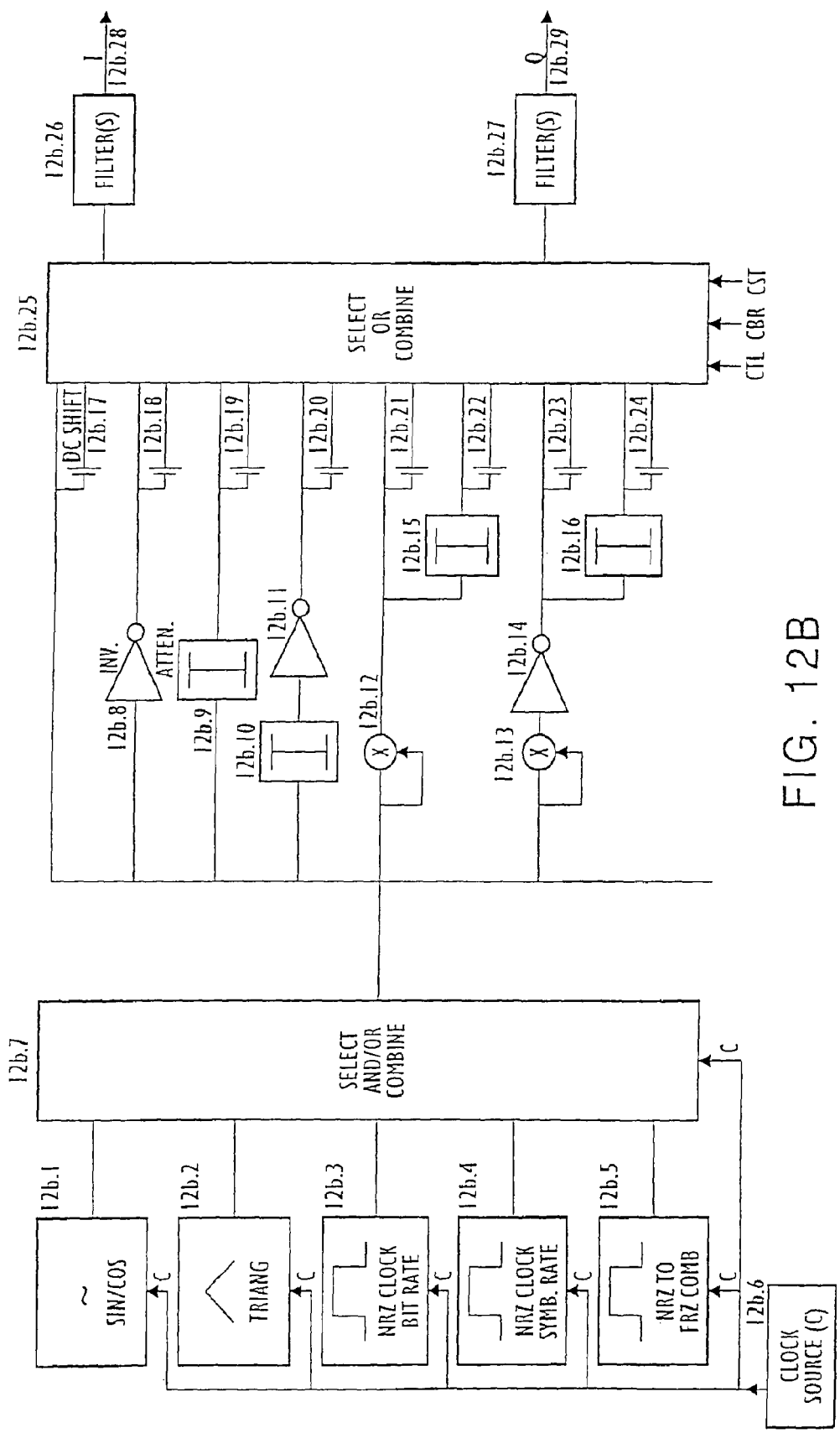
FIG. 12b shows an analog BRA baseband implementation alternative of a TCS response processor for cross-correlated or not cross-correlated I and Q signals with selection or combined cascaded LR filter embodiment of this invention.

In FIG. 12, including 12a and FIG. 12b predominantly analog components used in analog implementations and embodiments of this FQPSK and related transceiver embodiments are shown. In addition to some of the active components depicted in these figures, embodiments of the virtually same functions as those with analog components are implemented with passive analog components. The individual components are conventional off-the-shelf available components described in detail in prior art publications including patents and detailed descriptions of these components are superfluous. In particular in FIG. 12a analog implementation components for cross-correlated and non-cross-correlated BRA processed TCS and/or LR filtered and/or ACM signals are shown. In FIG. 12a unit 12a.1 is a "COS" that is cosine or sine wave generator. One of the well-known embodiments of 12a.1 is a readily available analog Free Running Oscillator (FRO). Unit 12a.2 is a "Direct Current" (DC) source while 12a.3 and 12a.4 represent an alternate COS source and a Square Wave Source, respectively. Even though COS and SIN sources are illustrated as separate components, embodiments include single source COS or SIN sources/generators which may be converted to Triangular Square Wave or other periodic or non-periodic sources. The aforementioned signal sources or signal generators are connected in a variety of configurations such as the exemplary embodiments of FIG. 12a and FIG. 12b to components such as multipliers, amplifiers, switches, attenuators, inverting amplifiers and "DC shift" units 12a.5 to 12a.12 for processing and providing signals for further processing including selective switching or combining.

In FIG. 12b another analog BaseBand (BB) embodiment using predominantly analog components is illustrated. Units 12b.1 to 12b.5 are signal sources such as previously described. Unit 12b.6 is a previously described clock/sample/controlled source abbreviated with the letter C. Unit 12b.7 provides selection and/or combinations and permutations of the signal sources with amplitude adjustments of the aforementioned signal sources which operate at the same rate in some embodiments and operate in asynchronous non-related bit rates to each other in other embodiments. Unit 12b.7 provides one or more signals to standard and readily available components such as 12b.8 to 12b.24. These components provide inputs to the "select" or "combine" unit 12b.25 which has at its input optional Control (CTL), Clock Bit Rate (CBR) and Control Sampling Time (CST) signals. One or more of these signals, by itself or in combination, may constitute multiple inputs and are synonymously further abbreviated and designated as "C" in several parts of this invention. Units 12b.26 and 12b.27 provide further signal processing for the outputs of 12b.25 and generate I and Q output signals.

Figure 13A:
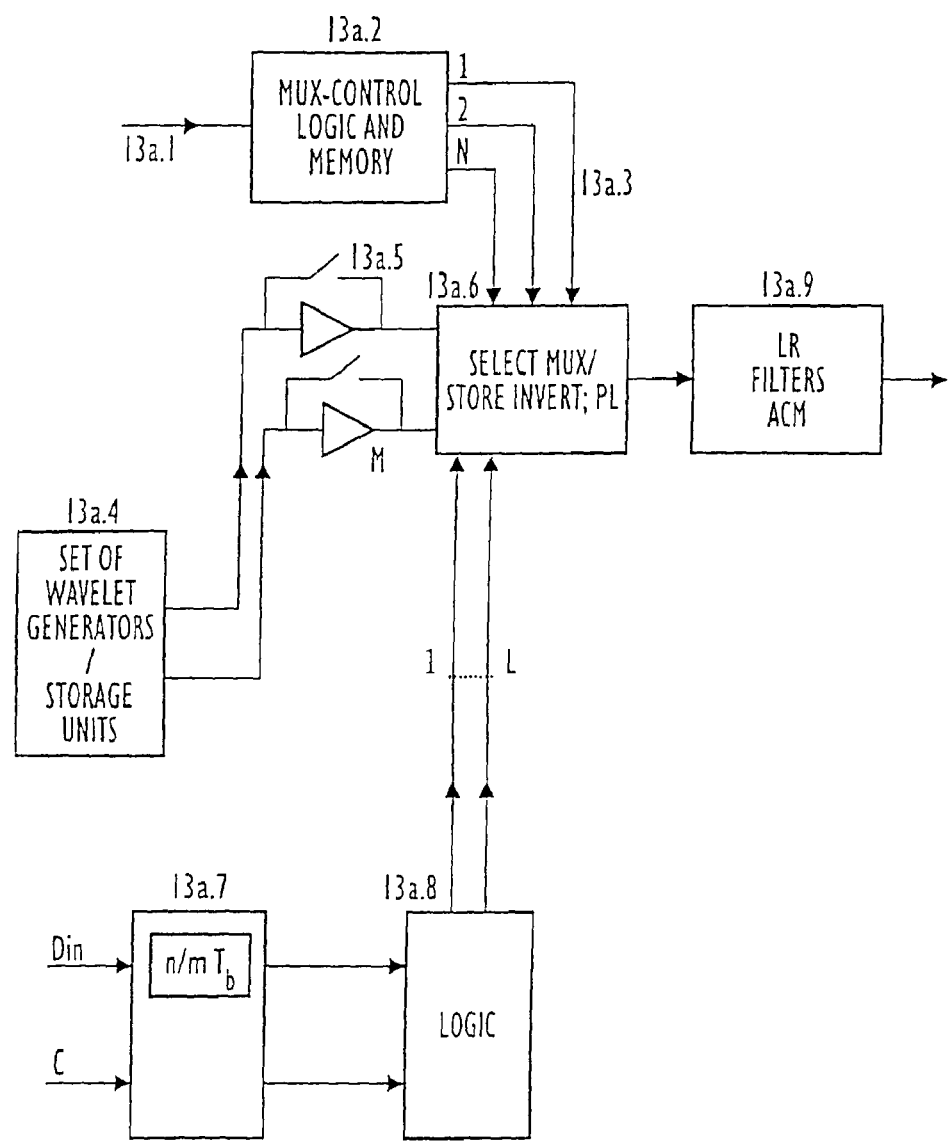
FIG. 13a is a mixed analog and digital circuit implementation alternative of this cross-correlated TCS response processor in cascade with LR filters.
Figure 13B:
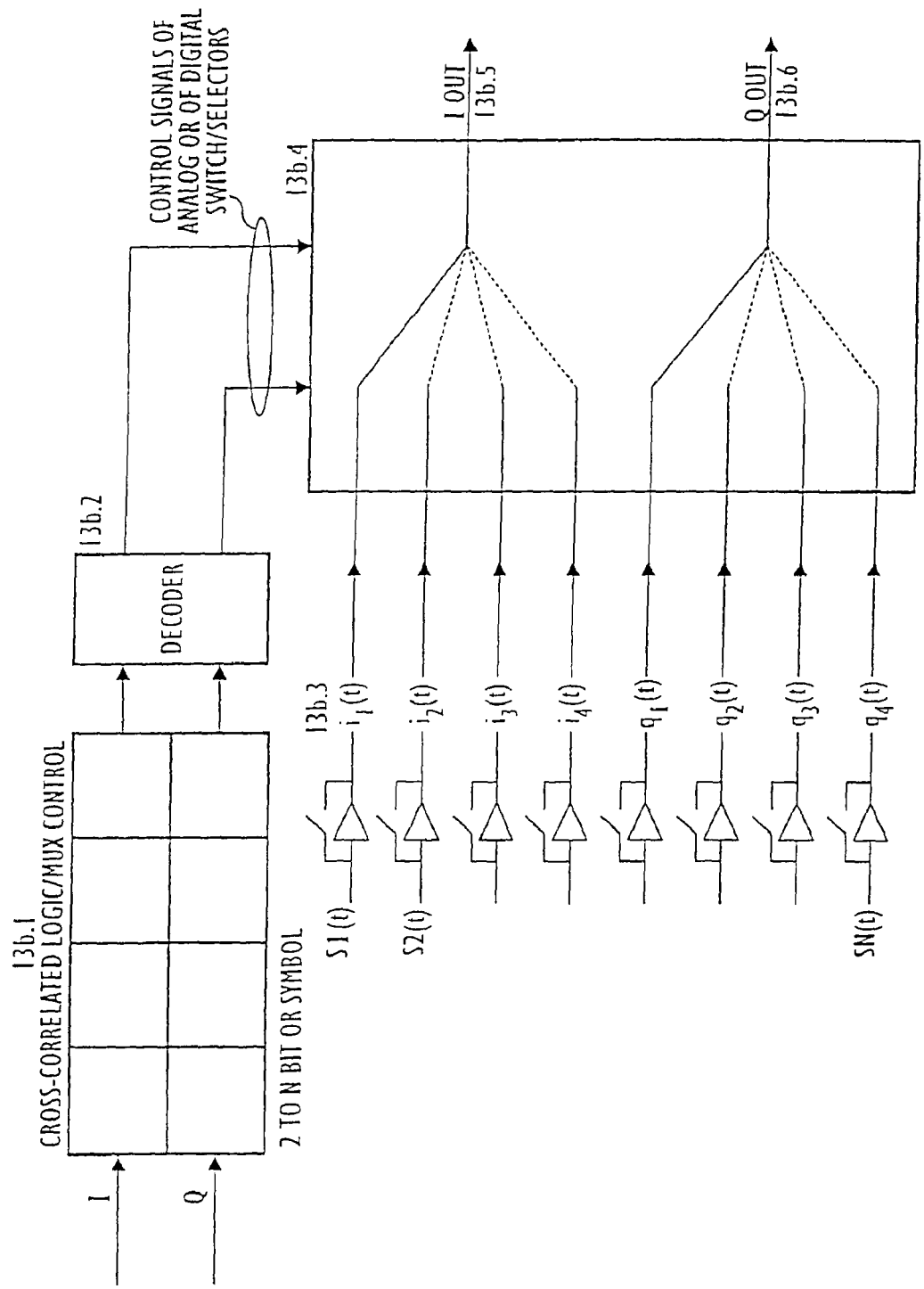
FIG. 13b shows an other alternative implemented cross-correlated system with a combination and/or selection of analog and digital circuits.
Figure 13C:
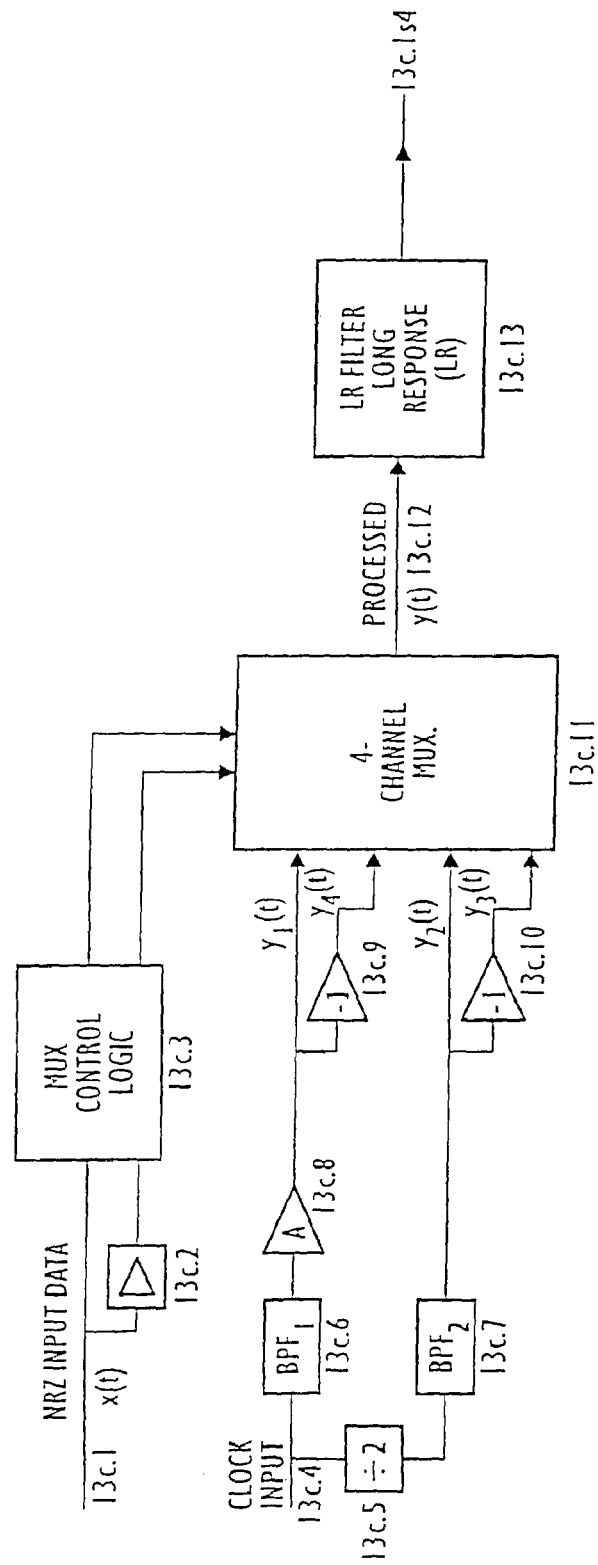
FIG. 13c shows a detailed implementation structure for one of the channels (I or Q) of a TCS response processor in cascade with a LR filter. In some embodiments the TCS processor contains cross-correlation between the I and Q channels while in other implementations there is no cross-correlation between the TCS response and cascaded LR filtered signals.

In the embodiment of FIG. 13a an implementation comprising mixed analog and digital circuit components is shown. On lead 13a.1 the data input or DIN provides two 13a.2 signals for multiplexing control/logic processing and memory. In one of the embodiments, logic processing and memory storage/processing converts the input signal to a Trellis Coded (TC) baseband signal. Control signals present on leads 13a.3 serve as one of the inputs to the N by M (N×M) channel multiplexer and cross correlator and/or other TCS unit 13a.6. Analog inputs of 13a.6 could be generated by unit 13a.4 and further processed by analog components such as the set of components 13a.5 of this particular embodiment. Units 13a.7 and 13a.8 provide additional digital timing bit rate and sample clock scaling, n/m rate division and miscellaneous logic functions embodied by standard logic gates and/or DSP and/or Analog Signal Processing (ASP) components.

Figure 14A:
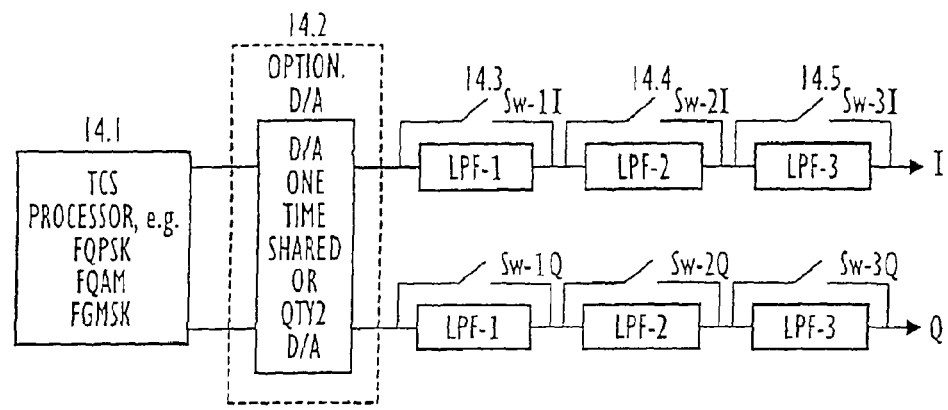
FIG. 14 shows a BRA implementation alternative with a TCS processor, one or more D/A devices in cascade with a bank of switchable LR filters/processors and switchable Linearized Phase or Phase Linear (PL) and Not Linear Phase (NLP) Filters.
Figure 14B:
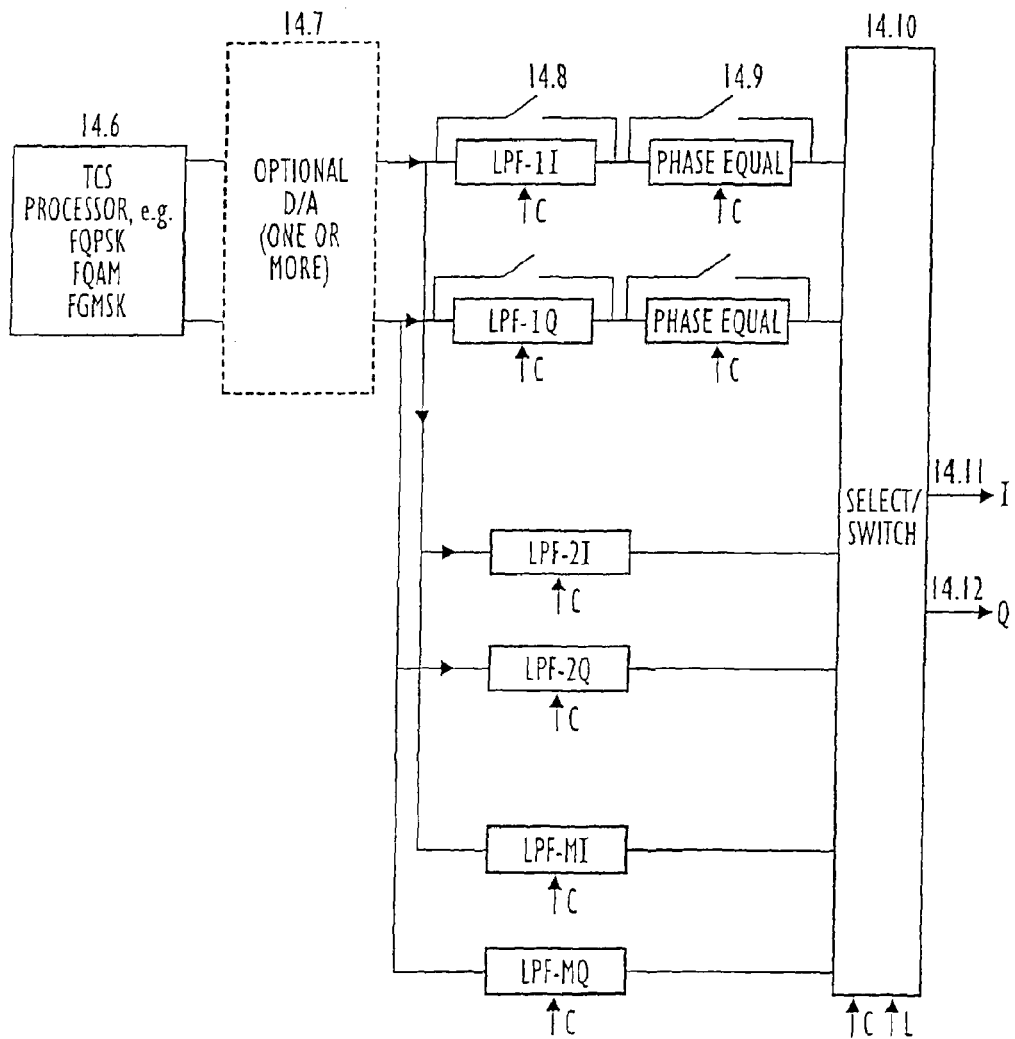

FIG. 14 shows an alternate design of the current invention including a bank of switchable filters/processors with Linearized Phase or Phase Linear (PL) and Not Linear Phase (NLP) Filters. Phase Linearization Components may be entirely deleted or, if included in this implementation, they may be switched in and out in this hybrid analog and digital transmit implementation of the transmitter. Unit 14.1 is the embodiment of a TCS processor for time constrained signals with or without cross correlation implemented for FQPSK or FGMSK or FQAM or FMSK or related BRA signals. The output(s) of the 14.1 TCS processor provides one or more signals to the optional D/A unit 14.2. The outputs of the single or multiple D/A or of 14.1, in case 14.2 is not used, are provided to the cascaded I and Q filters and Switches 14.3 to 14.5. While the filters are indicated as LPF-1 to LPF-3, they have been implemented as low-pass, band-pass and high-pass filters providing the LR pulse response with or without phase equalization. These filters may be designed for Agile Cascaded Mis-Matched (ACM) systems. An alternate embodiment comprises TCS unit 14.6 connected through optional D/A unit(s) 14.7 to the bank of 14.8, 14.9 and 14.10 selectable or combined switched phase equalized or non-phase equalized parallel and/or cascaded units LPF-1I, LPF-1Q to LPF-M1 and LPF-MQ filters. On output ports 14.11 and 14.12 the processed I and Q signals of the aforementioned particular embodiment of this invention are available for further processing.

Figure 15:
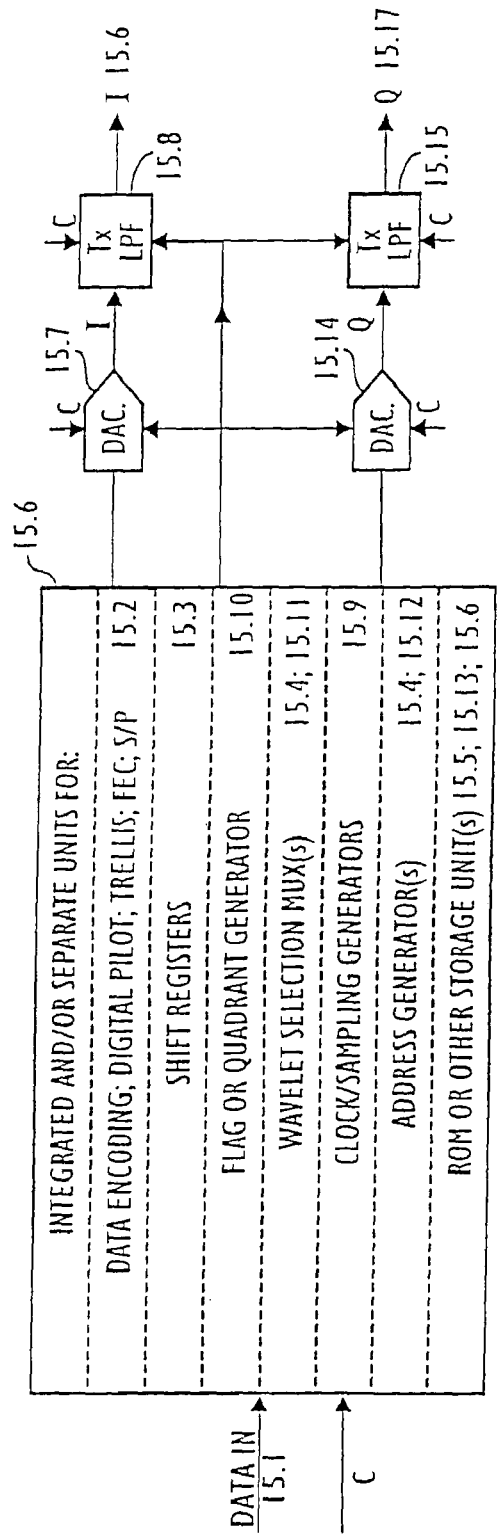
FIG. 15 is a detailed implementation diagram alternative of this ACM mode architecture having cross-correlated TCS response wavelet generators in cascade with LR filters.
Figure 16A:
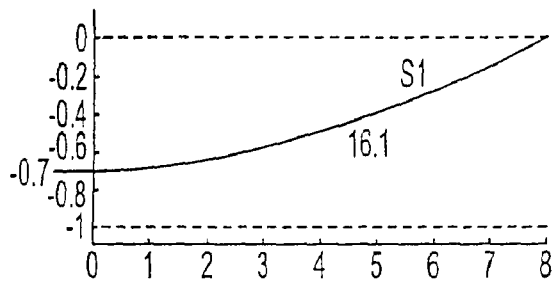
FIG. 16 shows four (4) illustrative signaling elements generated by analog TCS response cross-correlators, prior to the cascaded LR filters. The shown signaling elements or wavelets are for FQPSK signal generation, having a cross-correlation parameter of A=0.7.
Figure 16B:
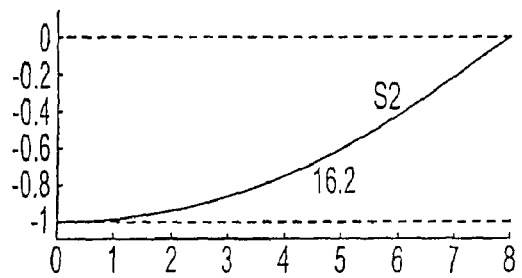
Figure 16C:
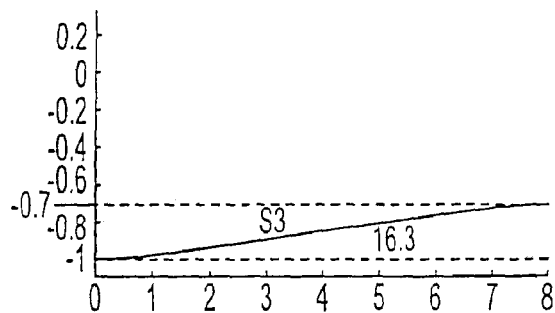
Figure 16D:
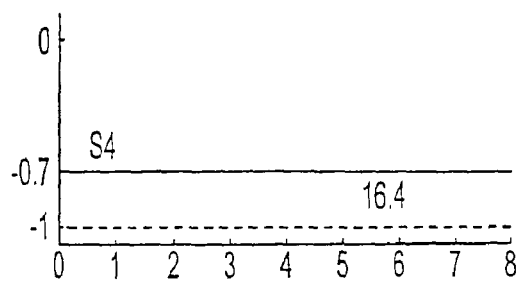
Figure 17A:
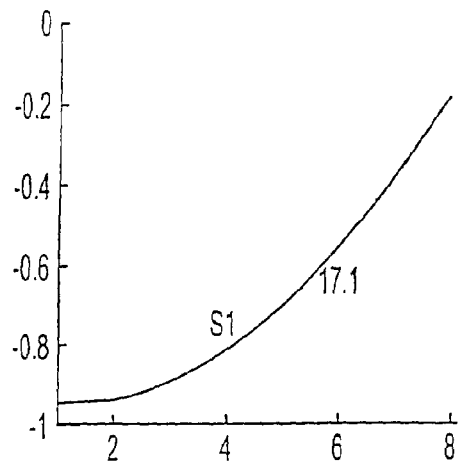
FIG. 17 shows four (4) cross-correlated BRA signaling elements of one of the TCS response analog generated circuits for enhanced performance FGMSK. Only 4 signaling elements are required in this BRA reduced spectrum Feher Gaussian Minimum Shift Keying (FGMSK) signal generation, having a BTb=0.5 parameter.
Figure 17B:
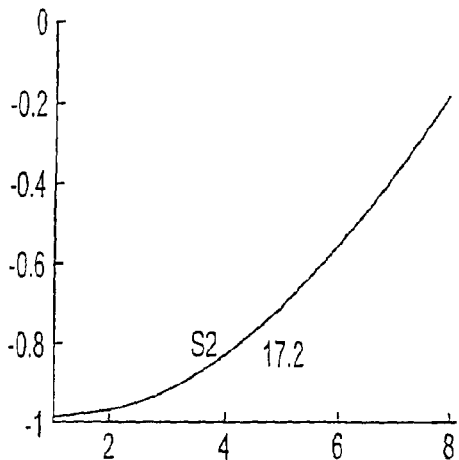
Figure 17C:
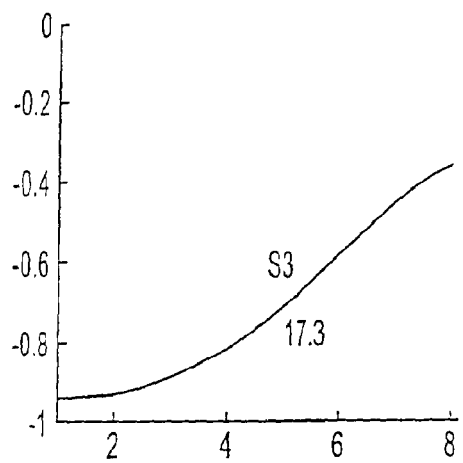
Figure 17D:
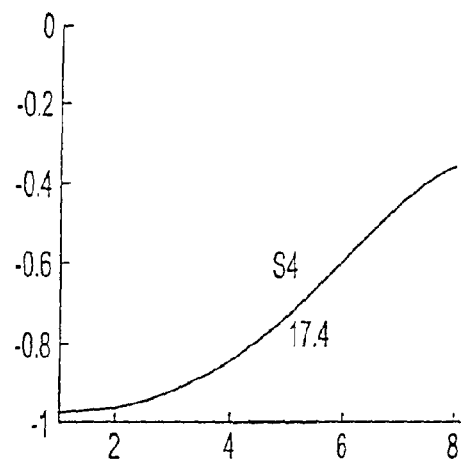

In FIG. 15 one of the predominantly digital BRA and ACM alternative implementations is shown. The embodiment of digital processor based implementation, followed by one or more D/A converters and BRA Long Response (LR) filters are shown in the architecture of FIG. 15. The block diagram of FIG. 15 is an alternative embodiment of this invention having a TCS signal generator in cascade with the $2^{nd}$ processor set of bandwidth spectral shaping LR filters. The LR filters are designated as LPF. The embodiments include analog and digital LR filters including combination and selections between LPF, BPF and HPF and other analog or digital filters. Data encoder 15.1 has at its input the "Input Signal" and the "C" signals. For simplification reasons of this and some other figures of this invention, the C signals are not always drawn on the respective figures and are not connected in the diagrams to all of the possible inputs. Following data encoding, implemented by conventional digital and/or analog components and/or DSP and/or software or firmware, the signals are provided to an encoding/logic processor which could contain a Shift Register (SR) unit 15.2. A flag generator provides one of the output bits to waveform select logic 15.4 for processing. Address generators 15.6 and 15.9 provide addressing information to ROM units 15.5 and 15.6. The ROM units are sampled and their content read out to DAC (Digital to Analog Converters) 15.7 and 15.14. The outputs of the DAC units are provided to units 15.8 and 15.15 for further filtering and providing the output signals to ports 15.16 and 15.17, the ports for the I and Q signals, respectively.

In one of the alternate Field Programmable Gate Array (FPGA) based implementations of the TCS processor of FQPSK and FGMSK readily available Xilinx Chip Model No. SC4005PC84-6 has been used. While in an other embodiment Xilinx SC4000FPGA was used. Other implementations used Alterra and Intel devices. The wavelets used in one of the designs used 16 samples for 1 symbol time Ts duration while in an other embodiments used only 4 samples for 1 symbol time Ts. Each sample was encoded in one of the implementations into 10 bits/sample with D/A converters having 10 bit resolution, in other cases 4 bits/sample were used.

In one of the embodiments of FIG. 15, a data encoder, 4-bit shift register, I and Q waveform select logic, address generators based on ROM implemented components, D/A converters, Clock and Sampling Generators and output latches are used. This particular design does not use a half-symbol physical delay component in one of the (I or Q) baseband channels. Rather, the half-symbol offset between the I and Q channel output waveforms is obtained by appropriate waveform selection procedure.

In FIG. 16 "Wavelets" or Basic Signaling Elements (SE), for FQPSK designated also as "Wavelets" and/or "Signal Components" or merely "Signals" are shown. This FIG. 16 depicts TCS Wavelets for enhanced performance FQPSK signal generation with a Cross-Correlation of A=0.7 and in particular for TCS wavelets with only four (4) signaling elements required for storage—suitable for high speed and integrated TCS and cascaded filter LR processing solutions. The appropriately assembled I and Q cross-correlated TCS sequence is provided to BRA Long Response (LR) filtering of I and Q channels. Signals 16.1, 16.2, 16.3 and 16.4 in FIG. 16, also designated as S1, S2, S3 and S4, are illustrated across one symbol interval. For 4 signaling state systems one symbol corresponds to two bits, thus Ts=2Tb in duration. The S1 to S4 signals could be sampled and stored 4 times per symbol, i.e., 2 times per bit or at other sample intervals. The sampled signal wavelet values are stored in architectures containing memory devices. Signal element or "wavelet" S4, designated as 16.4, is simply a DC component in this particular embodiment. In some of the TCS embodiments S1 to S4 are cross-correlated between the I and Q channels and have continuous derivatives at the signal transitions, while in other embodiments the TCS signals are not Cross-Correlated. Alternate embodiments have a more or lesser number of wavelets than illustrated in FIG. 16.

Figure 19B:
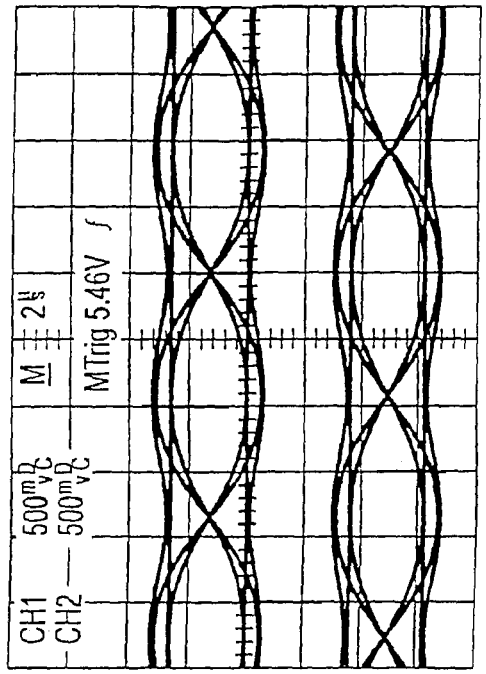
FIG. 19 eye diagrams of DE prototype BRA transmit signals for FGMSK with BTb=0.3, and FQPSK with a cross-correlation parameter A=0.7, prior to additional baseband processing and prior to the baseband LR filter of the transmitter are shown. The eye diagram at the TCS response processor output and the I and Q cross-correlated eye diagrams, at the outputs of the cascaded TCS response and LR filters of FQPSK-B systems, operated in ACM mode, as well as the corresponding vector constellation diagrams are also shown.
Figure 19A:
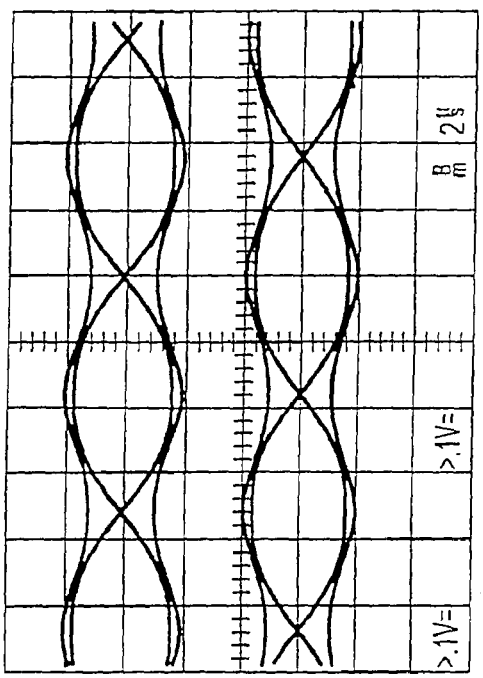
Figure 19C:
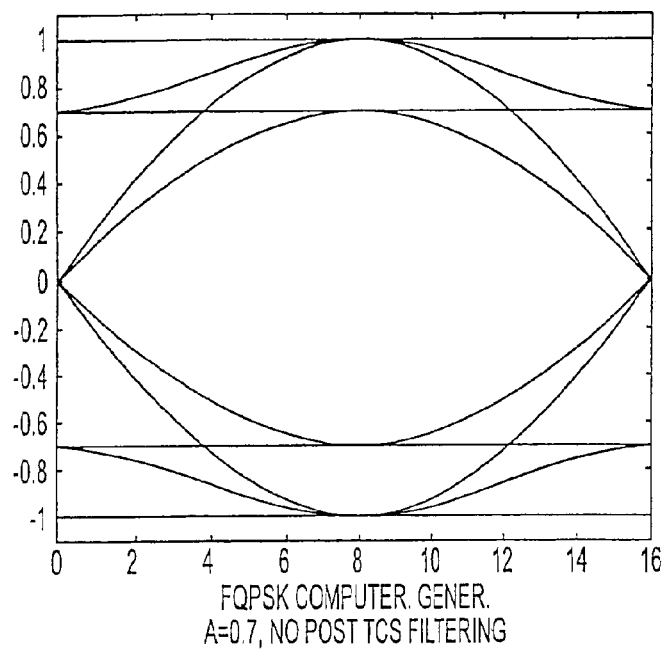
Figure 19D:
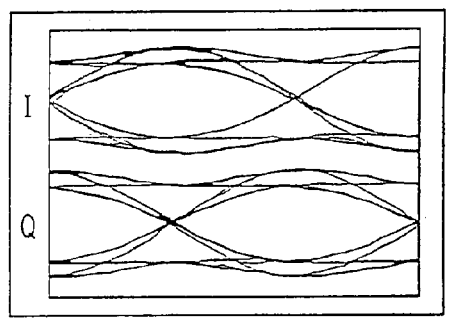
Figure 19E:
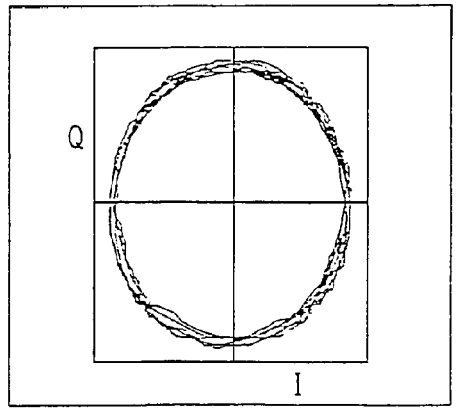

An implementation of FQPSK baseband signal processor's taking advantage of inverse and symmetrical properties of its waveforms is described in this section related to previously described figures and embodiments and in particular in relation to FIG. 15, FIG. 16 and FIG. 17. Instead of the storing all the basic entire or whole "Wavelets" of the baseband signals, one of the implemented designs with ROM lookup table uses only 3 "basic" wavelets. To simplify the implementation of cross-correlated FQPSK baseband signals, we use the symmetry properties of the wavelets and the hold function for DC value. In the design there is a half-symbol delay between the I and Q channels so that the ROM contents in I and Q channels are the same. FQPSK and FGMSK eye diagrams at the TCS output and also at the cascaded TCS and LR filters are shown in FIG. 19. As a specific design and teaching example the TCS generated eye diagram of an FQPSK signal with an A=0.707 cross-correlation parameter is shown in FIG. 19(c). Such an eye diagram is measured and/or computer generated at the output of the embodiments shown in FIG. 10 or FIG. 11 and/or other disclosed embodiments, including at the outputs of the LR filters in BRA operation of the implementation of FIG. 15, provided that the D/A converter has a good resolution accuracy e.g. 8 bits/sample and that the LR filter units 15.8 and 15.15 of FIG. 15 have a considerably higher cut-off frequency than the inverse of bit rate. It can be seen that in the FQPSK eye diagram of FIG. 19(c) there are 10 kinds of waveforms or wavelets during half-symbol duration (from 0 to 8 or 0 to Ts/2). Thus it is possible to pre-calculate the waveforms directly from the input data. FIG. 15 shows one of the implementation architectures of the designed FQPSK baseband processor using this approach. In FIG. 16 the 3 half-basic waveforms needed to generate all the possible TCS response wavelets for FQPSK are shown. Based on the symmetry and inverse properties of the whole set of the wavelets illustrated in FIG. 19(c), instead of 10 only 3 waveforms plus a DC value (holding function for DC value) are required. In this design, 4 samples/symbol (or 2 samples per bit) are used to implement the waveforms of FQPSK.

In FIG. 17, BRA "Wavelets" for FGMSK are shown. These Gaussian wavelets are suitable for smaller size memory implementations, for bit rate agile GMSK signaling having a BTb=0.5 parameter. This FIG. 17 depicts TCS Wavelets for use in LR filtered enhanced performance reduced spectrum BRA systems. Only four (4) signaling elements are required in this embodiment of the TCS part of the FGMSK processor. With the embodiment of FIG. 15 and other alternate digital and/or analog embodiments these signals can be easily generated even at very high bit rates. The appropriately assembled I and Q cross-correlated TCS sequence is provided to BRA Long Response (LR) filtering of I and Q channels. In FIG. 17 the signals 17.1, 17.2, 17.3 and 17.4, also designated as S1, S2, S3 and S4, are illustrated across one symbol interval. For 4 signaling state systems one symbol corresponds to two bits. Thus, Ts=2Tb in duration. The S1 to S4 signals could be sampled and stored 4 times per symbol, i.e., 2 times per bit or at other sample rates. The sampled signal wavelet values are stored in architectures containing memory devices such as the previously disclosed ROM based embodiments. The FGMSK signal shapes have different shapes from the S1 ... S4 signals illustrated in FIG. 16. In some of the embodiments for use in FGMSK the S1 to S4 wavelets are cross-correlated between the I and Q channels. In other embodiments for FMSK the signals are not cross-correlated, or have different cross-correlation algorithms and embodiments than in FGMSK and/or have continuous derivatives at the signal transitions. Alternate embodiments have a larger or smaller number of wavelets than illustrated in FIG. 16 and in FIG. 17.

In FIG. 18 Differential Encoding (DE) and Differential Decoding (DD) of FQPSK and FGMSK is shown. A difference between the DE of this bit rate agile FGMSK encoder from that of conventional GMSK is in the algorithm difference of these two DE and Corresponding Differential Decoding (DD) embodiments. The new DE for FGMSK is fully compatible and interoperable with conventional OQPSK; the DE of prior art bit rate agile GMSK is not.

Eye diagrams shown in FIG. 19 are hardware measured and computer generated diagrams for Cross-Correlated BRA signals at various measurement/display points. The eye diagrams of DE prototype BRA apparatus transmit signals are presented. In FIG. 19(a) FGMSK eye diagrams of I and Q baseband signals with BTb=0.3 are shown prior to the LR cascaded performance enhancement I and Q filters. In FIG. 19(b) eye diagrams of I and Q baseband signals of an FQPSK transmitter, operated in a BRA mode having a cross-correlation parameter A=0.7 after the BRA processor LR filters (I and Q filters) are shown. In this case the LR filters have a relatively high cut-off frequency relative to the symbol rate. In FIG. 19(c) an FQPSK computer generated eye diagram is illustrated. The I channel eye is shown, for a Xcor. Parameter A=0.7 prior to LR filters. The eye diagram contains only four (4) basic wavelets and represents a TCS eye pattern In FIG. 19(d) hardware measured FQPSK eye diagrams of I and Q signals are shown for a BRA operation displayed after the LR filters of the I and Q Channels. This particular FQPSK is designated as an FQPSK-B and it has a Xcor parameter A=0.7 followed by I and Q post TCS Low-Pass Filters having LR characteristics. In FIG. 19(e) the measured vector constellation of an FQPSK-B signal after the LR filters processors of an implemented prototype system is shown.

Description of Multi-State FQPSK, FQAM, FGMSK and FMSK

In this section of the detailed description of this invention the focus is on Quadrature Modulated (QM) multiple signaling state (for short "state") systems with more than 4 signaling states of the QM signal and more than 2 states in the respective I and Q baseband channels. In the previous section the focus was on the description of QM four (4) state FQPSK systems. These four-state systems have, in general, in the I and Q baseband channels 2 signaling states (for short "states") in the I channel and 2 states in the Q channel. Most implementations and embodiments of the 4-state systems apply to multi-state (more than 4-state) Quadrature Modulated systems, described in this Section, such as 9, 16, 49 or 64 or 256 state QM systems having 3, 4, 7, 8 and 16 states in their respective baseband channels. The technologies and embodiments described for the multiple state systems are also applicable for the implementations and embodiments of 4-state systems. Forward and Backward COMPATIBILITY and/or interoperability between the 4-state and, more than four-state, multiple state FQPSK and Feher's Quadrature Amplitude Modulation (FQAM) and multi-state FGMSK and FQPSK systems is a definitive advantage in new product developments. Additionally some of these systems are also backward compatible with the previously patented Feher BPSK (for short FBPSK and FMOD) systems, such as disclosed in [P1] and [P2] and the references in the aforementioned U.S. patents and cited references.

Figure 20:
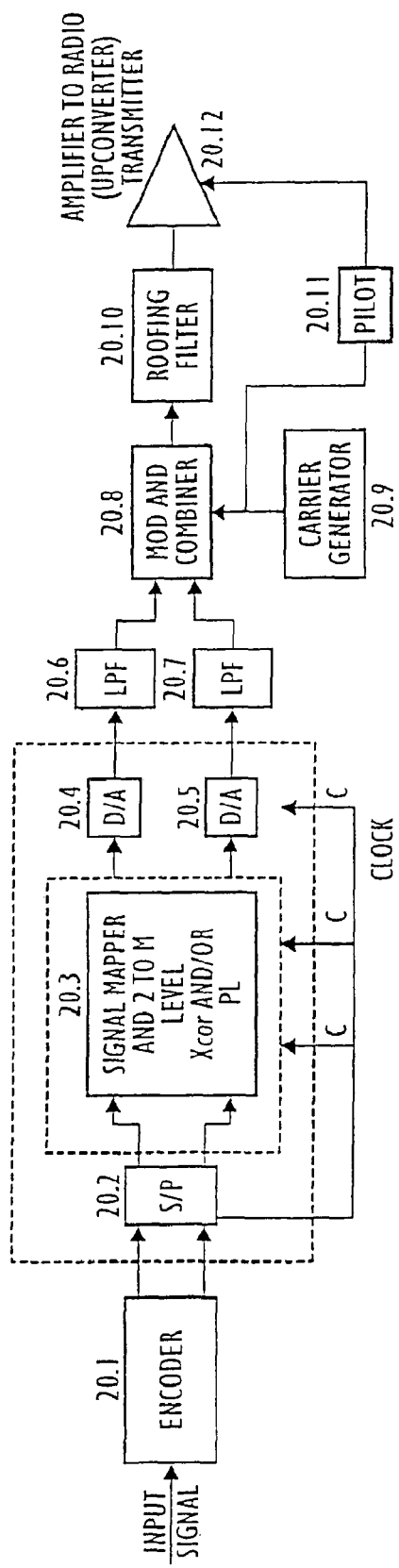
FIG. 20 shows an FQAM implementation architecture diagram for multi-state Cross-Correlated FQPSK transmitters, also designated as FQAM. In this embodiment a single RF Amplifier operated in fully saturated NLA mode is used.

A multi-state QM architecture for 4 or more than 4 states, designated as FQAM is illustrated in the embodiment of FIG. 20. In this implementation block diagram of an FQAM multi-state Cross-Correlated BRA Transmitter a single RF Amplifier operated in fully saturated NLA mode or Linearized (Lin) mode of operation is used. The Input Signal is connected to an optional Encoder unit 20.1. This unit, if used includes logic processing and Encoding functions such as Trellis Coding or CRC or FEC or DE or Gray Coding, Serial to Parallel conversion and/or other digital processing functions. In one of the embodiments an optional S/P (Serial to Parallel) converter, unit 20.2 is included to process the signals received from 20.1. The Signal Mapper 20.3 maps the binary signals from 2 states to M states (levels) and includes in some of the embodiments Cross-Correlation between the binary and/or between the converted multi-state signals. The outputs of the Signal Mapper TCS unit 20.3 are connected to D/A converters 20.4 and 20.5. The D/A Cross-Correlated BRA signals are TCS multilevel Cross-Correlated signals with variable and/or presetteable Xcor. In alternate embodiments no cross-correlation between the I and Q signals is implemented. The D/A outputs are fed to 20.6 and 20.7 filters, indicated in the drawing as LPF. These filters are LR filters and are implemented with IIR digital or IIR analog filters or a combination of conventional analog or digital filters. The BRA signals, which have been Cross-Correlated and are TCS in cascade with LR signals are provide to the inputs of Quadrature Modulator (QM) 20.8. The QM has an unmodulated Carrier Wave input from unit 20.9. The Quadrature Modulated signal is processed by an optional "Roofing Filter" to remove higher order spurious components and is fed to amplifier 20.12 and to antenna 20.13 or output port 20.14. An optional Pilot Tone or Multiple Pilots are added to the RF signal by Pilot Generator/adder 20.11. Combining adding of pilot signals is achieved by hardware combiners or by adding Unmodulated signals over the air through a separate antenna.

Figure 21:
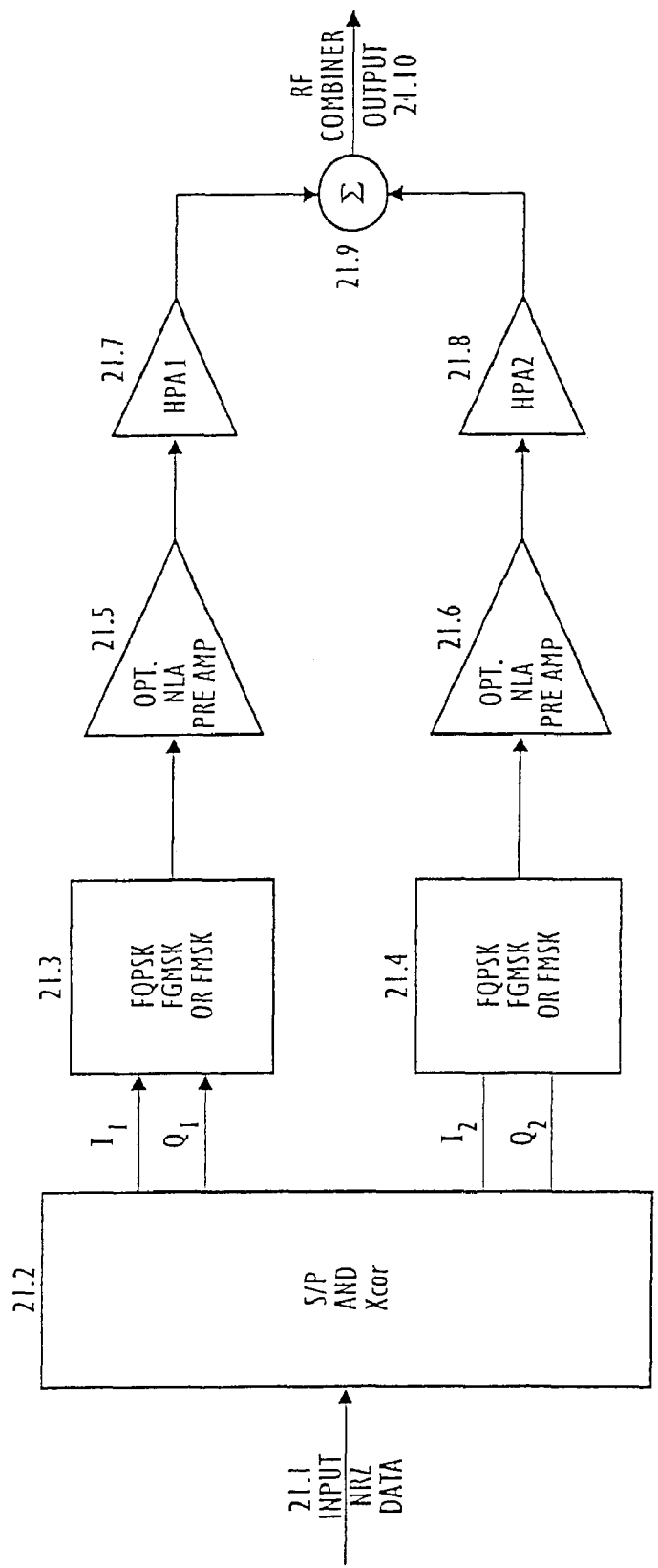
FIG. 21 is an alternate implementation diagram of multi-state FQPSK, FGMSK and FQAM transmitters. In this embodiment two or more RF amplifiers operated in NLA saturated and/or in partly linearized (LIN) mode of operation are used.

A 16 state FQAM embodiment is illustrated in the implementation architecture and block diagram of FIG. 21. This architecture can be extended and/or modified to 64 state or to other larger or smaller number of signaling states. In simple terms NLA Quadrature Modulated systems are generated by FQPSK or FGMSK or FMSK type of 4 state QM embodiments (for short the generic term "FQPSK" is also used) as described in earlier sections of this invention. If two NLA four state RF signals are combined than a 16 state NLA signal is obtained. If three NLA four state RF signals are combined than 64 state NLA signal is obtained. If four NLA four state RF signals are combined than a 256 state NLA signal is obtained and the number of signal states can be further increased by the aforementioned extension of the multiple signal combining process. The term "combining" or "Combiner" or RF signal addition in FIG. 21 is accomplished by an RF hardware combiner. Off the shelf, readily available components, such as Hybrid Microwave Combiners, are suitable for hardware RF combining. On lead 21.1 in FIG. 21 an input NRZ data signal is provided to the input ports of the Serial/Parallel (S/P) Converter 21.2. Four parallel data signals, designated as I1, Q1 and I2, Q2 are provided to FQPSK (or FGMSK or FMSK) modulators 21.3 and 21.4. One of the embodiments and/or implementations of FQPSK previously disclosed in the detailed description of this invention implements 21.3 and 21.4. The FQPSK signals are provided to Optional (Opt) preamplifiers, which operate in Linearized (LIN) or NLA mode. The High Power Amplifiers (HPA) 21.7 and 21.8 provide the RF amplified modulated signals to RF Combiner 21.9, which in turn provides the NLA combined 16-state signal to the output port 21.10.

In Seo/Feher [9] and [P4] and [6; 8] prior art references, implementation architectures of NLA systems operated in 16-QAM, 64-QAM, 9-QPRS, 81-QPRS and other quadrature modulated systems have been described and/or referenced. The aforementioned prior art does not include NLA cross-correlated, filtered and bit rate agile NLA systems for QAM disclosed in this invention, and in particular related to the discussion of FIG. 21 and FIG. 22. Based on these Feher et al. references, one of the embodiments, is related to the architectures of FIG. 21. To obtain a 16-state QAM with cross-correlated FQPSK signals that are NLA through HPA1 and HPA2, the RF amplifiers and RF combiner are adjusted to have an RF combined output fed to RF combiner, unit 21.9, which provides the RF combined output 21.10. The RF combined output power generated by unit 21.7—HPA1 is 6 dB higher than the RF power provided to output 21.10 by HPA2 designated as unit 21.8.

Figure 22:
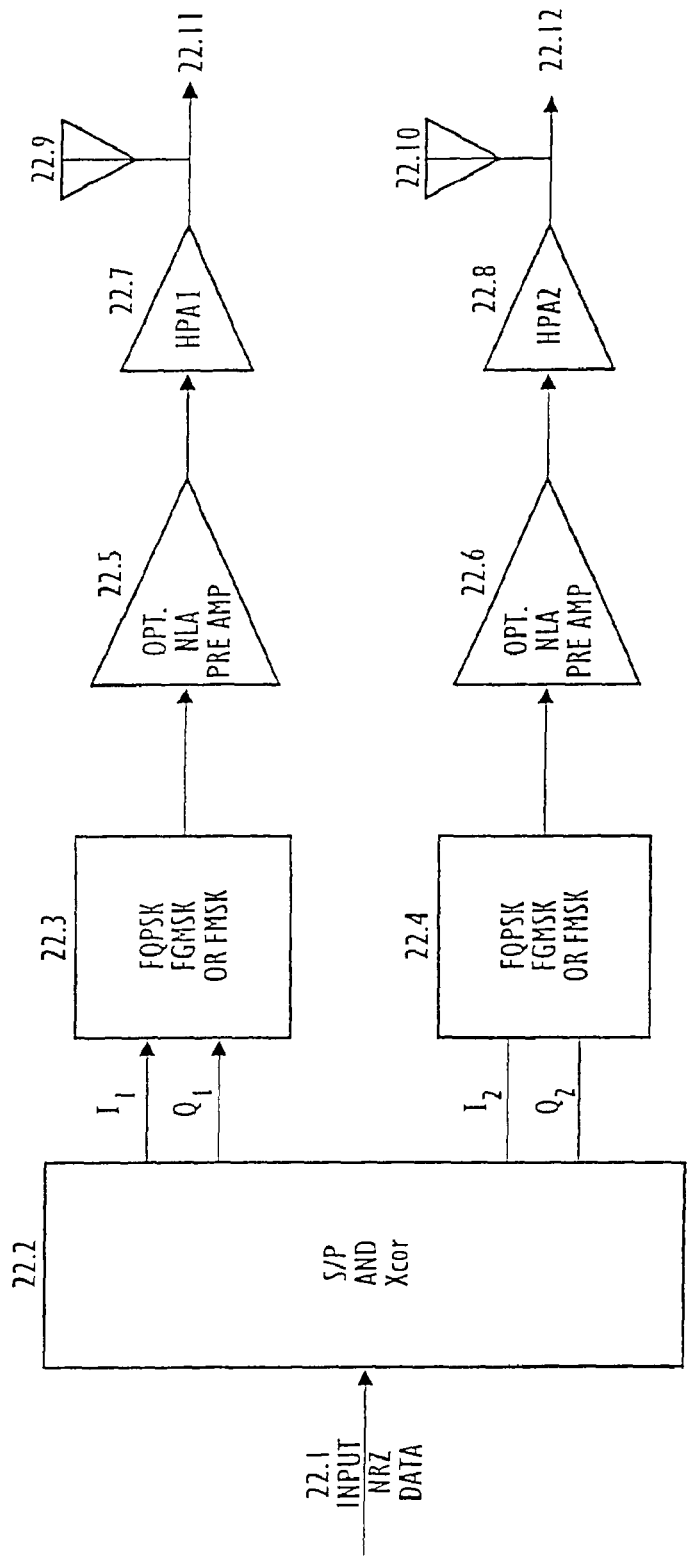
FIG. 22 is an "Over the Air Combined" implementation architecture of FQAM signal generation having two or more quadrature FQPSK and/or FGMSK modulators, two or more RF amplifiers and two or more transmit antennas.

FIG. 22 is the implementation architecture of "Over the Air Combined" FQAM signal generation by implementing 2 or more FQPSK and/or FGMSK type of signals. In FIG. 22 instead of the use of a hardware embodied RF Combiner to combine the HPA1 and HPA2 signals, the output signals of HPA1 and HPA2 are fed to two separate antennas and transmitted as wireless signals "over the air." In this architecture RF Combining is achieved "Over the Air" that is the RF signals are transmitted over a wireless medium and combined in the receiver antenna.

The baseband processor, quadrature modulator and signal amplifiers architecture of the NLA signals, "Over-the-Air Combined," is closely related to that of FIG. 21 which uses the hardware RF combiner. The input NRZ data on lead 22.1 is provided to a Serial/Parallel (SIP) unit 22.2 which provides 4 parallel signals two FQPSK quadrature modulators, units 22.3 and 22.4. The quadrature modulated signals are provided to amplifiers, and in particular, to optional NLA 22.5 and to High Power Amplifier (HPA) 22.7 in the upper part of the figure. HPA-1, unit 22.7 provides the RF modulated signal to antenna 22.9 or to an output port 22.11. In the lower branch the FQPSK modulator, unit 22.4, provides the quadrature modulated signal to optional NLA 22.6 and to HPA-2, unit 22.8. The amplified signal of 22.8 is provided to antenna 22.10 and/or to output port 22.12.

To obtain a 16-state QAM with cross-correlated FQPSK signals that are NLA through HPA-1 and HPA-2, the RF amplifiers and RF combiner are adjusted to have an RF combined output fed to antenna 22.9 and/or output port 22.11, 6 dB higher in power than the RF power provided to antenna 22.10 and/or output port 22.12.

Figure 23:
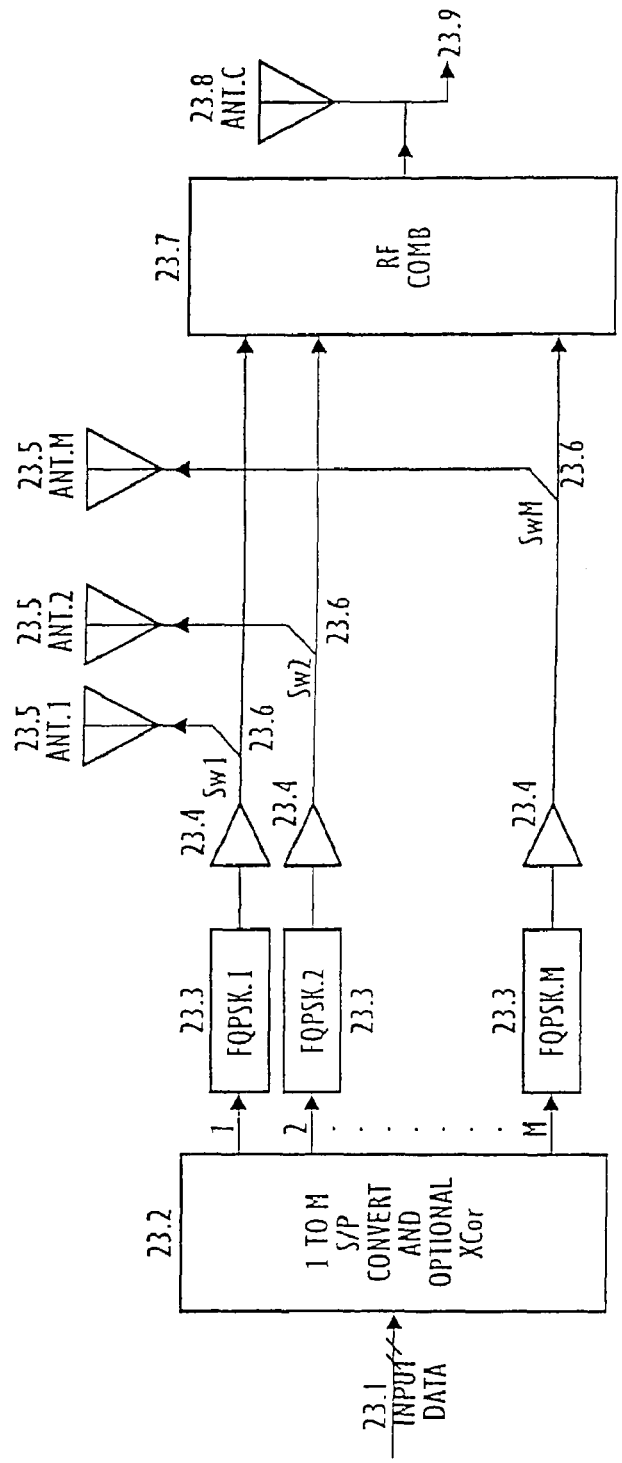
FIG. 23 shows the embodiment of an Orthogonal Frequency Division Multiplexed (OFDM) embodiment with FDM signal combining of a number of FQPSK signals. In one of the embodiments of this invention RF Combining is implemented by hardware RF components while in an alternative implementation the RF combining is implemented "over the air".

FIG. 23 shows the embodiment of an Orthogonal Frequency Division Multiplex (OFDM) type of embodiment with FDM signal combining of a number of FQPSK type of Lin or NLA signals. In one of the embodiments of this invention RF Combining is implemented by hardware RF components while in an alternative implementation the RF combining is implemented with "Over the Air Combined" signals. If multiple antennas are used, then this architecture is also known as an "Antenna Array" (AA) architecture. Lead 23.1 containing the Input Data (ID) is provided to a Serial-to-Parallel (SIP) converter, unit 23.2, having M set of outputs where one output set constitutes a separate I and Q signal or a serial data stream. The S/P converter 23.2 may contain an optional cross correlator (Xcor). As the input signal is S/P converted, the data rates on the 1, 2, ..., M input leads to the bank of FQPSK modulators 23.3 are at an M times reduced data rate compared to the input data rate. As an illustrative example of this architecture, if the input data rate is Fb=10 Mb/s and there are 100 FQPSK modulators (M=100), then the bit rate of individual FQPSK modulators is 10 Mb/s: 100=100 kb/s. The aggregate transmission rate of such a system is not changed. The aforementioned parallel data are provided to M modulators designated as FQPSK.1, FQPSK.2, ..., FQPSK.M, collectively referred to as unit 23.3. These modulated signals are provided to a set of RF amplifiers, 23.4 and optional RF Switches units designated as 23.6. The M amplified signals are provided in one of the embodiments through RF combiner 23.7 to a single antenna "Ant.C" unit 23.8 or port 23.9. In an alternate use the M modulated and amplified signals at the outputs of RF amplifiers 23.4 are provided to the antenna array 23.5 designated as Ant.1, Ant.2 ... to Ant.M. If the Antenna Array architecture is used, then the M signals are "Over the Air Combined" signals. If a hardware RF combiner 23.7 is used with a single antenna 23.8 or output port, then the architecture represents a hardware combined embodiment. An advantage of the "Over the Air Combined" architecture is that all RF amplifiers within the set 23.4 may operate in fully saturated NLA power efficient mode.

Figure 24:
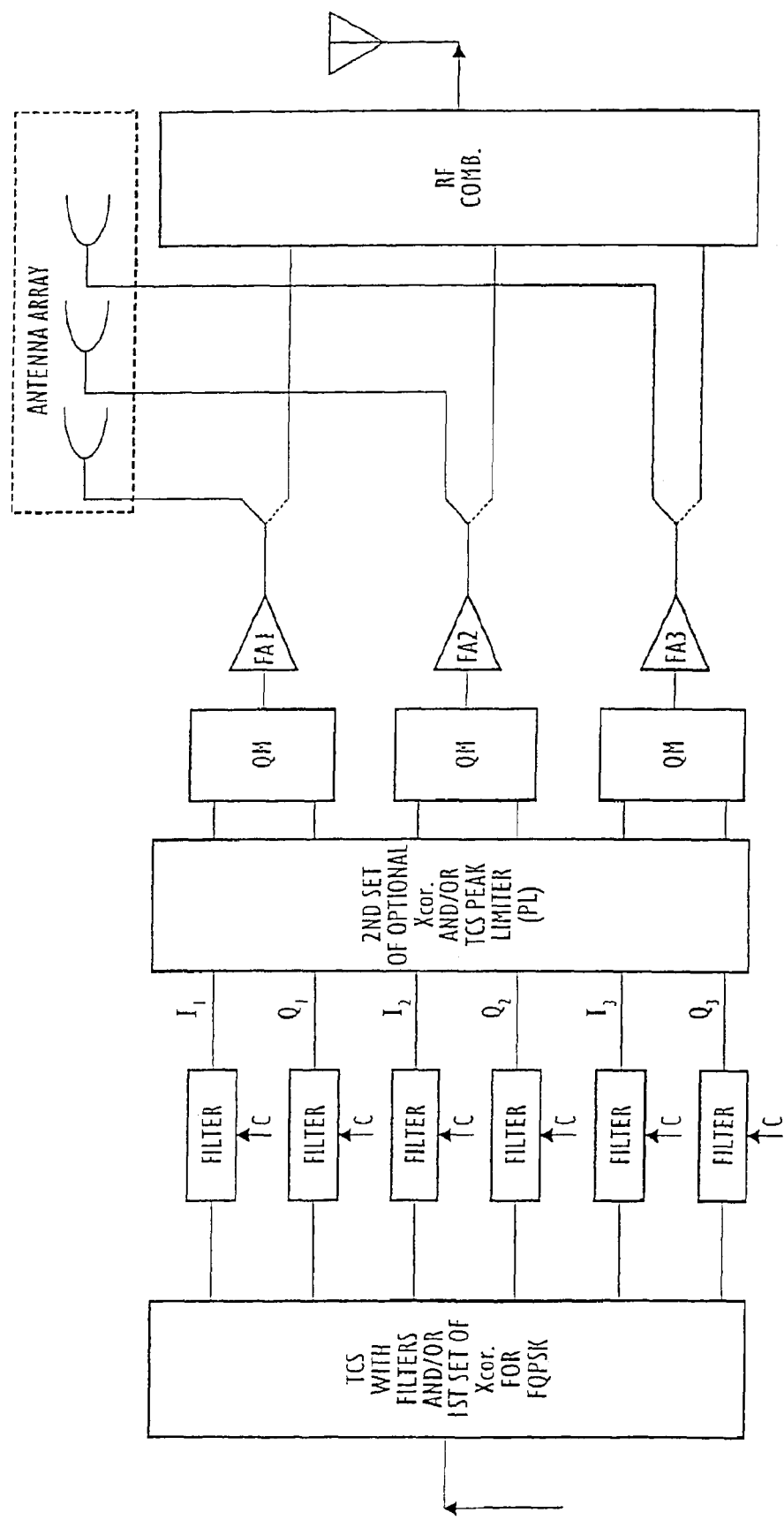
FIG. 24 shows a transmit Antenna Array and/or RF Combining implementation of multiple modulated signals. This figure illustrates multiple TCS response and/or cascaded TCS response and LR filtered cross-correlated baseband signal processors connected to an antenna array and/or RF combiner.

FIG. 24 is an alternate Antenna Array and RF Combining implementation architecture of multiple FQPSK type of signals. This figure illustrates multiple TCS and/or filtered BB processors connected to an antenna array and/or RF combiner. Input lead 24.1 contains an input signal or a multitude of signals, which could comprise analog signals, digital binary or digital multilevel signals, or other signals, for short "Input Signal." Unit 24.2 receives the input signal and processes it with a TCS containing optional LR filters and/or a $1^{st}$ set of cross correlators (Xcor) for FQPSK signals. A Bit Rate Agile clocked bank of filters 24.3 receives the signals of 24.2, processes them and provides to unit 24.4 which is an optional $2^{nd}$ set of Xcor and/or TCS with LR response filters and/or Peak Limiter (PL) devices. The signals from 24.4 are provided to Quadrature Modulators 24.5 and to a bank of amplifiers 24.6 in the figure illustrated as FA1 to FA3. The RF amplified signals are provided to antenna array 24.8 or to RF combiner 24.9 through the set of RF switches 24.7. The RF combined output is provided to antenna 24.10 or alternately output port 24.11.

Figure 25:
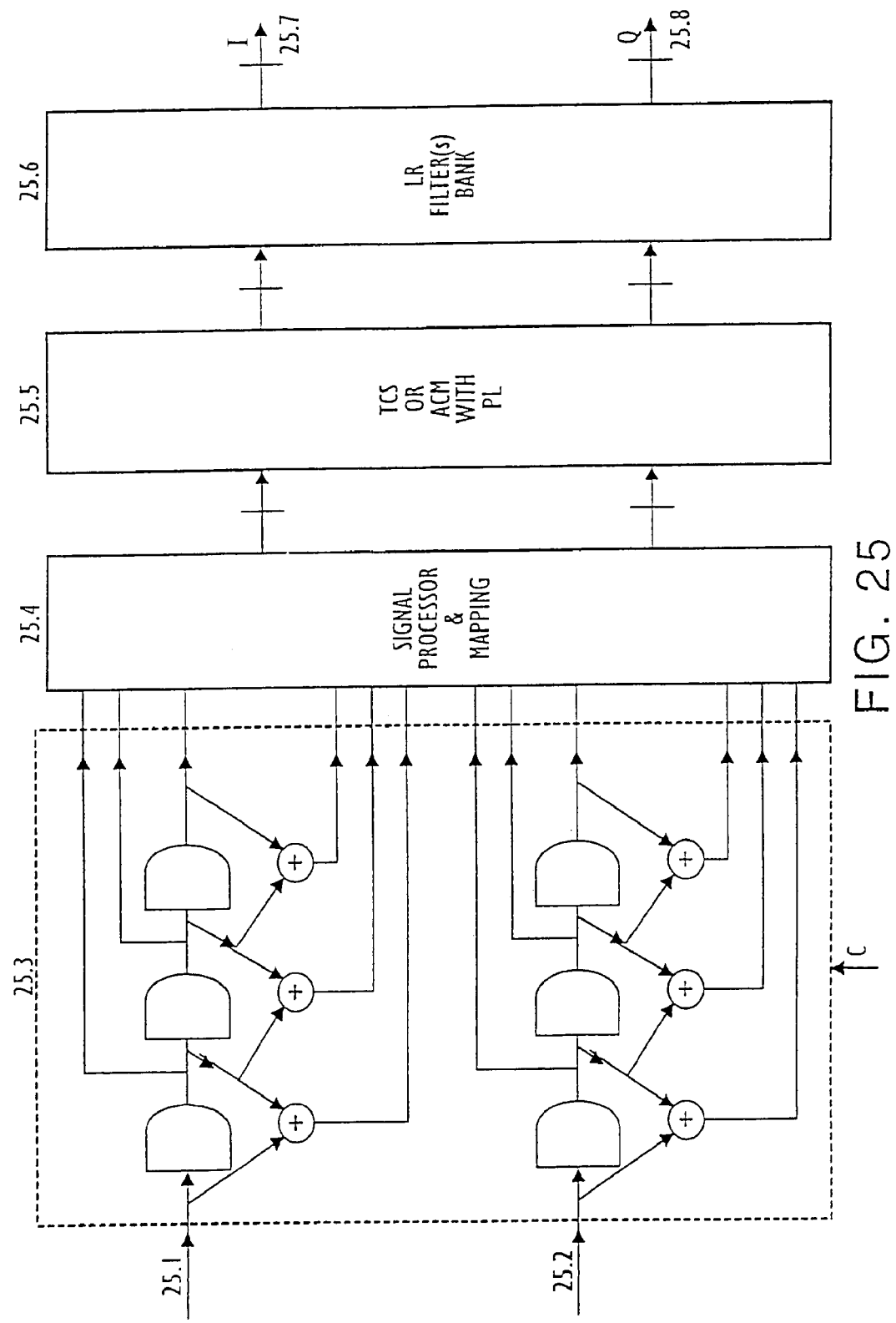
FIG. 25 shows an ACM and PL architecture and embodiment for trellis coded filtered cross-correlated I and Q baseband signal generation, containing TCS response and cascaded LR filters, for FQPSK, FGMSK as well as FQAM signal generation.

In FIG. 25 an alternate implementation of encoding and signal mapping of FQPSK, FQAM and FGMSK signals is shown. In the embodiment of FIG. 25 a trellis coded implementation with an appropriate signal mapping for trellis coded generic FQPSK without the need for redundancy is shown. In addition to trellis coding other coding algorithms are suitable for the shown implementation architecture. The aforementioned other encoders include non-redundant Differential Encoding (DE), Gray encoding, encoding/conversion of NRZ signals into RZ or FRZ signals or Manchester or other sets of signals. Encoding for error correction and detection may require the insertion of redundant bits and Forward Error Correction (FEC) encoders such as Block Encoders including Reed-Solomon, BCH, convolutional, CRC and other encoders are among the illustrative embodiments of encoders suitable for FIG. 25. The specific trellis encoder schematic diagram and signal mapping part of FIG. 25 is based on Simon/Yan's published reference [22], which includes logic/encoding 25.3 and signal mapping 25.4. The aforementioned reference does not disclose embodiments for TCS and LR filtered changeable amount of cross correlated and of filtered Bit Rate Agile (BRA) and/or Peak Limited (PL) implementations and of Agile Cascaded Mis-Matched (ACM) filtered systems having single or multiple I and Q readout tables with compressed memory elements.

In FIG. 25 trellis coded TCS and LR filtered FQPSK signals having BRA applications with or without Cross-Correlation and with and without Peak Limiting (PL) circuits in the I and Q channels are shown. The digital processing parts of the trellis or other encoder precede the additional TCS and LR and other processors in the implementation embodiment of FIG. 25. In alternate embodiments the digital encoder with and without trellis coding is integrated in one block and one function with parts or all of the TCS and LR blocks or the order of processing is changed.

Illustrative Performance of Exemplary System

The performance of illustrative and some of the "best-illustrative" embodied FQPSK and related BRA systems of this invention is highlighted. This invention includes numerous embodiments and has a large class of subsystems and implementation details as well as designations. For this reason the term "best-illustrative" is used herein. For some users and designers "best" means the narrowest possible spectrum at a Power Spectral Density (PSD) of about −20 dB to meet certain FCC mandated requirements, while for other users the "best" PSD is defined at −70 dB for others "best" refers to best Bit Error Rate (BER) performance in an Additive Wide Gaussian Noise (AWGN) operated environment, while for some others the "best" or "optimum" BER=f(Eb/No) performance is most desired. Other categories of the term "best" could mean fastest synchronization or re-synchronization of a receiver/demodulator or "best" BER performance or smallest number of outages in an RF delay spread-frequency selective faded environment with the "best," that is, fastest and highest performance adaptively equalized demodulators. A large category of designers and users of this invention might define "best" as the lowest cost commercially available equipment from numerous sources having the highest spectral efficiency simultaneously with the smallest size for a certain RF power and the "best," i.e., maximal Bit Rate Agile (BRA) flexibility and/or interoperability and compatibility with previous generations and implementations of FQPSK and/or of other "legacy" systems. For the aforementioned reasons the term "best illustrative" is used in the performance attained with some of the aforementioned "best" implementations.

As an illustration of one of the "best illustrative" NLA spectra, the Power Spectral Density (PSD) of NLA wireless/telemetry system is illustrated in FIG. 26. The multiple data links in these telemetry systems are operated at specific bit rates of 13 Mb/s rate per link. The spectra shown in FIG. 26 are typical for spectral usage in the U.S. for the U.S. Government-authorized band of 2200 MHz to 2290 MHz for Government applications. In FIG. 26 one or more of the modulated and received signals is shown to be in the 18 dB to 20 dB lower than that of adjacent signals. In "real-life" systems it is often the case that the desired signal power is about 20 dB lower in power than that of the adjacent signals. With telemetry standardized filtered PCM/FM systems, at the aforementioned 13 Mb/s rate, 3 data links can be used simultaneously. During the 1990s, filtered PCM/FM systems have been extensively used. With emerging FQPSK systems and in particular Draft Standardized FQPSK-B systems the number 13 Mb/s rate links is doubled to 6, while with 16-state FQAM, also designated as FQPSK.2.4 the number of 13 Mb/s links is quadrupled (over that of standardized PCM/FM) to 12 data links. Thus the spectral efficiency of FQPSK is double that of standardized filtered PCM/FM and the spectral efficiency of FQAM with 16 states and operated also in an NLA mode is quadruple that of the standardized filtered PCM/FM systems.

Figure 27A:
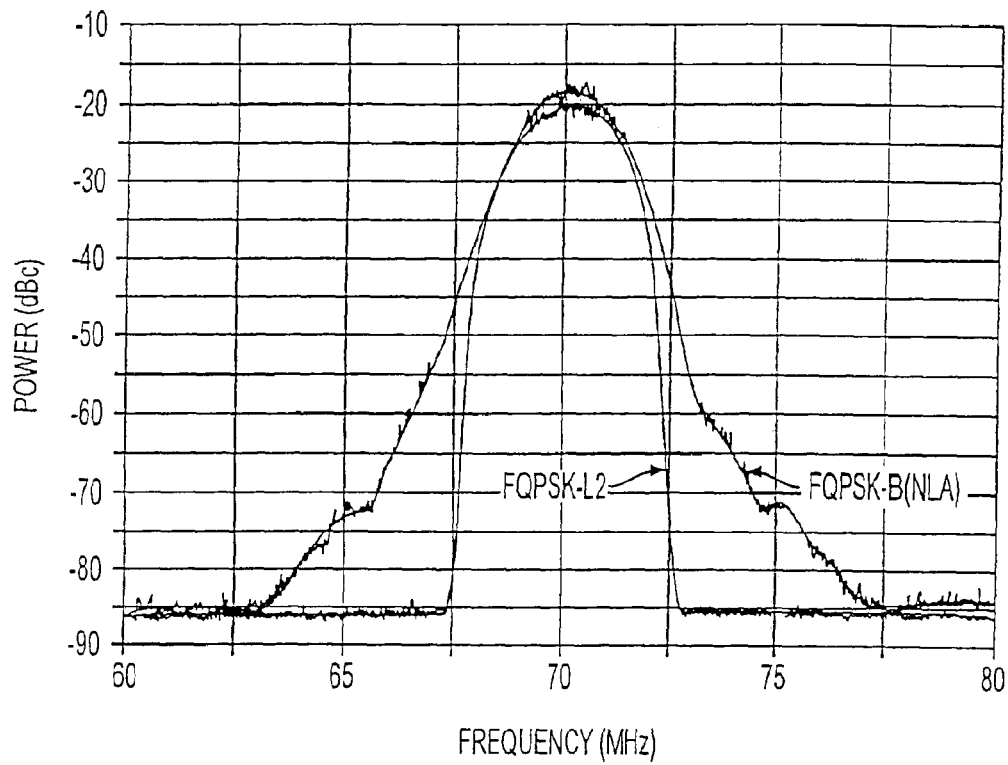
FIG. 27 The PSD and Integrated Adjacent Channel Interference (ACI) of hardware measured prototype FQPSK-B in a NLA transmitter and of a BRA linearized transmit FQPSK is illustrated in the upper figure. In the lower part of this figure the Integrated ACI of FQPSK systems with that of GMSK (BTb=0.25) systems is compared. For NLA transmitters, the results show a very significant (approximately 2 to 1) RF spectral efficiency advantage of FQPSK over that of GMSK systems. The aforementioned FQPSK 2 to 1 spectral advantage over that of conventional GMSK is measured for a typical −60 dB specification of the ACI.
Figure 27B:
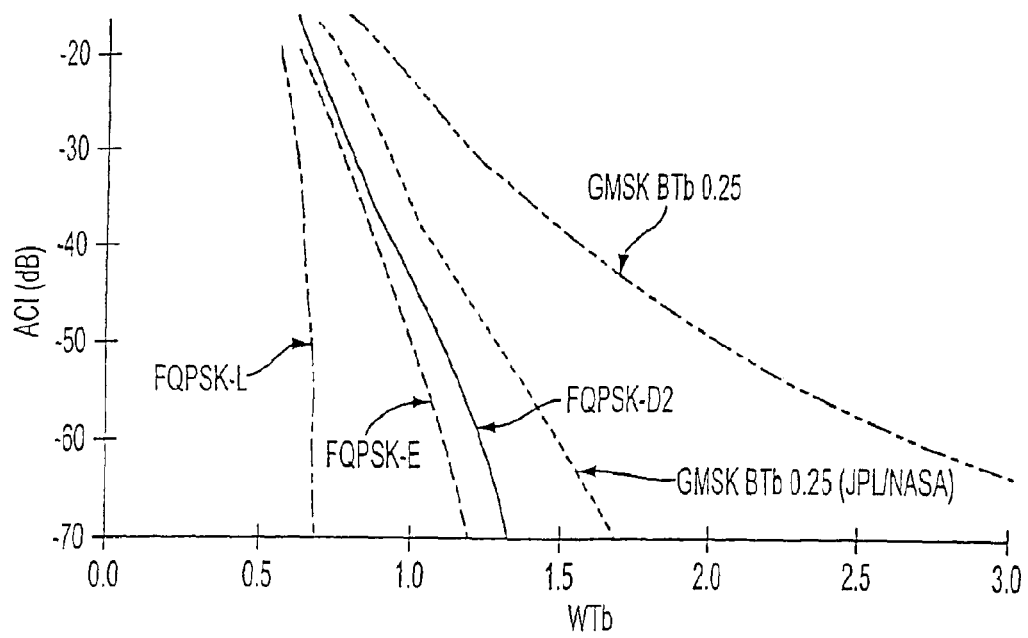

From FIG. 26 illustrated spectra it is noted that the Integrated Power from the adjacent channels falling into the desired channel may have a significant impact on the performance of the desired channel. In the referenced publications and patents the importance of Integrated Adjacent Channel Interference (ACI) is highlighted and described. For this reason the Power Spectral Density (PSD) and the ACI of Linearly (Lin) and of NLA transmitted FQPSK and GMSK signals is shown in FIG. 27. The PSD and Integrated ACI of hardware measured prototype FQPSK-B in a NLA transmitter and of a BRA linearized (Lin) transmit FQPSK is illustrated in the upper part of FIG. 27. In the lower part of FIG. 27 the Integrated Adjacent Channel Interference of FQPSK systems with that of GMSK systems is compared. In this figure "W" denotes the frequency spacing between Adjacent Channels. In case of GMSK which has been implemented with BRA embodiment described in this invention and designated as FGMSK having a Gaussian filter and bit duration (Tb) product of 0.25 has been used in the computed ACI result shown in FIG. 27. The computed ACI of a BTb=0.25 filtered system with considerably steeper filters than that of conventional Gaussian receive filters was simulated by JPL/NASA. The ACI curves for FQPSK-B and FQPSK-D1 as well as FQPSK-Lin are also included. Note from the results the significant (approximately 2 to 1 at −60 dB) spectral ACI advantages of FQPSK over that of GMSK systems.

Multi-state FQAM systems such as 16-state FQAM designated also as FQAM-16 and FQPSK.2.4 (the first number in this latter abbreviation indicates $2^{nd}$ generation FQPSK while the 2nd having 4 signaling states per I and per Q channel). In NLA systems have approximately double the spectral efficiency of the already-spectrally-efficient FQPSK systems including BRA systems operated in an FQPSK-B mode disclosed in this invention. The abbreviation "FQPSK-B" is a designation for cross-correlated FQPSK systems having an embodiment in which the TCS cross correlators are cascaded with LR filters operated in a BRA mode. The substantial spectral saving attained by 16-state FQPSK systems over alternative conventional 16-QAM pre-RF amplification filtered systems is illustrated by the computer-generated results shown in FIG. 28.

Figure 28:
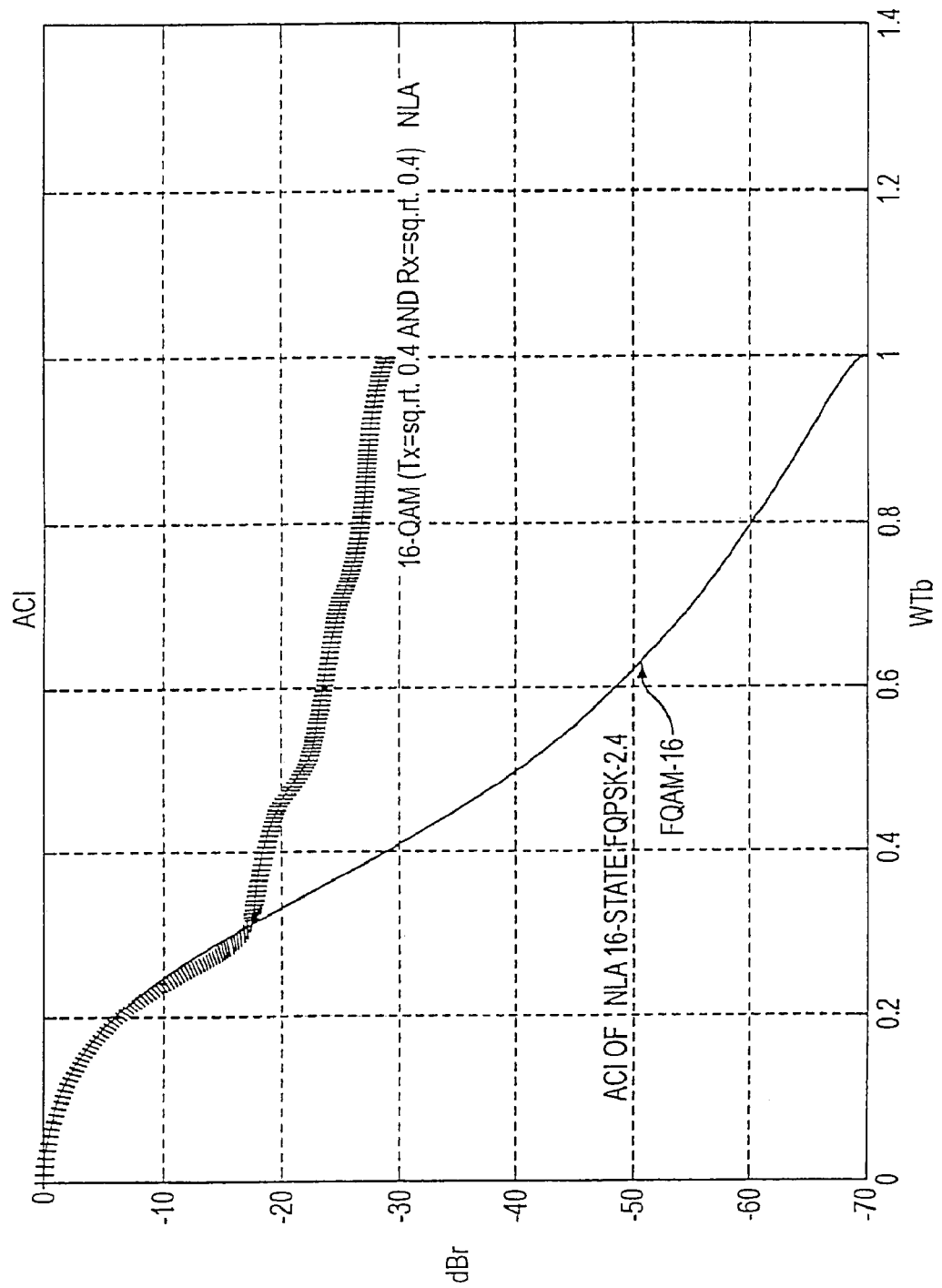
FIG. 28 Spectral results of 16 state NLA systems are illustrated. The ACI results FQAM, obtained after fully saturated NLA, are compared with that of NLA conventional pre-modulation filtered 16-state QAM systems. The spectral efficiency advantage of the NLA illustrated FQAM is more than 200% over that of NLA prior QAM.

In FIG. 28 the ACI results of illustrative FQPSK.2.4 (also designated as FQAM-16) state systems, obtained after fully saturated NLA, are compared with that of NLA conventional pre-modulation filtered 16-state QAM systems. The spectral efficiency advantage of the illustrated FQAM is more than 200% over that of prior art QAM at −30 dB and FQAM has an even more significant spectrum advantage in terms of ACI at the critical −40 dB to −60 dB range. High performance systems require a robust BER performance in Additive White Gaussian Noise (AWGN) and also other interfering and noise environments. A frequently-used performance indication is the BER performance as a function of the available Energy of a Bit (Eb) to Noise Density (No) ratio. For RF power efficient as well as spectrally efficient systems having a robust BER, the NLA system performance in terms of BER=f(Eb/No) is specified for numerous system applications. In particular, in FIG. 29 the performance of FQPSK is highlighted.

Figure 29:
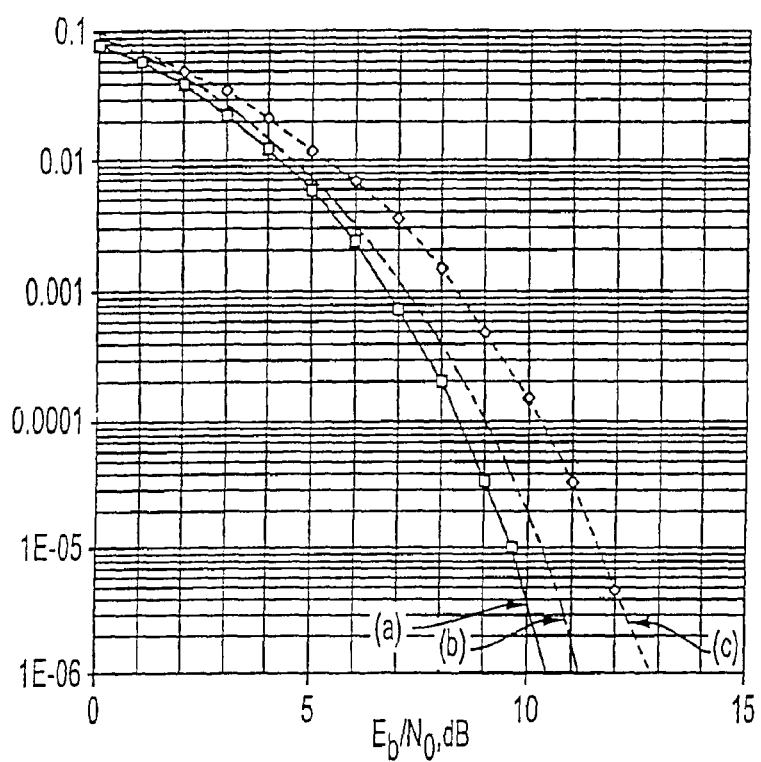
FIG. 29 shows BER performance curves, in terms of the customary BER=f(Eb/No) performance curves, of FQPSK Transceivers. Hardware measurements and/or computer design/software generated data and theoretical study results show that NLA practical RF hardware FQPSK Transceivers, with intentionally and substantially Mis-Matched (MM) filters are within about 0.5 dB to 1 dB of the ideal theoretical LIN amplified QPSK systems.

FIG. 29 The BER performance, in terms of BER=f(Eb/No), of prototype measurements and Computer design/software generated data of FQPSK systems illustrated that NLA FQPSK is within about 0.5 dB of the ideal theoretical LIN amplified QPSK systems. Simple bit by bit detection as well as trellis decoding without redundancy has been used. In FIG. 29 curve (a) represents an ideal theoretical linearly (LIN) amplified system, while curve (b) represents a BER optimized NLA-FQPSK, and curve (c) represents a BRA and MM hardware-prototype measured FQPSK-B system performance, prior to optimization.

Detailed Description of Exemplary Embodiments of Receivers and of Demodulators

Receivers and Demodulators are described in this section. Signal reception, adaptive equalization, demodulation, fast and robust synchronization, bit recovery, Non Redundant Error Detection (NED), online in service monitoring, Non Redundant Error Control (NEC) and new architectures and embodiments for Bit Rate Agile (BRA) and NLA cross-correlated FQPSK, FQAM and related systems are disclosed in this part of the invention.

Figure 30:
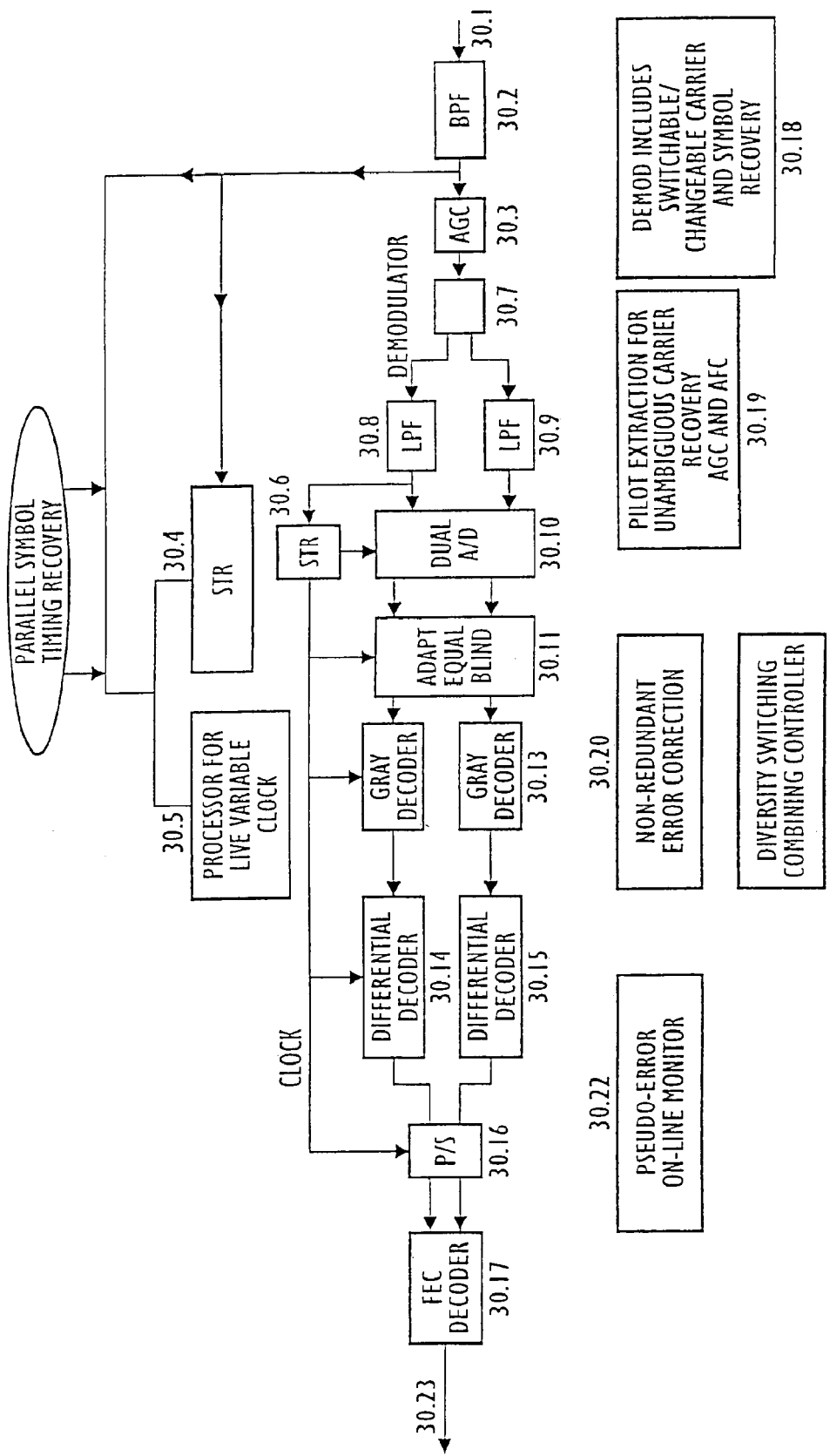
FIG. 30 shows a demodulation architecture for FQPSK, FGMSK and FQAM and for other signals.

In FIG. 30 a generic receiver and demodulator is shown. In this FIG. 30 demodulation of FQPSK type of signals, by using quadrature demodulation structures such as QPSK, QAM and OQPSK demodulation, enhanced by the architectures of the embodiment, illustrated in this figure is accomplished. Fast signal acquisition is attained and numerous other performance enhancements are achieved by the disclosed generic embodiment of this demodulator. Input port and lead 30.1 obtains a modulated signal from a receive input port. The optional BPF unit 30.2 is provided in some of the embodiments in which excessive strength out-of-band/or adjacent channel signals degrade the performance of the subsequent circuits if this "protection" or "roofing" BPF is not present. Automatic Gain Control (AGC) circuit 30.3 operates in a linear or in a non-linear (NL) mode. For some applications an advantage of FQPSK and FQAM type of signals is that they are suitable for nonlinear AGC operation. From the prior art it is well known that nonlinearly operated AGC circuits such as "hard-limiters" and "soft-limiters" have faster AGC operation than their linear counterparts and in certain environments nonlinear AGCs outperform linear AGCs and in particular regarding "weak signal suppression" and also lead to reduction of Co-Channel Interference and of Inter-Symbol Interference (ISI) caused by certain RF delay spread-frequency selective faded environments. The optional AGC provides the quadrature demodulator 30.7 and follow-up signal processors including LPFs 30, Analog/Digital (A/D) 30.10, Symbol Timing Recovery (STR) 30.6, Adaptive Equalizer (AE) which could be a blind equalizer 30.11 and digital logic circuits decoders 30.12 to 30.17 the signals for demodulation and decoding. Additional signal processors which enhance the performance of the receiver/demodulator of this invention include one of the following: switchable changeable Carrier and Symbol Recovery unit 30.18, Pilot Extraction for unambiguous carrier recovery, fast AGC, and Automatic Frequency Control 30.19. Non-Redundant Error Detection (NRED) unit 30.20, Diversity Switching Combining Controller 30.21 and Pseudo-Error On-Line Monitor 30.22 units are also included.

Figure 31:
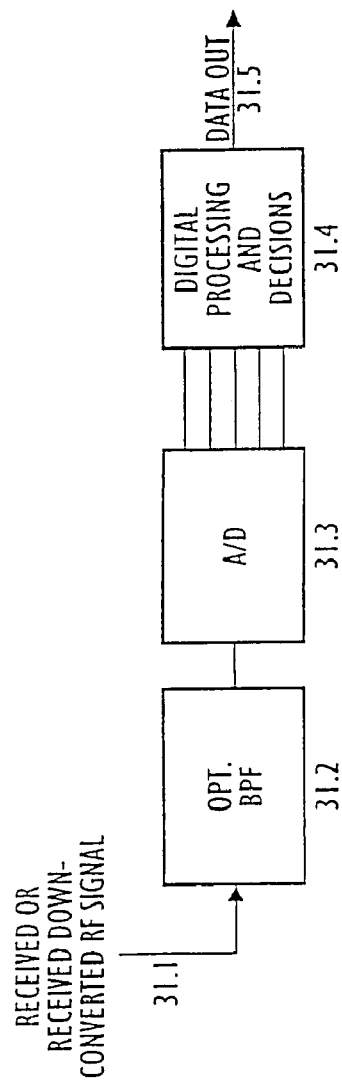
FIG. 31 shows an alternate A/D converter based demodulator architecture. This implementation/embodiment is suitable for "software radio" demodulation and/or for firmware or hardware, or combined hybrid implementations of this invention.

FIG. 31 is a demodulator architecture also known as a "Block Demodulator" and/or digital demodulator or software demodulator. This implementation/embodiment is used for software or firmware or hardware, or combined hybrid implementations of this invention. On receive port/lead 31.1 the received RF signal or the received RF signal down-converted to a convenient IF frequency or to the baseband frequency range is shown. Unit 31.2 is an optional "roofing" BPF or other filter to protect the front end of the A/D 30.3 unit from out-of-band signal overload. The A/D provides serial or parallel signals for further digital processing, decision making and decoding in unit 31.4. The data is provided to output port 31.5.

Figure 32:
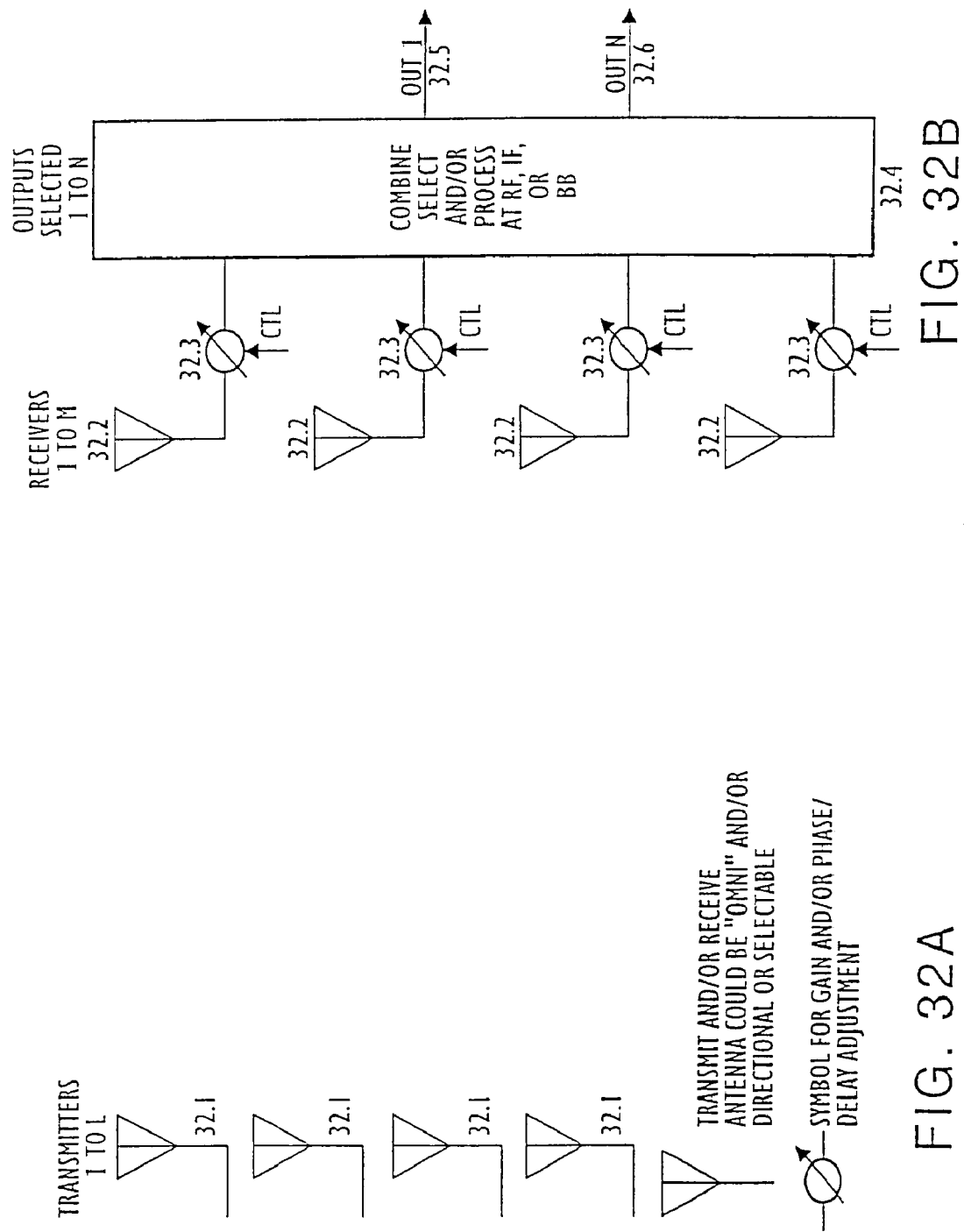
FIG. 32 shows transmit Antenna Arrays (AA) and receive Adaptive Antenna Arrays (AAA) in this multiple transmit and receive omni-directional and/or sectorized or high gain directional antenna-embodiment of this invention. This architecture has the potential to increases the NLA spectral efficiency of FQPSK, FGMSK and FQAM systems to more than 30 b/s/Hz.

FIG. 32 shows Antenna Arrays (AA) in this multiple transmit and receive with omni and/or directional antenna embodiment. This architecture with Adaptive Antenna Arrays (AAA) has the potential to increases the NLA spectral efficiency of FQPSK, FQAM and FGMSK systems to more than 30 b/s/Hz by processing the transmit and/or receive antenna signals in a directional mode. An interesting prior art reference is Winters [23], which contains several system applications of system applications of conventional non-patented modulated systems. The potential advantage of the embodiment of FIG. 32 for FQAM and FGMSK systems as due to the fact that the FQPSK and FQAM type of systems are suitable for NLA power and RF spectral efficient robust performance operation with single, dual and multiple antennas. Larger number of AA further increases the spectral efficiency and thus capacity of the systems of this invention in specific geographic areas covered by the AAs and AAAs.

Figure 33:
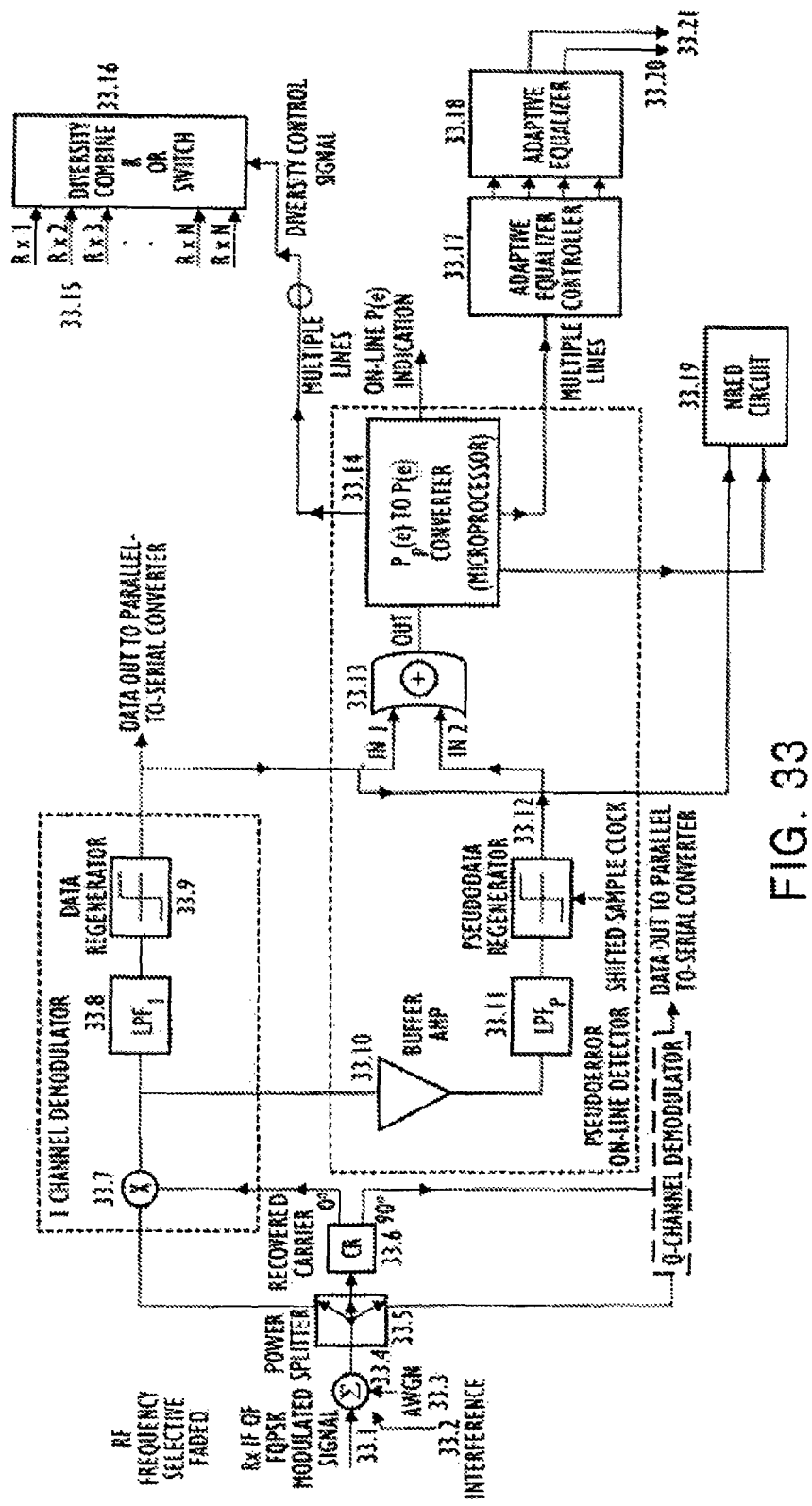
FIG. 33 shows a Pseudo-Error (PE)-Non-Redundant Error Detection (NRED) circuit embodiment for on-line or in-service monitor, for PE based adaptive equalization control and for diversity control unit implementations.

FIG. 33 shows a Pseudo-Error (PE) on-line, or in-service monitor generic block diagram with on-line Probability of Error (Pe) monitor, diversity control, adaptive equalization control and Non-Redundant Error Control circuit also designated as Feher's Non-Redundant Error Control (FN) detection and correction. Non-intrusive on-line, also known as in-service bit error or Bit Error Rate (BER) or Probability of Error (Pe) monitoring of received signals has numerous benefits for the user of digital communication systems. Prior art references including Feher's [1,2,3] and the references contained therein describe the operational principles and some of the embodiments of the so-called "Pseudo-Error" on-line bit error detectors." While pseudo-error detection by itself is known from the prior art, pseudo-error monitoring of cross-correlated and filtered BRA systems combined with pseudo-error monitor generated control signal generation for adaptive equalization and/or diversity control techniques and embodiments are part of this new invention.

Pseudo-Error (PE) operation, adaptive equalization and diversity control signal generation by PE generated signals is described in relation to FIG. 33. On lead 33.1 the received RF signal is present. This signal could be converted to a convenient IF and/or near the baseband frequency range and could be RF selective faded and/or corrupted by interference. In FIG. 33 an FQPSK received modulated signal is illustrated; other types of modulated signals could be also processed with the PE based structures of FIG. 33. In addition to signal distortion, exhibited in terms of ISI, caused by RF selective, time-dispersive propagation channels Interference 33.2 and Additive White Gaussian Noise (AWGN) 33.3 is assumed to be corrupting this system by having interference and AWGN added to the desired signal path in 33.4. Following the selective faded signal path and interference and noise, the power splitter 33.5 provides the signal to I Channel Demodulator 33.7, 33.8 and 33.9 and Q channel demodulator and to the Carrier Recovery (CR) unit 33.6. The regular demodulated and regenerated data is present as "Data out to parallel to serial converter" in the I and Q channels. The PE circuit or "Pseudo-error on-line detector" has at its input stage an input port, designated as a buffer amplifier 33.10, followed by the 33.11 LPF (Low-Pass Filter in the "pseudo" path (lower case "p" in the abbreviation) and the regenerator or threshold detector 33.12. Unit 33.13 is a clocked Exclusive-OR (ExOR) circuit which has the regular demodulated "Data out to parallel to serial converter" as one of its data inputs "In1" and has the regenerated data from the pseudo data regenerator 33.12 as its $2^{nd}$ data input "In2". The clocked ExOR circuit (the clock input is not drawn to the ExOR-to simplify the drawing) 33.13 provides binary pulses to the Pp(e) to P(e) converter

33.14. Unit 33.14 is implemented by simple logic and counter circuits and/or as part of a micro-processor and by software, hardware or firmware.

Pseudo-Error (PE) implementations and their operating principles have been described in the literature, including references [1,2,3]. Unit 33.14 provides a signal to the Non Redundant Error Control (NREC) circuit 33.19, which is used, for display of the actual estimated Pe or BER of the data stream. Implementations of PE detectors, described in the aforementioned references, or variations of PE detector implementations used in this invention serve as Adaptive Equalizer (AE) control signal generators and Control Generators for Diversity Combining and/or fast synchronization systems. In one of the structures of this invention 33.14 provides one or more signal lines to the Adaptive Equalizer Controller 33.17 and in turn to the Adaptive Equalizer (AE) 33.18. The AE provides to output ports 33.20 and 33.21 control signals.

Figure 34:
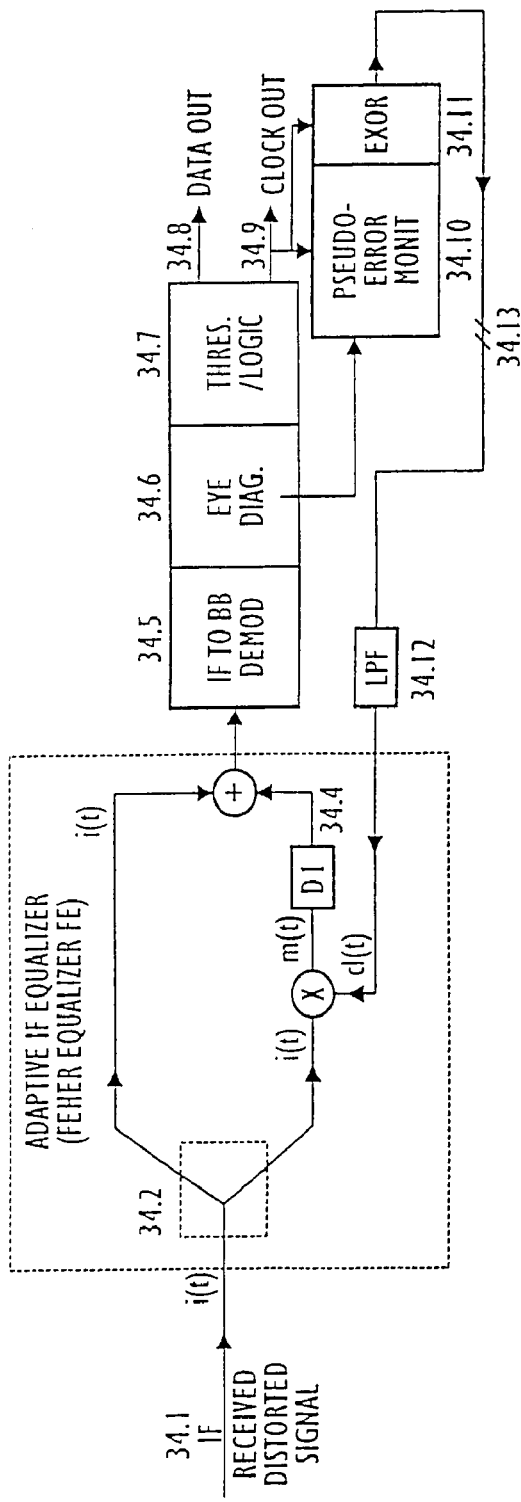
FIG. 34 shows an adaptive equalizer circuit embodiment of this invention. The adaptive equalizer, designated as Feher Equalizer (FE) generates the control signals in a PE based NRED circuit and is suitable for fast adaptive equalization.

In FIG. 34 an implementation block diagram of a Pseudo-Error (PE) controlled IF adaptive equalizer of this invention, designated as Feher Equalizer ("FE") is shown. The elements, described in conjunction with FIG. 33, described previously are used in this structure of FIG. 34. At the input lead 34.1 the received RF or IF signal is provided to splitter 34.2. The splitter output, designated as i(t) is fed to a signal combiner 34.4b. The lower branch of the splitter provides an input to signal multiplier 34.3, followed by delay element DI and the multiplied and delayed signal is fed to the second input of combiner 34.4b. The combiner output is fed to an IF to baseband quadrature demodulator unit 34.5. The multiplier unit 34.3 receives at its second input one or more control signal (s), designated as $c1(t)$ and generated by the PE monitor loop. The aforementioned multiplier 34.3 serves as a controlled signal attenuator, that is, it provides a time variable attenuation (or time variable gain) in the lower branch of the "one tap" adaptive IF equalizer comprising splitter 34.2, combiner 34.4b, multiplier (also designated as mixer) 34.3, delay element D1 34.4a and combiner unit 34.4b.

The Demodulator 34.5 of FIG. 34 has a structure such as the I and Q channel demodulators shown in FIG. 33. The demodulated "eye" diagram (for definitions and terms such as eye diagram—see one of the references listed, including [1, 2 or 3]) through interface 34.6 provides the data output via threshold regenerator and logic 34.7 to output port 34.8 and the clock to 34.9, while the signals to the PE monitor are on leads 34.10 and 34.11. Single or multiple lead signals on lead(s) 34.13 are provided to LPF 34.12 for signal shaping and/or processing and for providing the aforementioned $c1(t)$ control signal to one of the inputs of the multiplier 34.3 of the adaptive equalization system. The operation of the adaptive Feher Equalizer (FE) shown in FIG. 34 operates in a baseband to IF feedback loop in which the control signal is generated by a PE detector. The PE signal is a binary fully regenerated signal thus it is not the same type of signal as used to control the coefficients of conventional adaptive taps of adaptive equalizers.

Figure 35:
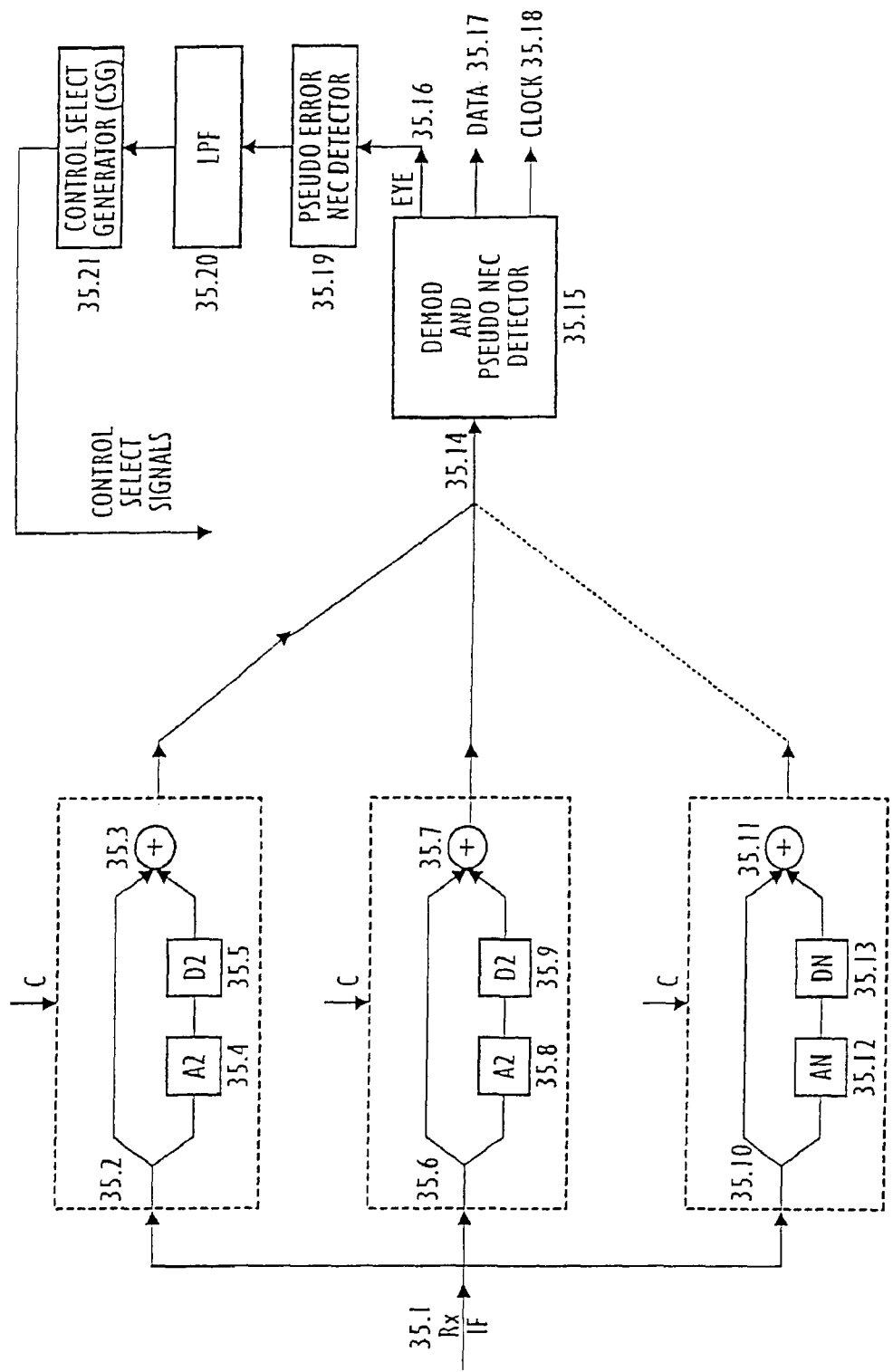
FIG. 35 is a switchable delay based embodiment of a combined adaptive equalizer/adaptively selectable switched receiver designated as Feher Rake "FR." A PE based NRED or other NRED circuits are used for generating the control and switch selection signals.

FIG. 35 is a diagram of a multiple delay switchable Adaptive Equalizer (AE) designated as Feher Rake "FR". A Non-Redundant Error Control (NEC) detector, such as a Pseudo-Error (PE) circuit based NEC is used to generate one or multiple control signals, designated as "Control Select Signals". Received signal on lead 35.1 is provided to multiple splitter ports 35.2, 35.6 and 35.10. The splitters provide signals to variable gain amplifiers A1 to An to provide signals to delay components D1 to Dn. The respective components are: 35.2 to 35.14. The upper and lower branches of the split signals are re-combined in adders 35.3, 35.7 and 35.11. The signal selection switch, Switch unit 35.14 selects one of the IF signals present at 35.3, 35.7 and 35.11 combiner outputs. The signal selection is controlled by the "Control Select Signals" generated by unit 35.21. The selected signal at the output port of switch 35.14 is provided to 35.15 demodulator and PE monitor NEC detector. Output port 35.16 provides signals to 35.19 Pseudo Error NEC detector additional processing and in turn for signal shaping by a LPF 35.20 for providing signals to the Control Select Generator 35.21. The FR is a combination of an adaptive Feher Equalizer (FE) with selectable and switchable delay components among several branches or "rake branches" of the receiver structure. In this embodiment the receiver operates based on the principle that if the PE detector and/or alternate NEC circuit has a relatively high Pe on line state then one or more of the component values of the delay elements will be switched out or in, that is selected, and similarly the gain values of the adaptive equalizer A1, A2, . . . , An will be changed, continuously or in discrete steps.

Figure 36:
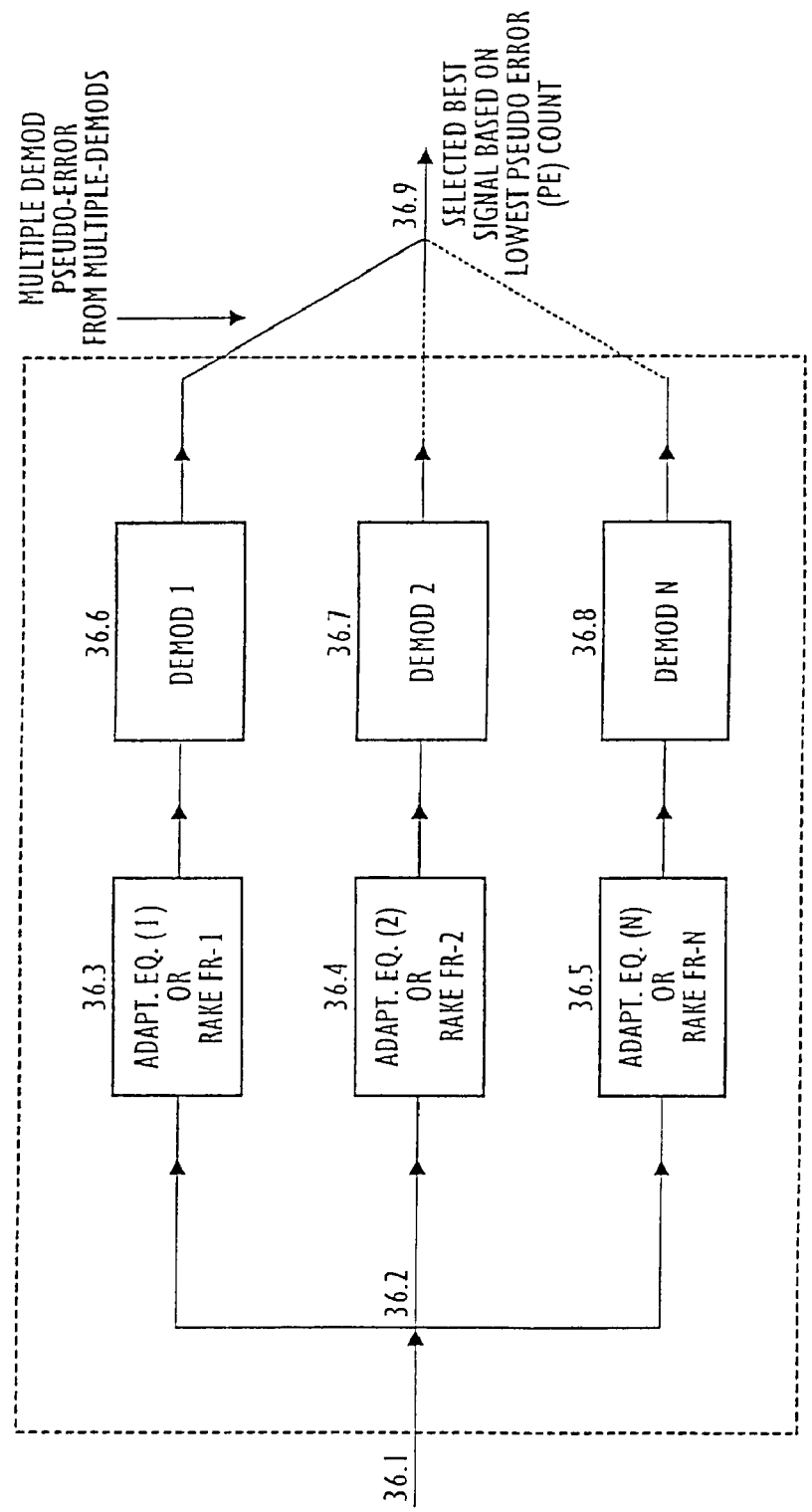
FIG. 36 shows an implementation architecture for multiple adaptive FE and FR circuit embodiments with multiple demodulators.

In FIG. 36 an implementation architecture for multiple Adaptive Feher Equalizers (FE) and Feher Rakes (FR) with one or more demodulators is illustrated. The received signal on lead 36.1 is provided to splitter port 36.2 and the splitter provides signals to units 36.3, 36.4 and 36.5. These units are FE and FR based on the previously described embodiments. These units provide signals to units 36.6, 36.7 and 36.8 for multiple signal demodulation. Single or multiple PE monitor (s) 36.10 provide control signals to select by selection switch 36.9 the best signal.

Figure 37:
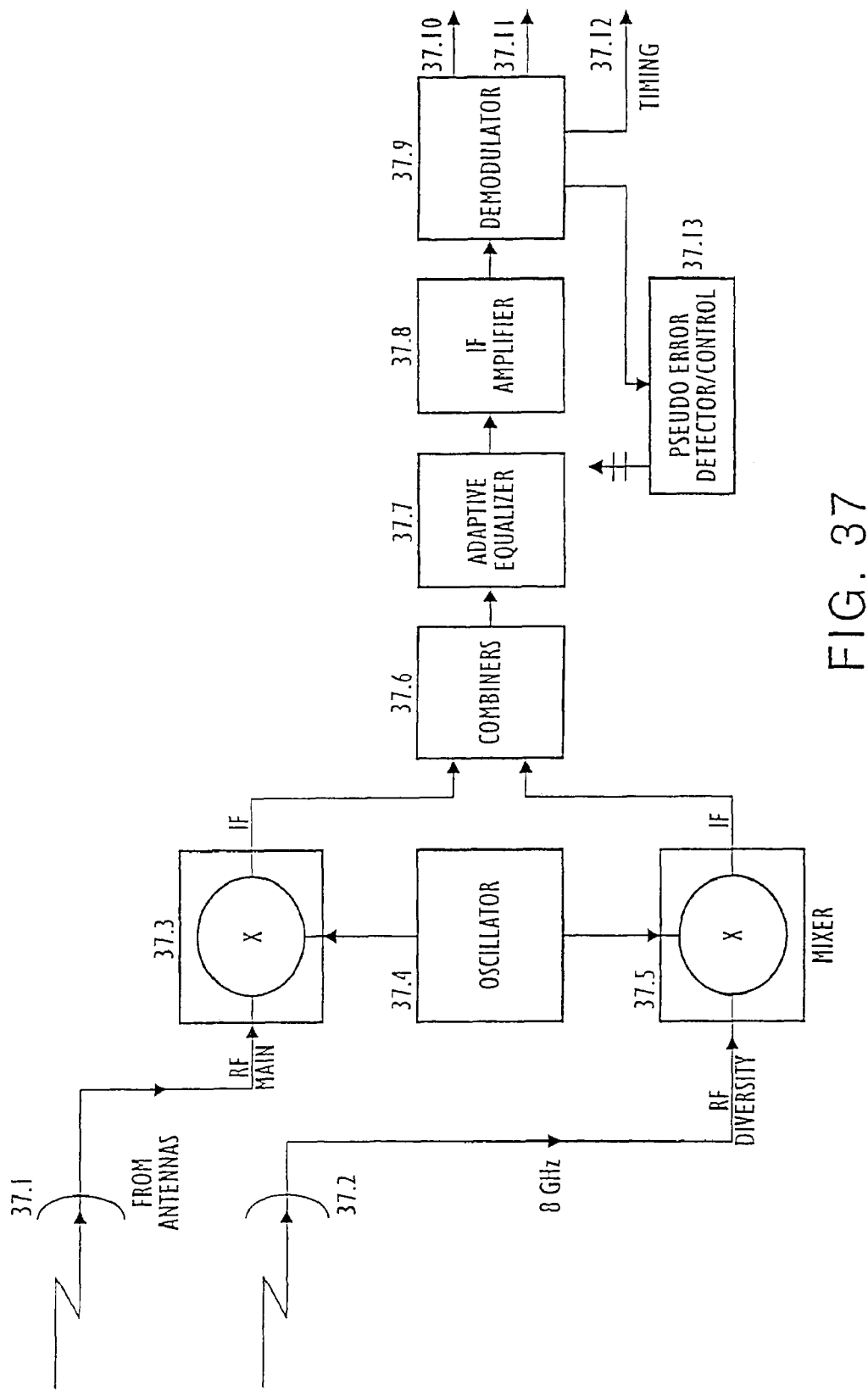
FIG. 37 is a block diagram implementation of a two branch diversity receiver with an adaptive equalizer and a single demodulator. A NRED based circuit generates "smart" diversity selection and/or control signals.

FIG. 37 shows a 2-branch diversity receiver with an adaptive equalizer and a single demodulator. In this embodiment FQPSK and/or FQPSK type of signals are first combined, in combiner unit 37.6 and are afterwards Adaptively Equalized in unit 37.7. Receiver antennas 37.1 and 37.2 provide signals to RF mixers/down-converters 37.3 and 37.5. Oscillator and/or Frequency Synthesizer 37.4 provides Carrier Wave signals for down-conversion. The IF down-converted signals are provided to combiner and/or switch unit 37.6, followed by adaptive equalizer 37.7, by optional Linear or NLA amplifier 37.8 and by Demodulator 37.9. The output demodulated data is available on port 37.10, the received/bit synchronized clock on port 37.11 and additional timing, such as symbol timing or block sequence timing on 37.12. One or more of the units and elements of this invention, described in conjunction with previous figures are used in the architecture of this FIG. 37. The PE and/or other NEC generated control signals provide for best possible combining, including "Equal Gain Combining", "Weighted Gain Combining", "Selective Combining" and other combining methods described in the prior art literature. A fundamental difference is that in this invention the actual Pseudo-Error rate is used as the pre dominant control signal generator and the PE monitor selects and/or combines the best performance BER signals, while the prior art combiners select or combine based on the received Carrier Power or received Carrier-to-Noise (C/N) ratio. Combining or selecting signals, based on received C/N or received carrier power (C) may lead to the selection of the inferior performance channel or combing with the wrong ratio or wrong weight, and in particular if the RF channel has serious frequency selective fades. For example the "main RF signal" designated RF main from antenna 37.1 has in one instant a much higher received carrier power than the carrier power on RF diversity antenna 37.2. Based on prior art receivers, combiners and diversity selection criteria the "main" signal would be selected as it has a higher C and thus higher C/N. However, in a severe RF selective faded environment even though the C power of the main branch, antenna 37.1 is much larger than that of the diversity antenna 37.2. In this instance the main antenna signal has much more RF frequency selective fade thus much worse performance the prior art receiver would choose/select the main branch with its poor and inferior performance, while the PE and/or other NEC based control signal disclosed in this invention would select the diversity signal with its superior performance.

Additional Description

Having now described numerous embodiments of the inventive structure and method in connection with particular figures or groups of figures, and having set forth some of the advantages provided by the inventive structure and method, we now highlight some specific embodiments having particular combinations of features. It should be noted that the embodiments described heretofore, as well as those highlighted below include optional elements or features that are not essential to the operation of the invention.

A first embodiment (1) provides a bit rate agile communication system comprises a splitter receiving an input signal and splitting the input signal into a plurality of baseband signal streams; a baseband signal processing network receiving the plurality of baseband signal streams and generating cross-correlated cascaded processed and filtered bit rate agile (BRA) in-phase and quadrature-phase baseband signals; and a quadrature modulator receiving and quadrature modulating the cross-correlated filtered in-phase and quadrature-phase baseband signals to generate a quadrature modulated output signal.

A second embodiment (2) further requires of the bit rate agile communication system that the baseband signal processing network includes a cross-correlator and at least one bit rate agile cascaded mis-matched (ACM) modulator filter.

A third embodiment (3) further requires of the bit rate agile communication system that it comprise: a demodulator structure having at least one bit rate agile (BRA) cascaded mis-matched (ACM) demodulation filter which is mis-matched (MM) to the cascaded processed and filtered modulated signal, and operating to demodulate the bit rate agile signal.

A fourth embodiment (4) further requires of the bit rate agile communication system that the at least one processed and filtered baseband signal is generated by a plurality of modulator filters, and at least one bit rate agile (BRA) demodulator filter is used for signal demodulation.

A fifth embodiment (5) further requires of the bit rate agile communication system that the plurality of modulator filters, and the demodulator filter are connected in either serial, parallel, or a combination of serial and parallel topology.

A sixth embodiment (6) provides bit rate agile communication system comprising:
a baseband signal processing network receiving parallel baseband signal streams and generating combined Time Constrained Signal (TCS) response and Long Response (LR) filtered in-phase and quadrature-phase baseband signals; and a quadrature modulator receiving and quadrature modulating the Time Constrained Signal (TCS) response and Long Response (LR) filtered in-phase and quadrature-phase baseband signals to generate a quadrature modulated bit rate agile output signal.

A seventh embodiment (7) further requires that the bit rate agile system further comprise: a transmit amplifier receiving the quadrature modulated output signal and generating an amplified transmit signal for coupling to a transmission medium.

An eighth embodiment (8) further requires that the bit rate agile system further comprising a demodulator receiving and demodulating the bit rate agile transmit signal.

A ninth embodiment (9) provides in a communication system, a method for generating bit rate agile signals comprising steps of: receiving an input signal and converting the input signal into a plurality of signal streams; processing the plurality of signal streams to generate cross-correlated signals having changeable amounts of filtering for bit rate agile in-phase and quadrature-phase baseband signals; and modulating the cross-correlated filtered in-phase and quadrature-phase baseband signals to generate a quadrature modulated bit rate agile output signal.

A tenth embodiment (10) provides in a signal transmission system, a method for generating bit rate agile signals comprising steps of: receiving a plurality of signal streams; processing the plurality of signal streams to generate cascaded Time Constrained Signal (TCS) response and Long Response (LR) filtered in-phase and quadrature-phase baseband signals; and modulating the Time Constrained Signal (TCS) response and Long Response (LR) filtered in-phase and quadrature-phase baseband signals to generate a quadrature modulated bit rate agile output signal.

An eleventh embodiment (11) provides a Bit Rate Agile (BRA) structure comprising a input port for receiving input data; a splitter having an input coupled to the input port, and serving to split the input data into baseband signal streams; a baseband signal processing network for receiving the baseband signal streams and providing cross-correlated and filtered Bit Rate Agile (BRA) in phase and quadrature phase baseband signals; a Quadrature Modulator serving to quadrature modulate the cross-correlated filtered in phase and quadrature phase baseband signals; an interface transmitter port to provide the quadrature modulated signal to the transmission medium; an interface receiver port to provide connection of the cross-correlated filtered quadrature modulated signal to the demodulator; and a demodulator structure to serve for Bit Rate Agile (BRA) signal demodulation having Bit Rate Agile (BRA) demodulation filters Mis-Matched (MM) to that of the modulator filters.

A twelfth embodiment (12) further requires of the Bit Rate Agile (BRA) structure structure that the processed in phase and quadrature phase baseband signals have amplitudes such that their vector sum is substantially constant and has reduced resultant quadrature modulated envelope fluctuations.

A thirteenth embodiment (13) further requires that the Bit Rate Agile (BRA) structure comprises means for selectively reducing the cross correlating factor down to zero.

A fourteenth embodiment (14) provides a Bit Rate Agile (BRA) structure comprising a baseband signal processing circuit receiving one or more baseband signal streams and providing cross-correlated and filtered Bit Rate Agile (BRA) in-phase and quadrature-phase baseband signals; a quadrature modulator serving to quadrature modulate the cross-correlated filtered in phase and quadrature phase baseband signals; a transmit amplifier to provide the quadrature modulated signal to the transmission medium; an interface receiver port to provide connection of the cross-correlated filtered quadrature modulated signal to the demodulator; and a demodulator structure to serve for Bit Rate Agile (BRA) signal demodulation.

A fifteenth embodiment (15) provides a Bit Rate Agile (BRA) structure comprising: a baseband signal processing network for receiving baseband signal streams and providing cascaded Bit Rate Agile (BRA) Time Constrained Signal (TCS) response and Long Response (LR) filtered in phase and quadrature phase baseband signals; a Quadrature Modulator serving to quadrature modulate the cascaded Time Constrained Signal (TCS) response and Long Response (LR) filtered in phase and quadrature phase baseband signals; an interface transmitter port to provide the quadrature modulated signal to the transmission medium; an interface receiver port to provide connection of the filtered quadrature modulated signal to the demodulator; and a demodulator structure to serve for signal demodulation having Bit Rate Agile (BRA) demodulation filters Mis-Matched (MM) to that of the modulator filters.

A sixteenth embodiment (16) provides a Bit Rate Agile (BRA) structure comprising: a input port for receiving input data; a splitter having an input coupled to the input port, and serving to split the input data into baseband signal streams; a baseband signal processing network for receiving the baseband signal streams and providing cascaded Time Constrained Signal (TCS) response and Long Response (LR) filtered in phase and quadrature phase baseband signals; a Quadrature Modulator serving to quadrature modulate the Time Constrained Signal (TCS) response and Long Response (LR) filtered in phase and quadrature phase baseband signals; a transmit amplifier to provide the quadrature modulated signal to the transmission medium; an interface receiver port to provide connection of the filtered quadrature modulated signal to the demodulator; and a demodulator structure to serve for Bit Rate Agile (BRA) signal demodulation.

A seventeenth embodiment (17) provides a structure comprising: an input port for receiving baseband signals; a baseband signal processing network for receiving the baseband signals and providing cross-correlated bit rate agile cascaded mis-matched (ACM) processed and filtered in-phase and quadrature-phase baseband signals.

A eighteenth embodiment (18) provides a signal processing, modulation, transmission, signal reception and demodulation system, for Bit Rate Agile (BRA), Modulation Demodulation (Modem) Format Selectable (MFS) and Code Selectable (CS) systems comprising: (a) means for input port for receiving input data; (b) splitter means serving for BRA, MFS and CS signal splitting, having an input coupled to the input port, and serving to split the input data into baseband signal streams; (c) means for BRA, MFS and CS baseband signal processing; (d) means for receiving the baseband signal stream and providing for BRA, MFS and CS systems changeable amounts of cross-correlation between Time Constrained Signal (TCS) response processors combined with TCS and Long Response (LR) processors; (e) means for cross-correlated processed in phase (I) and quadrature (Q) phase baseband signals for quadrature modulation to the I and Q input ports of the Quadrature Modulator (QM); (f) means for an interface unit to provide the quadrature modulated data to the transmission medium; (g) means for a receiver interface unit for connection of the received cross-correlated signal to the BRA and MFS demodulator; (h) means for BRA, MFS and CS demodulation; (i) means for post-demodulation Mis-Matched (MM) filtering of the BRA MFS and CS demodulated signals in which the MM demodulator filters are mismatched to that of the BRA and MFS filters.

A nineteenth embodiment (19) provides a cross-correlated signal processor comprising: (a) means for Bit Rate Agile (BRA), and Modulation-Demodulation (Modem) Format Selectable (MFS) input port for receiving input data; (b) means for providing BRA and MFS in-phase (I) and quadrature phase (Q) signals; (c) BRA and MFS means for cross-correlating a fraction of a symbol or one or more symbols of the I signal with one or more symbols of the Q signal; (d) means for implementing the BRA and MFS cross-correlated signals by analog active circuits, analog passive circuits, by digital circuits or any combination thereof; (e) means for switching in-out additional filters in the I and/or Q channels; (f) means for Quadrature modulating the I and Q signals; (g) means for Linear and/or Nonlinear amplification to provide to the antenna; (h) a receiver port for connection of the received cross-correlated signal to the BRA and MFS demodulator; (i) a BRA and MFS quadrature demodulator; and (j) a Mis-Matched (MM) BRA and MFS demodulator filter set in which the demodulator filter set is MM to that of the BRA and MFS filter set of the modulator.

A twentieth embodiment (20) provides a cross-correlated signal processor for Bit Rate Agile (BRA) and Modulation-Demodulation (Modem) Format Selectable (MFS) and Code Selectable (CS) means comprising: (a) means for providing in-phase and quadrature phase signals; (b) means for cross-correlating a fraction of a symbol or one or more than one symbol of the in-phase (I) signal with a fraction of a symbol or one or more than one symbol of the quadrature-phase (Q) signal; (c) means for generating filtered cross-correlated I and Q signals; (d) means for implementing the cross-correlated signals by analog active or passive circuits, by digital circuits or combination thereof; (e) means for providing a control circuit to select from a set of predetermined cross-correlated signal elements filters and selectable waveforms in the I and/or Q channels; (f) means for Quadrature modulating the I and Q signals; (g) means for Linear and/or Nonlinear amplification to provide to the antenna; (h) a receiver port for connection of the received cross-correlated signal to the BRA and MFS demodulator; (i) a BRA and MFS quadrature demodulator; (j) a Mis-Matched (MM) BRA and MFS demodulator filter set in which the demodulator filter set is MM to that of the BRA and MFS filter set of the modulator.

A twenty-first embodiment (21) provides a Cross-correlated signal processor for Bit Rate Agile (BRA) and Modulation-Demodulation (Modem) Format Selectable (MFS) and Code Selectable (CS) means comprising: (a) processing means for one or more input signals and providing in-phase (I) and quadrature phase (Q) signals; (b) means for cross-correlating the in-phase and quadrature shifted signals; (c) means for generating in-phase and quadrature shifted output signals having amplitudes such that the vector sum of the output signals is approximately the same at virtually all phase angles of each bit period for one set of cross-correlation and filter parameters and the vector sum is not constant for an other set of chosen filter parameters; (d) means for quadrature modulating the in-phase and quadrature output signals, to provide a cross-correlated modulated output signal; (e) means for providing a control circuit to select from a set of predetermined cross-correlated signal elements filters and selectable waveforms in the I and/or Q channels; (f) means for Quadrature modulating the I and Q signals; (g) means for Linear and/or Nonlinear amplification to provide to the antenna; (h) a receiver port for connection of the received cross-correlated signal to the BRA and MFS demodulator; (i) a BRA and MFS quadrature demodulator; and (j) a Mis-Matched (MM) BRA and MFS demodulator filter set in which the demodulator filter set is MM to that of the BRA and MFS filter set of the modulator.

A twenty-second embodiment (22) provides a cross-correlated signal processor comprising: (a) means for cross-correlating a fraction, or one or more than one symbol synchronous and/or asynchronous time constrained signal (TCS) response and cascaded long response (LR) filtered signal symbols of one or more input signals with signal symbols of a quadrature phase shifted signal of the in-phase signal, and providing in-phase (I) and quadrature phase (Q) shifted signals for Bit Rate Agile (BRA), cascaded mis-matched (ACM) Modulation-Demodulation (Modem) Format Selectable (MFS) and Code Selectable (CS) processing, according to the following schedule: (i) when the in-phase channel signal is zero, the quadrature shifted signal is close to the maximum amplitude normalized to one (1); (ii) when the in-phase channel signal is non-zero, the maximum magnitude of the quadrature shifted signal is reduced from 1 (normalized) to A, where 0_A_1; (iii) when the quadrature channel signal is zero, the in-phase signal close to the maximum amplitude; (iv) when the quadrature channel signal is non-zero, the in-phase signal is reduced from 1 (normalized) to A, where 0_A_1; (b) means for quadrature modulating the in-phase and quadrature output signals to provide a cross-correlated modulated output signal; (c) controlling means and signal selection means for BRA rate, MFS and CS processor selection and selection for Linear and/or Non-Linearly Amplified (NLA) baseband and/or of Quadrature modulated signals; (d) coupling port means to the transmission medium; (e) a receiver port for connection of the received cross-correlated signal to the BRA, MFS and CS demodulator; (f) a BRA, MFS and CS quadrature demodulator; and (g) a Mis-Matched (MM) demodulator filter set for BRA, MFS and CS in which the demodulator filter set is MM to that of the BRA, MFS and BRA filter set of the modulator.

A twenty-third embodiment (23) provides a structure for trellis coding and decoding, of extended memory Bit Rate Agile (BRA), Modulation-Demodulation (Modem) Format Selectable (MFS) and Code Selectable (CS) input port for receiving input data comprising: a trellis encoder; a BRA, MFS and CS splitter having an input coupled to the input port, and serving to split the input data into baseband signal streams; a BRA, MFS and CS baseband signal processing network for receiving the baseband signal streams and providing BRA, MFS and CS in phase (I) and quadrature (Q) phase baseband signals to the I and Q input ports of the transmitter; means for baseband signal processing for receiving the baseband signal streams and providing for BRA, MFS and CS systems changeable amounts of cross-correlation; means for selectively reducing the cross-correlating factor down to zero between Time Constrained Signal (TCS) response processors combined with TCS and Long Response (LR) processors; a receiver port for connection of the received cross-correlated signal to the BRA and MFS demodulator; a BRA and MFS quadrature demodulator; and a Mis-Matched (MM) BRA and MFS demodulator filter set in which the demodulator filter set is MM to that of the BRA and MFS filter set of the modulator.

A twenty-fourth embodiment (24) provides a cross correlated quadrature architecture signal processor for producing Bit Rate Agile (BRA), cross-correlated in phase and quadrature phase signal streams for modulation by a Quadrature Modulator and transmission and for signal demodulation comprising: (a) means for receiving an input BRA signal selected from the group of binary, multi-level, and analog signals and combinations thereof; (b) filtering means of the BRA input signal; (c) BRA signal shaping means for the filtered input signal; (d) amplification means for varying the modulation index of the BRA signal, the amplifier receiving the filtered input signal and providing an amplified input signal; (e) means for BRA signal splitting for receiving the amplified input signal; (f) cross correlation means of BRA data streams; and a BRA signal processor means having an in phase and quadrature phase channel each receiving one of the cross-correlated data streams, each of the in phase and quadrature phase channel having a first delay gain filter, means for generating BRA Cosine and BRA Sine values for the in phase and quadrature phase channel data stream; (g) a BRA wave shaper and a second BRA delay gain filter, such that the signal processor provides in phase and quadrature phase cross correlated data signal processor; (h) means for quadrature modulation with a BRA modulated signal adaptable for coherent or non-coherent demodulation of the quadrature BRA Frequency Modulated (FM) signal; (i) controlling means and signal selection means for BRA rate processor selection; (j) selection means for Linear and/or Non-Linearly Amplified (NLA) baseband and/or of modulated signals coupling port means to the transmission medium; (k) receiver port means for connection of one or more received cross-correlated signals to the BRA demodulator; (l) BRA demodulator means; and (m) Mis-Matched (MM) demodulator filtering means for BRA, MFS and CS demodulation in which the demodulator filter set is MM to that of the BRA, MFS and BRA filter set of the modulator.

A twenty-fifth embodiment (25) provides a signal processing, modulation, transmission, signal reception and demodulation system, designated as Feher's Gaussian Minimum Shift Keyed (GMSK) for Bit Rate Agile (BRA), Modulation Demodulation (Modem) Format Selectable (MFS) and Code Selectable (CS) systems comprising: (a) input port for receiving input data; (b) Gaussian low-pass filter and presetable gain integrator for processing the input data and providing filtered input data; (c) a splitter having an input coupled to the input port, and serving to split the filtered input data into in phase (I) and quadrature phase (Q) channel cross coupled data streams such that the I and Q data streams are proportional in gain and phase to the input data; (d) a signal processing network for receiving the I and Q channel data streams and providing processed in phase and quadrature phase signals, the signal processing network including a signal processor for varying the modulation index for the signal processing network; (e) means for generating Cosine and Sine values for the I and Q channel BRA, MFS and CS data streams; (f) means for filtering by bit rate agile FIR or IIR or switched filter and/or other post GMSK shaping filters the signals in the I and Q channels such that the signal processor provides in phase and quadrature phase cross correlated data signals for quadrature modulation with a modulated signal suitable for amplification in linear and non-linear mode; (g) means for providing the amplified signal to the transmission port; (h) a receiver port for connection of the received cross-correlated signal to the BRA and MFS demodulator; (i) a BRA and MFS quadrature demodulator; and (j) a Mis-Matched (MM) BRA and MFS demodulator filter set in which the demodulator filter set is MM to that of the BRA and MFS filter set of the modulator.

A twenty-sixth embodiment (26) provides a structure comprising: a input port for receiving baseband signals; and a baseband signal processing network for receiving the baseband signals and providing cross-correlated bit rate agile Peak Limited (PL) in-phase and quadrature-phase baseband signals.

A twenty-seventh embodiment (27) provides a structure for Orthogonal Frequency Division Multiplexed (OFDM) signals comprising: a input port for receiving OFDM baseband signals; and a baseband signal processing network for receiving the baseband signals and providing cross-correlated filtered in-phase and quadrature-phase baseband signals.

A twenty-eighth embodiment (28) provides a structure comprising: a input port for receiving Orthogonal Frequency Division Multiplexed (OFDM) baseband signals; and a baseband signal processing network for receiving the OFDM signals and providing cross-correlated filtered in-phase and quadrature-phase baseband signals.

A twenty-ninth embodiment (29) provides a structure comprising: a input port for receiving Orthogonal Frequency Division Multiplexed (OFDM) baseband signals; and a baseband signal processing network for receiving the OFDM signals and providing cross-correlated Peak Limited (PL) in-phase and quadrature-phase baseband signals.

A thirtieth embodiment (30) provides a structure comprising: an input port for receiving baseband signals; a baseband signal processing network for receiving the baseband signals and providing more than two state cross-correlated filtered in-phase and quadrature-phase baseband signals; a Quadrature Modulator serving to quadrature modulate the cross-correlated filtered in-phase and quadrature-phase baseband signals; and a transmit amplifier to provide the quadrature modulated signal to the transmission medium.

A thirty-first embodiment (31) provides a Bit Rate Agile (BRA) structure comprising: a input port for receiving single or plurality of baseband binary input signals; a baseband signal processing network for receiving the baseband binary signals and providing combined Time Constrained Signal (TCS) response and Long Response (LR) filtered multi-level in-phase and quadrature-phase baseband signals; and a Quadrature Modulator serving to quadrature modulate the Time Constrained Signal (TCS) response and Long Response (LR) filtered in-phase and quadrature-phase baseband signals; a transmit amplifier to provide the quadrature modulated signal to the transmission medium; an interface receiver port to provide connection of the filtered quadrature modulated signal to the demodulator; and a demodulator structure to serve for signal demodulation.

A thirty-second embodiment (32) provides a structure comprising: a input port for receiving a plurality of baseband signals; a baseband signal processing network for receiving the plurality of baseband signals and providing cross-correlated filtered in-phase and quadrature-phase baseband signals to two or more quadrature modulators for quadrature modulation; a set of two or more transmit amplifiers to amplify and provide the quadrature modulated signals for RF combining; and a combiner device for RF combining of the quadrature modulated amplified signals.

A thirty-third embodiment (33) provides a structure comprising: a input port for receiving a plurality of baseband signals; a baseband signal processing network for receiving the plurality of baseband signals and providing in-phase and quadrature-phase filtered baseband signals to two or more quadrature modulators for quadrature modulation; and a set of two or more transmit amplifiers to amplify and couple the quadrature modulated amplified signals to two or more antennas.

A thirty-fourth embodiment (34) provides a structure comprising: a input port for receiving baseband signals; a baseband signal processing network for receiving and splitting the signals and for providing cross-correlated filtered in-phase and quadrature-phase baseband signals to two or more quadrature modulators for quadrature modulation; and a set of two or more transmit amplifiers to amplify and provide the quadrature modulated amplified RF signals to an antenna array.

A thirty-fifth embodiment (35) provides a structure comprising: a signal processing network for receiving and splitting signals and for providing cascaded Time Constrained Signal (TCS) response and Long Response (LR) filtered in-phase and quadrature-phase baseband signals to two or more quadrature modulators for quadrature modulation; a set of two or more transmit amplifiers to amplify and provide the quadrature modulated amplified RF signals for RF combining; and a combiner device for RF combining of the quadrature modulated amplified signals.

A thirty-sixth embodiment (36) provides a structure comprising: an interface receiver port to provide connection of received Bit Rate Agile (BRA) cross-correlated filtered quadrature modulated signal to the demodulator; and a demodulator structure to serve for signal demodulation of the signal.

A thirty-seventh embodiment (37) provides an adaptive equalizer structure comprising: an interface receiver port to provide connection of received modulated signal to the pre-demodulation adaptive equalizer; a pre-demodulation adaptive equalizer structure comprising splitter, multiplier and delay structure for generating a control signal and received modulated signal time delayed product in one branch of the splitter and coupling the signal time delayed product in one branch of the splitter and the received modulating signal in the other branch of the splitter to a signal combiner; a signal combiner structure for combining the delayed control signal and received modulated signal product; a demodulator structure for demodulating the combined delayed control signal and received modulated signal product; and a control signal processor for generation of and connection of the control signal to the product multiplier circuit.

A thirty-eighth embodiment (38) provides an adaptive equalizer and switchable delay structure comprising: an interface receiver port to provide connection of received modulated signal to a plurality of splitters, amplifiers, delay elements and signal combiners for signal selection of the received modulated signal; a demodulator structure for demodulating the selected received modulated signal; and a control signal processor for generation of the control signal.

The invention further provides methods and procedures performed by the structures, devices, apparatus, and systems described herein before, as well as other embodiments incorporating combinations and subcombinations of the structures highlighted above and described herein.

All publications including patents, pending patents and reports listed or mentioned* in these publications and/or in this patent/invention are herein incorporated by reference to the same extent as if each publication or report, or patent or pending patent and/or references listed in these publications, reports, patents or pending patents were specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A method for:
filtering a first bit rate signal by a first transmit filter and modulating by a modulator said first bit rate filtered signal into a Quadrature Amplitude Modulated (QAM) Code Division Multiple Access (CDMA) signal;
processing, cross-correlating and filtering a second bit rate signal by a Time Constrained Signal (TCS) response processor, a cross-correlator and a second transmit filter into a processed, cross-correlated, filtered in-phase and quadrature-phase signal and modulating by said modulator said second bit rate processed, cross-correlated and filtered signal into a modulated Time Division Multiple Access (TDMA) signal, said second bit rate is different from said first bit rate;
nonlinearly amplifying said modulated TDMA signal and for providing said TDMA amplified signal to a first transmitter for transmission of said TDMA amplified signal;
linearly amplifying said modulated CDMA signal and for providing said amplified CDMA signal to a second transmitter for transmission of said linearly amplified CDMA modulated signal, wherein said second transmitter is operated in a different Radio Frequency (RF) band than said first transmitter; and receiving and demodulating by a receive antenna and a demodulator a transmitted modulated TDMA and a transmitted modulated CDMA signal.

2. The method of claim 1 wherein said receiving and demodulating by said receive antenna and said demodulator comprises step of receive filtering and receive processing for filtering, processing and providing demodulated cross-correlated in-phase and quadrature-phase filtered signal, wherein said receive filtering is by a receive filter, said receive filter is a mis-matched filter to said TCS response processor and second transmit filter.

3. The method of claim 1, further comprising step of processing a third bit rate signal into a processed Code Division Multiple Access (CDMA) cross-correlated in-phase and quadrature-phase filtered baseband signal and providing said third bit rate processed CDMA cross-correlated filtered baseband signal to a modulator for modulating said third bit rate processed CDMA signal, said receiving and demodulating includes step of providing in a diversity receiver and a demodulator a demodulated and adaptive equalized signal and step of generating a Pseudo-Error (PE) detector generated control signal for control of said diversity receiver and said demodulator comprises a receive filter for receive filtering of said received and demodulated signal, wherein said receive filter is mis-matched to said first transmit filter, said receiver for receiving the transmitted signal comprises a liner Automatic Gain Control (AGC) circuit operated in a liner mode and a non-linear AGC circuit operated in a non-linear mode for reception and demodulation of said transmitted modulated signal.

4. The method of claim 1, wherein said first transmit filtering provides a time division multiplexed (TDM) Gaussian filtered baseband signal to said modulator for modulating Gaussian filtered modulated signal and further comprising step of processing said first bit rate signal into a processed cross-correlated time division multiple access (TDMA) in-phase and quadrature-phase signal and into a processed cross-correlated filtered Orthogonal Frequency Division Multiplex (OFDM) in-phase and quadrature-phase signal.

5. The method of claim 1, wherein said first transmit baseband filtering provides a time division multiplexed (TDM) Gaussian filtered baseband signal to said modulator for modulating Gaussian filtered modulated signal and further comprising step of processing said first bit rate signal into a processed cross-correlated time division multiple access (TDMA) in-phase and quadrature-phase signal and into a processed cross-correlated filtered Orthogonal Frequency Division Multiplex (OFDM) in-phase and quadrature-phase signal.

6. The method of claim 1 wherein said Quadrature Amplitude Modulated (QAM) signal comprises Orthogonal Frequency Division Multiplexed (OFDM) in-phase and quadrature-phase baseband modulated signal.

7. The method of claim 1 wherein said first transmit filter provides cross-correlated in-phase and quadrature-phase filtered baseband signal and said second transmit filter provides Orthogonal Frequency Division Multiplexed (OFDM) filtered signal.

8. The method of claim 1, wherein said first bit rate signal is a telemetry signal and further comprising a method for processing, modulating and transmitting a video signal into a Orthogonal Frequency Division Multiplexed (OFDM) modulated transmitted signal.

9. A method for:

processing, cross-correlating and filtering in a cellular device a first signal into a processed Code Division Multiple Access (CDMA), cross-correlated in-phase and quadrature-phase filtered baseband signal and modulating said processed, cross-correlated in-phase and quadrature-phase filtered CDMA baseband signal into a modulated CDMA signal;

processing and filtering in said cellular device said first signal into a processed Gaussian Minimum Shift Keying (GMSK) filtered baseband signal and modulating said processed filtered GMSK baseband signal into a modulated GMSK signal;

processing and filtering a second signal, in said cellular device, into a processed filtered Orthogonal Frequency Division Multiplexed (OFDM) baseband signal and modulating said OFDM baseband signal into an OFDM modulated signal;

transmitting by a transmitter, in said cellular device, said modulated CDMA signal or said modulated OFDM signal or said modulated GMSK signal.

10. The method of claim 9, further comprising step of receiving and demodulating in said cellular device, by a receive antenna and a demodulator a transmitted modulated TDMA and CDMA signal, said receiving and demodulating by comprises step of receive filtering and receive processing for filtering, processing and providing demodulated cross-correlated in-phase and quadrature-phase filtered signal, said receive filtering is by a receive filter and further comprising step of processing, modulating and transmitting a telemetry signal and comprising a method for processing, modulating and transmitting a video signal into a Orthogonal Frequency Division Multiplexed (OFDM) modulated transmitted signal.

11. The method of claim 9, further comprising step of said processing, cross-correlating, filtering processed GMSK cross-correlated in-phase and quadrature-phase filtered baseband signal in a Gaussian transmit baseband filter and of processing an input signal into a processed Time Division Multiple Access (TDMA) cross-correlated in-phase and quadrature-phase filtered baseband signal and providing said processed TDMA cross-correlated filtered baseband signal to a modulator for modulating said TDMA cross-correlated filtered baseband signal, further comprising step of receiving and demodulating in said cellular device, by a receive antenna and a demodulator in a diversity receiver and a demodulator for providing a demodulated and adaptive equalized signal and further comprising step of generating a Pseudo-Error (PE) detector generated control signal for control of said diversity receiver and said demodulator comprises a receive baseband filter for receive filtering of said received and demodulated signal, wherein said receive baseband filter is mis-matched to said Gaussian transmit baseband filter, said receiver for receiving the transmitted signal comprises a liner Automatic Gain Control (AGC) circuit operated in a liner mode and a non-linear AGC circuit operated in a non-linear mode.

12. The method of claim 9, further comprising method for processing an input signal, in said cellular device, into a Quadrature Amplitude Modulated (QAM) signal, said QAM signal comprises an Orthogonal Frequency Division Multiplexed (OFDM) in-phase and quadrature-phase cross-correlated baseband modulated signal.

13. The method of claim 9, further comprising method for processing and filtering an input signal into a cross-correlated time division multiple access (TDMA) filtered in-phase and quadrature-phase signal by a TDMA transmit filter and a receiver for receiving by a receive baseband filter a TDMA transmitted signal, wherein said receive baseband filter is mis-matched to said TDMA transmit filter.

14. The method of claim 9, wherein said processed, filtered Gaussian Minimum Shift Keying (GMSK) signal is a cross-correlated in-phase and quadrature-phase filtered baseband signal.

15. The method of claim 9, wherein said first signal is a signal used in a telemetry system and said second signal is a video signal.

16. A communication method for:
receiving in a receiver system a Time Division Multiple Access (TDMA) and a Orthogonal Frequency Division Multiplexed (OFDM) modulated signal for providing said received modulated TDMA or said received modulated OFDM signal to one or more demodulators for demodulation and processing of said received modulated TDMA or said received modulated OFDM signal into demodulated, baseband processed TDMA or OFDM signal; and
providing said demodulated, baseband processed TDMA or said demodulated, baseband processed OFDM signal to an interface baseband receiver port, said receiver system comprises a diversity receiver for diversity reception and said demodulated, baseband processed TDMA signal comprises cross-correlated in-phase and quadrature-phase baseband receive filtered signals.

17. The method of claim 16, further comprising step of processing an input signal into a processed Code Division Multiple Access (CDMA) cross-correlated in-phase and quadrature-phase filtered baseband signal and providing said processed CDMA cross-correlated filtered baseband signal to a modulator for modulating said processed CDMA signal and further comprising step of receiving in a diversity receiver a received CDMA signal, said diversity receiver comprises step of providing in said diversity receiver a demodulated and adaptive equalized signal and step of generating a Pseudo-Error (PE) detector generated control signal for control of said diversity receiver and said demodulator comprises a receive filter for receive filtering of said received and demodulated CDMA signal and said receiver further comprises a liner Automatic Gain Control (AGC) circuit operated in a liner mode and a non-linear AGC circuit operated in a non-linear mode for reception and demodulation of a transmitted modulated signal.

18. The method of claim 16, further comprising step of receiving and demodulating by a receive antenna and a demodulator a transmitted modulated TDMA and CDMA signal, said receiving and demodulating comprises step of receive filtering and receive processing for filtering, processing and providing demodulated cross-correlated in-phase and quadrature-phase filtered signal, said receive filtering is by a receive filter, further comprising step of processing, modulating and transmitting a telemetry signal and comprising a method for processing, modulating and transmitting a video signal into a Orthogonal Frequency Division Multiplexed (OFDM) modulated transmitted signal.

19. The method of claim 16, further comprising step of processing a data signal into a processed Collision Sense Multiple Access (CSMA) signal for modulation and transmission of said processed CSMA signal.

20. The method of claim 16, further comprising method for providing said baseband processed TDMA or OFDM signal to an interface unit for transmission of said provided signal to said interface unit by a wired connection.

\* \* \* \* \*